United States Patent [19]
Matsui et al.

[11] Patent Number: 5,858,275
[45] Date of Patent: Jan. 12, 1999

[54] CHLOROBENZENE DERIVATIVE AND LIQUID CRYSTAL COMPOSITION CONTAINING THE SAME

[75] Inventors: Shuichi Matsui; Tomoyuki Kondo; Kazutoshi Miyazawa; Yasuyuki Goto; Etsuo Nakagawa; Shinichi Sawada, all of Chiba, Japan

[73] Assignee: Chisso Corporation, Osaka, Japan

[21] Appl. No.: 809,061

[22] PCT Filed: Sep. 22, 1995

[86] PCT No.: PCT/JP95/01917

§ 371 Date: Mar. 10, 1997

§ 102(e) Date: Mar. 10, 1997

[87] PCT Pub. No.: WO96/09272

PCT Pub. Date: Mar. 28, 1996

[30] Foreign Application Priority Data

Sep. 22, 1994 [JP] Japan .................................. 6-228522

[51] Int. Cl.⁶ .......................... C09K 19/30; C09K 19/12; C09K 19/34; C07C 19/08
[52] U.S. Cl. ................. 252/299.63; 252/299.66; 252/299.61; 570/128
[58] Field of Search ......................... 252/299.63, 299.66, 252/299.61; 570/128

[56] References Cited

U.S. PATENT DOCUMENTS

| | | | |
|---|---|---|---|
| 5,254,698 | 10/1993 | Coates et al. | 549/369 |
| 5,271,865 | 12/1993 | Hittich et al. | 252/299.01 |
| 5,328,644 | 7/1994 | Goulding et al. | 252/299.66 |
| 5,368,772 | 11/1994 | Rieger et al. | 252/299.63 |
| 5,476,611 | 12/1995 | Nolan et al. | 252/299.01 |
| 5,480,581 | 1/1996 | Plach et al. | 252/299.63 |
| 5,498,365 | 3/1996 | Nolan et al. | 252/299.01 |
| 5,520,846 | 5/1996 | Plach et al. | 252/299.63 |
| 5,534,189 | 7/1996 | Nakagawa et al. | 252/299.63 |
| 5,578,241 | 11/1996 | Plach et al. | 252/299.01 |
| 5,616,284 | 4/1997 | Hittich et al. | 252/299.63 |

FOREIGN PATENT DOCUMENTS

| | | |
|---|---|---|
| 0449288 | 10/1991 | European Pat. Off. . |
| 0497176 | 8/1992 | European Pat. Off. . |
| 4027315 | 3/1991 | Germany . |
| 4-501576 | 3/1992 | Japan . |
| 5-279279 | 10/1993 | Japan . |
| WO91/03445 | 3/1991 | WIPO . |
| WO91/17134 | 11/1991 | WIPO . |

OTHER PUBLICATIONS

Goulding et al., Liquid Crystals, 1993, vol. 14 (5), pp 1397–1408.

*Primary Examiner*—C. H. Kelly
*Attorney, Agent, or Firm*—Wenderoth, Lind & Ponack, L.L.P.

[57] ABSTRACT

Chlorobenzene derivatives which have the following four-ring structure and are preferably usable for display devices of active matrix mode, and liquid crystal compositions comprising the derivative are provided:

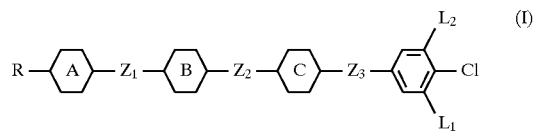

wherein ring A, ring B, and ring C independently represent trans-1,4-cyclohexylene group or 1,4-phenylene group, one or more hydrogen atoms on the six-membered ring of which may be replaced by halogen atoms, $Z_1$, $Z_2$, and $Z_3$ represent —$CH_2CH_2$— or single bond, respectively, provided that at least one of them represents —$CH_2CH_2$—, $L_1$ and $L_2$ represent H or halogen atom, and R represents an alkyl group or alkoxy group having 1 to 10 carbon atoms, provided that when $Z_1$ and $Z_3$ represent single bond and $Z_2$ represents —$CH_2CH_2$—, ring A represents 1,4-phenylene group, and when $Z_1$ and $Z_2$ represent single bond, and $Z_3$ represents —$CH_2CH_2$—, in no case does ring A represents trans-1,4-cyclohexylene group and both ring B and ring C represent 1,4-phenylene group at the same time.

14 Claims, No Drawings

CHLOROBENZENE DERIVATIVE AND LIQUID CRYSTAL COMPOSITION CONTAINING THE SAME

TECHNICAL FIELD

The present invention relates to a liquid crystalline compound. More specifically, the present invention relates to a chlorobenzene derivative having a four-ring structure, a liquid crystal composition comprising the derivative, and a liquid crystal display device comprising the liquid crystal composition.

BACKGROUND ART

Display devices which have employed a liquid crystal composition have widely been used for watches, desktop calculators, and others. These liquid crystal display devices employ the optical anisotropy and dielectric anisotropy of liquid crystal substances. Liquid crystal phase includes a nematic liquid crystal phase, smectic liquid crystal phase, and cholesteric liquid crystal phase. Among the display devices, ones which have employed a nematic liquid crystal phase have most widely been used practically. Mode of liquid crystal display device includes a TN (twisted nematic) mode, DS (dynamic scattering) mode, guest-host mode, and DAP (Deformation of Aligned Phases) mode corresponding to electro-optic effect employed therein. Liquid crystalline compounds used in the display devices of those modes desirably exhibit a liquid crystal phase in a temperature range as wide as possible and are required to be stable against moisture, heat, and air. Particularly, demand for display devices of active matrix mode typified by Thin Film Transistor (TFT) mode has recently been increased. When liquid crystal panels are optically designed, the product $\Delta n \cdot d$ of the thickness of the cell of a display device (d) and the value of optical anisotropy ($\Delta n$) must be adjusted to a certain value. At that time, since d tends to decrease partly due to the progress in the reduction of cell thickness in TFT mode, liquid crystalline compounds having a large $\Delta n$ became necessary. Liquid crystalline compounds are also required to exhibit a liquid crystal phase in a wide temperature range and to have a miscibility with other liquid crystalline compounds as high as possible especially at low temperatures. Whereas many liquid crystalline compounds have already been known, there exists no substance at present which satisfies the conditions mentioned above by a single liquid crystalline compound, and thus several kinds of liquid crystalline compounds and further non-liquid crystalline compounds are mixed together and actually provided for practical uses at present.

Liquid crystalline compounds having chlorine atom as substituent for the purpose of improving characteristics of liquid crystal are known, for example, as follows:

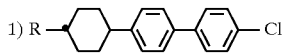
Japanese Patent Publication No. Sho 63-55496

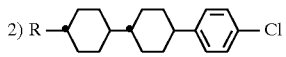
Japanese Patent Publication No. Sho 63-32051

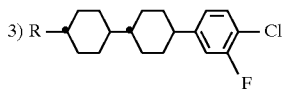
(WO 9015113)

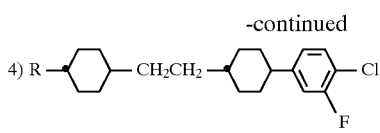
Japanese Patent Publication No. Hei 2-44818

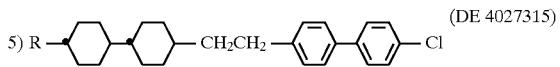
(DE 4027315)

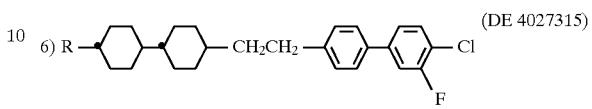
(DE 4027315)

Among these, compound 1) is not good in miscibility with known liquid crystalline compounds at low temperatures, and compounds 2), 3), and 4) are small in optical anisotropy. Whereas compounds 5) and 6) exhibit a liquid crystal phase at a comparatively wide temperature range, they are not good in miscibility with known liquid crystalline compounds at low temperatures as in the case of compound 1). Accordingly, these compounds are not satisfactory as liquid crystal material used for TFT mode.

DISCLOSURE OF THE INVENTION

An object of the present invention is to overcome the defects in the prior art mentioned above. Further object of the present invention is to provide a chlorobenzene derivative which can preferably be used for display devices of active matrix mode and has a four-ring structure containing chlorine atom as substituent; a liquid crystal composition comprising the derivative; and a liquid crystal display device comprising the composition.

In order to achieve the purpose mentioned above, the invention claimed by the present application is as follows:
(1) A liquid crystalline compound expressed by general formula (I)

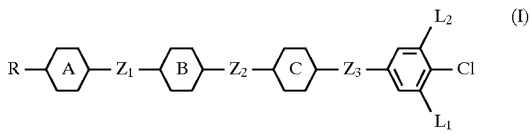

wherein ring A, ring B, and ring C independently represent trans-1,4-cyclohexylene group or 1,4-phenylene group, one or more hydrogen atoms on the six-membered ring of which may be replaced by halogen atoms, $Z_1$, $Z_2$, and $Z_3$ represent —$CH_2CH_2$— or single bond, respectively, provided that at least one of them represents —$CH_2CH_2$—, $L_1$ and $L_2$ represent H or halogen atom, and R represents an alkyl group or alkoxy group having 1 to 10 carbon atoms, provided that when $Z_1$ and $Z_3$ represent single bond and $Z_2$ represents —$CH_2CH_2$—, ring A represents 1,4-phenylene group, and when $Z_1$ and $Z_2$ represent single bond, and $Z_3$ represents —$CH_2CH_2$—, ring A represents trans-1,4-cyclohexylene group and ring C represents 1,4-cyclohexylene group at the same time.
(2) The liquid crystalline compound recited in (1) above wherein $Z_1$ represents —$CH_2CH_2$—, and $Z_2$ and $Z_3$ represent single bond.
(3) The liquid crystalline compound recited in (2) above wherein ring A and ring B represent cyclohexylene group.
(4) The liquid crystalline compound recited in (3) above wherein ring C represents monofluoro-1,4-phenylene group.
(5) The liquid crystalline compound recited in (4) above wherein $L_1$ represents fluorine atom.

(6) The liquid crystalline compound recited in (3) above wherein ring C represents difluoro-1,4-phenylene group.
(7) The liquid crystalline compound recited in (6) above wherein $L_1$ represent fluorine atom.
(8) The liquid crystalline compound recited in (1) above wherein $Z_2$ represents —$CH_2CH_2$—, and $Z_1$ and $Z_3$ represent single bond.
(9) The liquid crystalline compound recited in (1) above wherein $Z_1$ and $Z_2$ represent —$CH_2CH_2$—, and $Z_3$ represents single bond.
(10) The liquid crystalline compound recited in (1) above wherein $Z_1$ and $Z_3$ represent —$CH_2CH_2$—, and $Z_2$ represents single bond.
(11) The liquid crystalline compound recited in (1) above wherein $Z_2$ and $Z_3$ represent —$CH_2CH_2$—, and $Z_1$ represents single bond.
(12) The liquid crystalline compound recited in (1) above wherein all of $Z_1$, $Z_2$, and $Z_3$ represent —$CH_2CH_2$—.
(13) A liquid crystal composition comprising at least one liquid crystalline compound recited in any one of (1) through (12) above.
(14) A liquid crystal composition comprising, as a first component, at least one liquid crystalline compound recited in any one of (1) through (12) above, and comprising, as a second component, at least one compound selected from the group of compounds expressed by general formula (II), (III), or (IV)

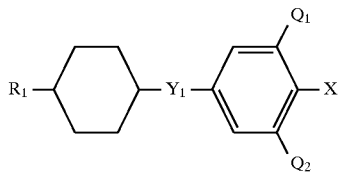
(II)

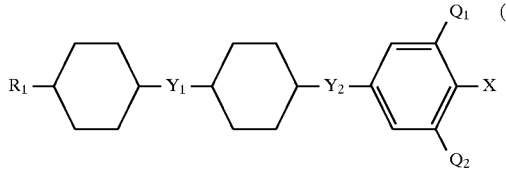
(III)

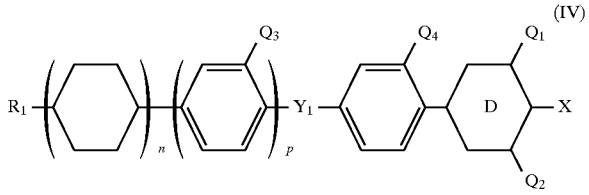
(IV)

wherein $R_1$ represents an alkyl group having 1 to 10 carbon atoms, X represents F, Cl, $CF_3$, $OCF_3$, $OCF_2H$, or an alkyl group having 1 to 10 carbon atoms, $Q_1$, $Q_2$, $Q_3$, and $Q_4$ independently represent H or F, n is 1 or 2, p is 0 or 1, $Y_1$ and $Y_2$ independently represent —$CH_2CH_2$—, —CH=CH—, or single bond, and ring D represents trans-1,4-cyclohexylene group or 1,4-phenylene group.

(15) A liquid crystal composition comprising, as a first component, at least one liquid crystalline compound recited in any one of (1) through (12) above, and comprising, as a second component, at least one compound selected from the group of compounds expressed by general formula (V), (VI), (VII), (VIII), or (IX)

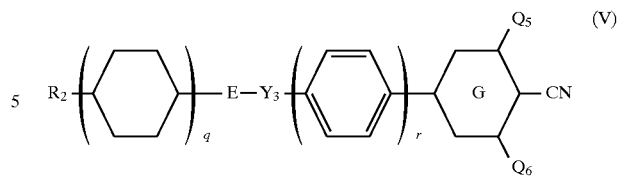
(V)

wherein $R_2$ represents F, an alkyl group having 1 to 10 carbon atoms, or an alkenyl group having 2 to 10 carbon atoms, any methylene group (—$CH_2$—) in which alkyl group or alkenyl group may be replaced by oxygen atom (—O—) provided that in no case are two or more adjacent methylene groups replaced by oxygen atom, $Y_3$ represents —$CH_2CH_2$—, —COO—, or single bond, $Q_5$ and $Q_6$ independently represent H or F, E represents trans-1,4-cyclohexylene group, 1,4-phenylene group, or trans-1,3-dioxane-2,5-diyl group, ring G represents trans-1,4-cyclohexylene group or 1,4-phenylene group, and q and r are independently 0 or 1,

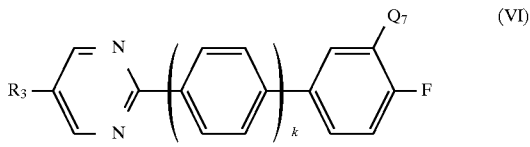
(VI)

wherein $R_3$ represents an alkyl group having 1 to 10 carbon atoms, $Q_7$ represents H or F, and k is 0 or 1,

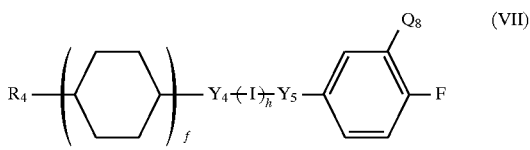
(VII)

wherein $R_4$ represents an alkyl group having 1 to 10 carbon atoms, I represents trans-1,4-cyclohexylene group or 1,4-phenylene group, $Q_8$ represents H or F, $Y_4$ represents —COO— or single bond, $Y_5$ represents —COO— or —C≡C—, and f and h are independently 0 or 1,

(VIII)

wherein $R_5$ and $R_6$ independently represent an alkyl group, alkoxy group, or alkoxymethyl group having 1 to 10 carbon atoms, J represents trans-1,4-cyclohexylene group, 1,3-pyrimidine-2,5-diyl group, or 1,4-phenylene group, K represents trans-1,4-cyclohexylene group or 1,4-phenylene group, and $Y_6$ represents —C≡C—, —COO—, —$CH_2CH_2$—, or single bond,

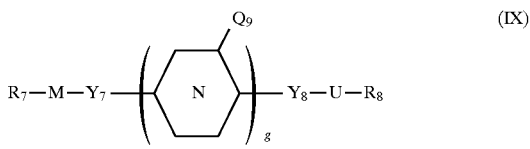
(IX)

wherein $R_7$ represents an alkyl group or alkoxy group having 1 to 10 carbon atoms, $R_8$ represents an alkyl group having 1 to 10 carbon atoms, any methylene group (—$CH_2$—) in $R_8$ may be replaced by oxygen atom (—O—) provided that in no case are two or more adjacent methylene groups replaced by oxygen atom, M represents trans-1,4-cyclohexylene group or 1,3-pyrimidine-2,5-diyl group, each of ring N and U independently represent trans-1,4-cyclohexylene group or 1,4-phenylene group, $Y_7$ represents —$CH_2CH_2$—, —COO—, or single bond, $Y_8$ represents —C≡C—, —COO—, or single bond, g is 0 or 1, and $Q_9$ represents H or F.

(16) A liquid crystal composition comprising, as a first component, at least one liquid crystalline compound recited in any one of (1) through (12) above, comprising, as a second component, at least one liquid crystalline compound selected from the group of compounds expressed by general formula (II), (III), or (IV), and comprising, as the other part of the second component, at least one liquid crystalline compound selected from the group of compounds expressed by general formula (V), (VI), (VII), (VIII), or (IX).

(17) A liquid crystal display device comprising any one of liquid crystal composition recited in any one of (13) through (16) above.

BEST MODE FOR CARRYING OUT THE INVENTION

Since the liquid crystalline compounds of the present invention expressed by general formula (I) fall under four-ring compound having a benzene ring substituted with chlorine atom, the present compounds are similar to the compounds shown in DE 4027315 mentioned above when both $Z_1$ and $Z_2$ are covalent bond, and $Z_3$ is —$CH_2CH_2$—. However, the compounds of DE '315 and the present compounds are structurally different from each other in the point that whereas the former compounds have trans-1,4-cyclohexylene group as the ring at one end, the present compounds have 1,4-phenylene group when —$CH_2CH_2$— exists in the same center portion as in the former compounds. Besides, even when compared from the viewpoint of physical property, the compounds of the present invention have a characteristic of being excellent in miscibility with existing liquid crystalline compounds at low temperatures. Further, the compounds of the present invention are physically and chemically stable to a sufficient extent under the conditions where display devices are generally used, and can be derived into compounds having desired physical properties by properly selecting six-membered rings, substituents, and bonding groups of constituent elements in a molecule. Accordingly, new liquid crystal compositions having preferable characteristics can be provided when the compounds of the present invention are used as component of liquid crystal compositions.

Compounds of the present invention expressed by general formula (I) are divided broadly into groups expressed by one of formulas (Ia) to (If).

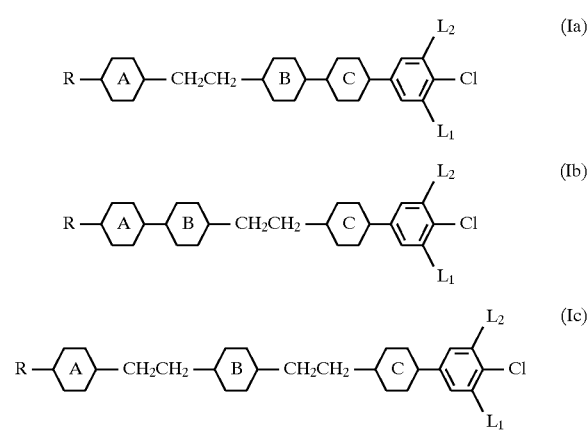

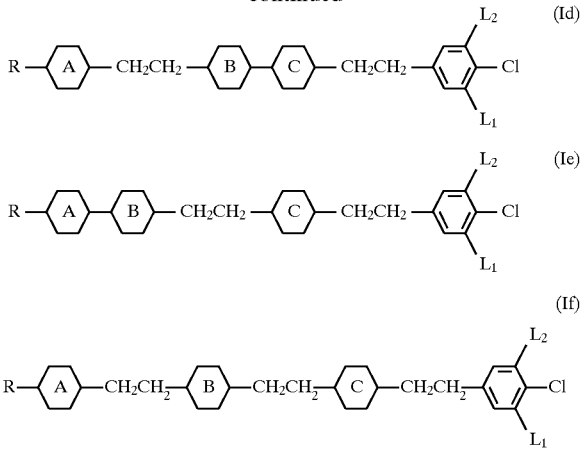

wherein ring A, ring B, ring C, R, $L_1$, and $L_2$ have the same meaning as mentioned above.

Among these compounds, compounds expressed by formula (Ia) are especially preferable in achieving the purpose of the present invention. Further, the compounds expressed by formula (Ia) are developed into those expressed by any one of the formulas (Iaa) to (Ial), (Ib) into (Iba) to (Ibk), (Ic) into (Ica) to (Ick), (Id) into (Ida) to (Idk), (Ie) into (Iea) to (Iel), and (If) are developed into (Ifa) to (Ifk), respectively.

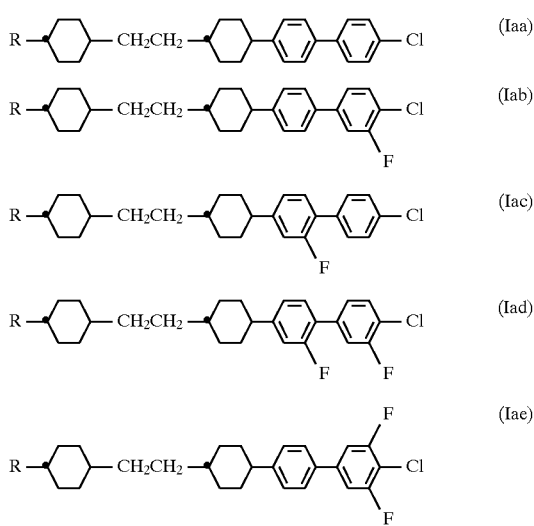

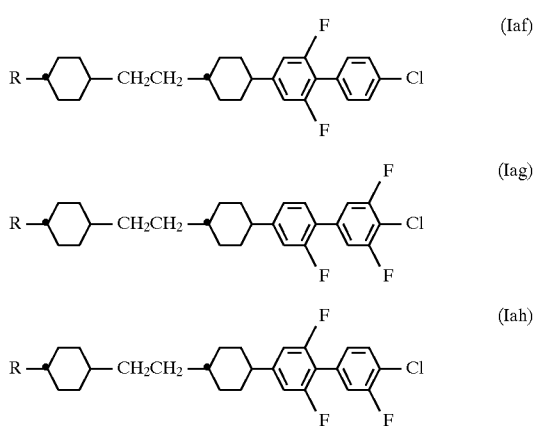

-continued
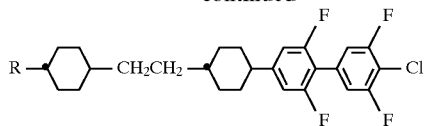 (Iai)
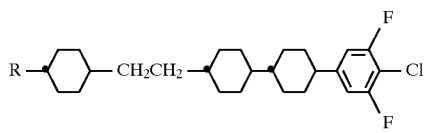 (Iaj)
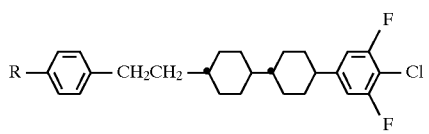 (Iak)
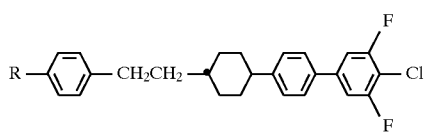 (Ial)
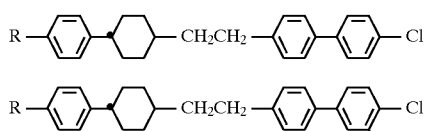 (Iba)
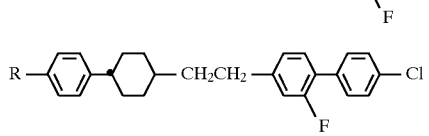 (Ibb)
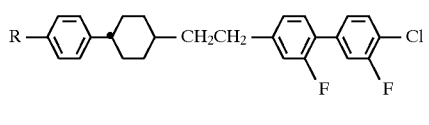 (Ibc)
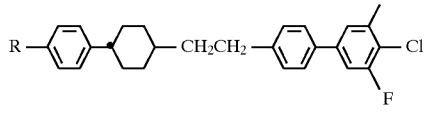 (Ibd)
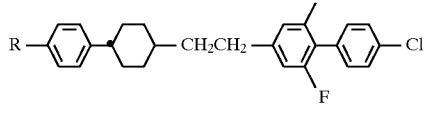 (Ibe)
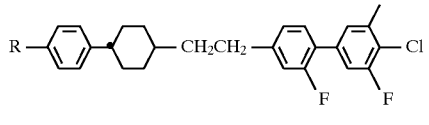 (Ibf)
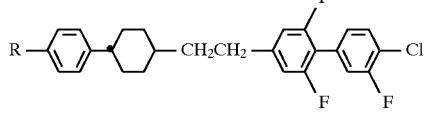 (Ibg)
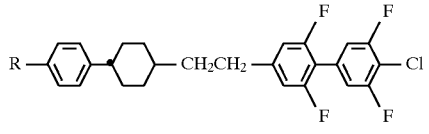 (Ibh)
 (Ibi)
-continued
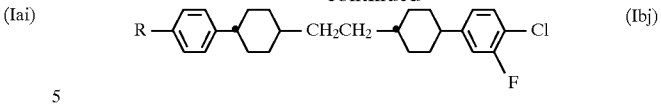 (Ibj)
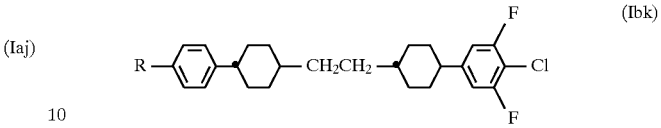 (Ibk)
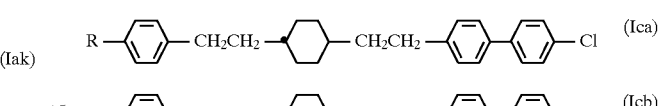 (Ica)
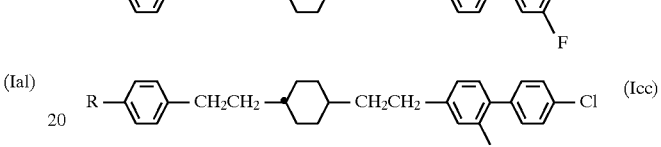 (Icb)
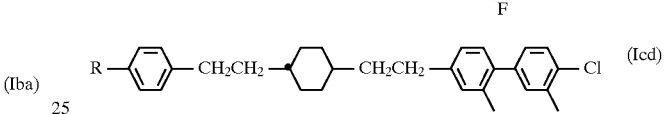 (Icc)
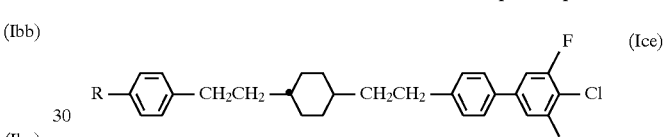 (Icd)
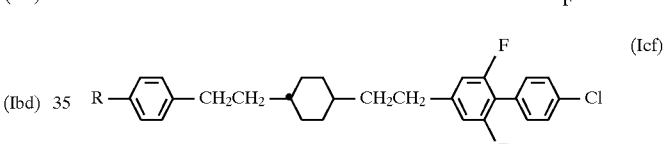 (Ice)
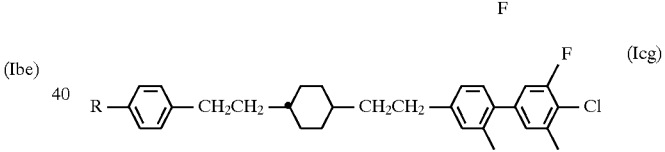 (Icf)
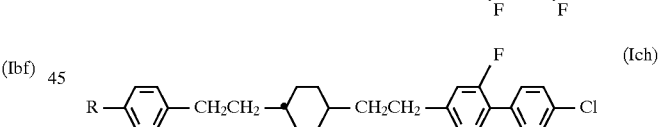 (Icg)
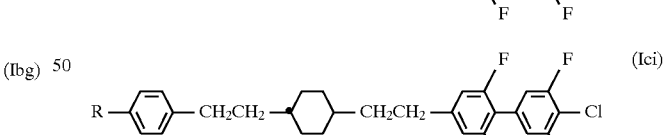 (Ich)
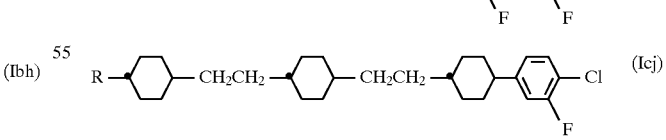 (Ici)
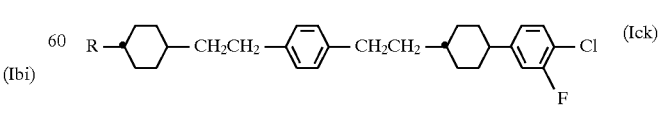 (Icj)
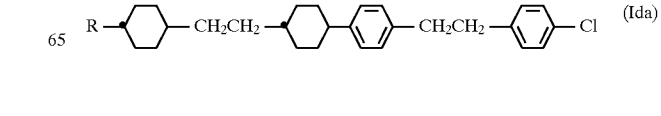 (Ick)
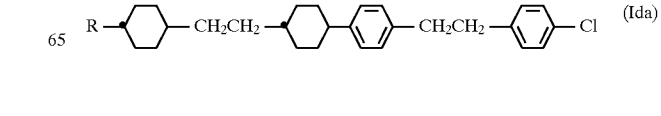 (Ida)

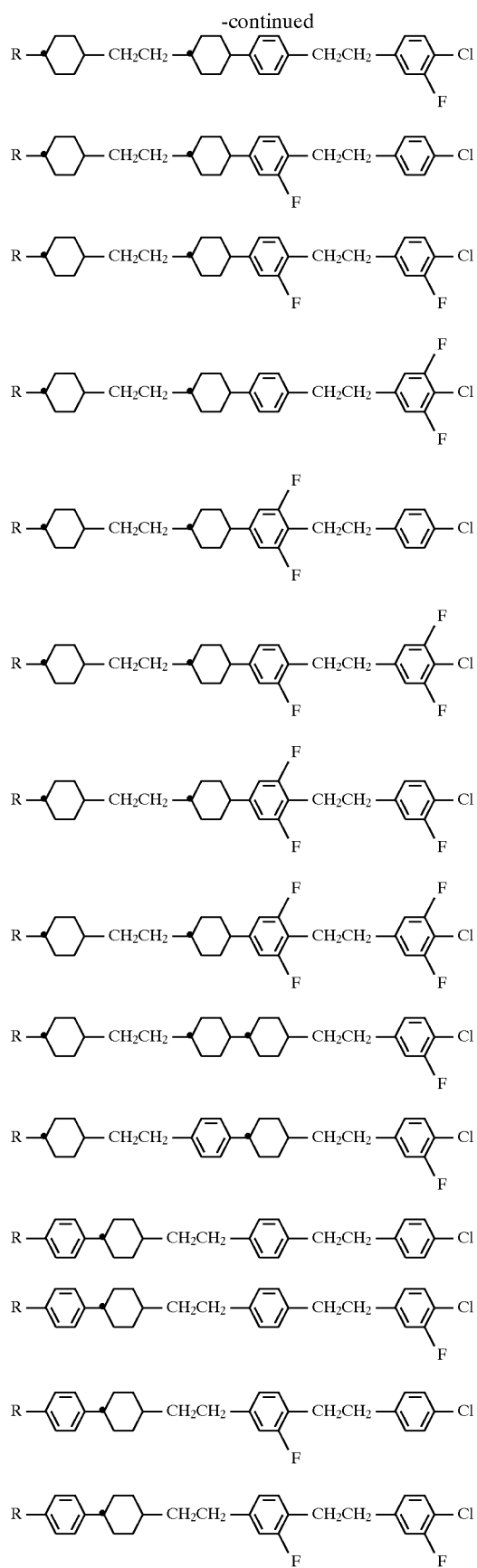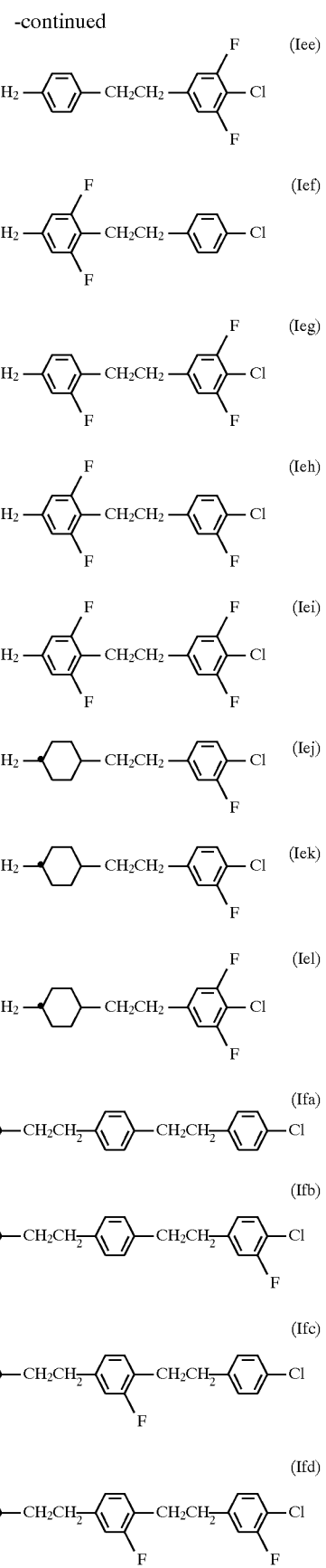

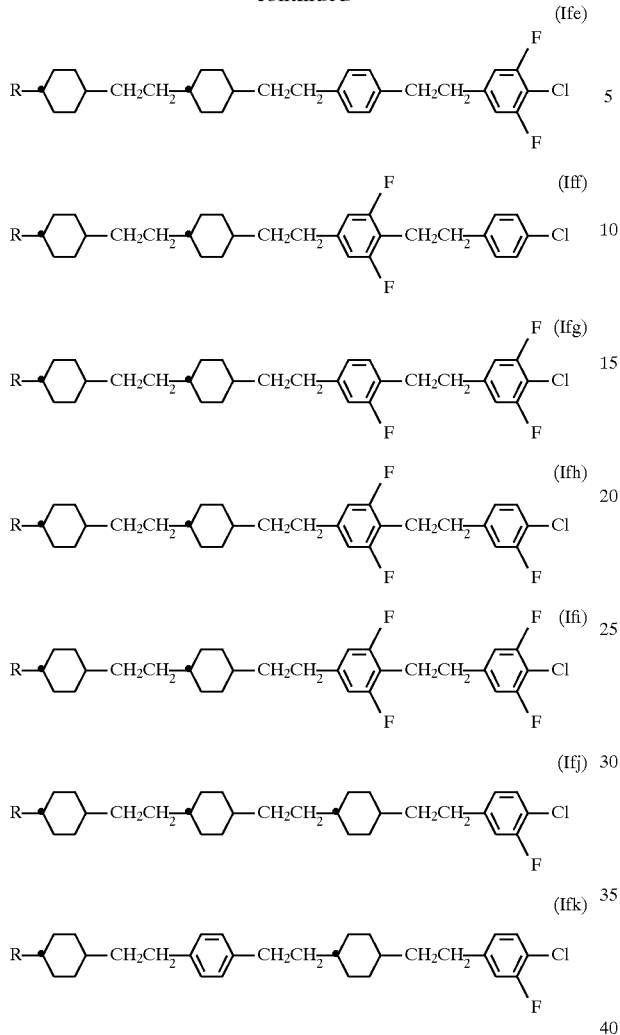

Among the compounds mentioned above, compounds expressed by formula (Iab), (Iac), (Iad), (Iaf), or (Iah) are particularly preferable since they have a large dielectric anisotropy.

Among the liquid crystalline compounds of the present invention expressed by general formula (I), compounds expressed by any one of the formulas (Ia) to (Ic) can preferably be produced, for example, according to the following process:

Synthesis of (Ia) to (Ic):

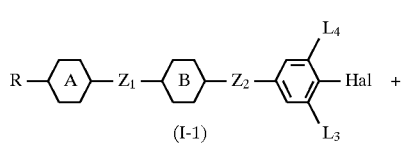

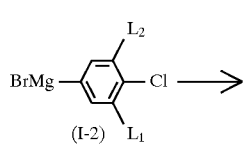

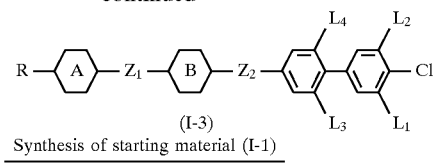

Synthesis of starting material (I-1)

Case of (Ia):

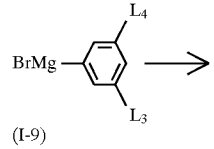

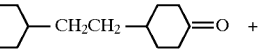

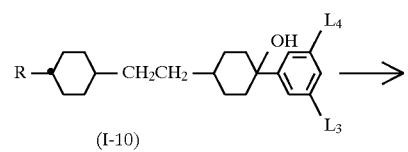

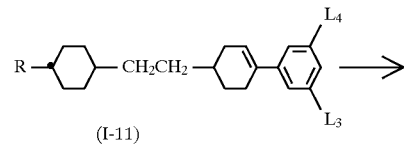

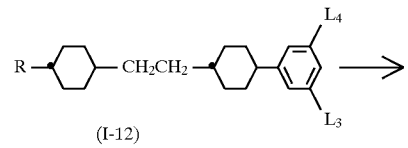

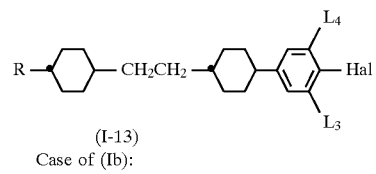

Case of (Ib):

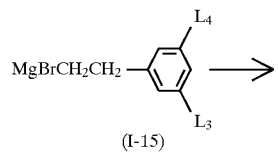

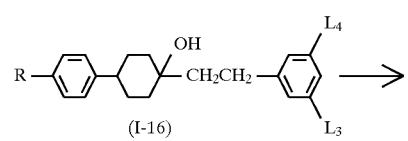

-continued

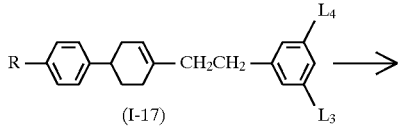
(I-17)

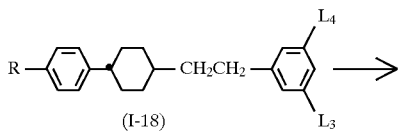
(I-18)

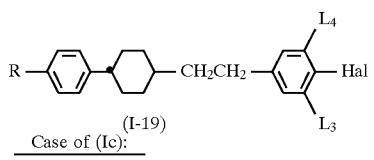
(I-19)

Case of (Ic):

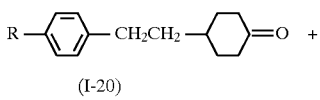
(I-20)

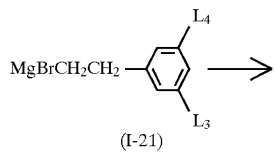
(I-21)

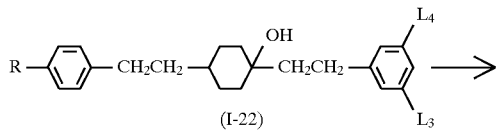
(I-22)

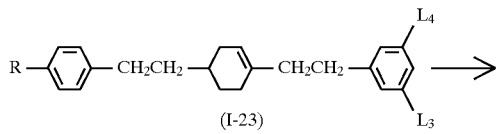
(I-23)

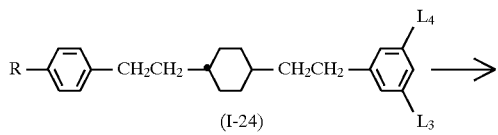
(I-24)

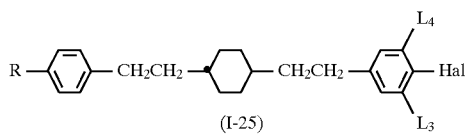
(I-25)

That is, Compound (I-3) as example of compounds of general formula (I) can be produced by subjecting Grignard reagent (I-2) (wherein $L_3$ and $L_4$ represent H or halogen atom) and halogenobenzene derivative (I-1) as example of three-ring compound to a cross coupling reaction (Synthesis, 317 (1985)) in the presence of a proper catalyst. Compounds expressed by formula (I-1) mentioned above as example of starting materials can be produced by various methods typified by the following:

That is, a cyclohexanone derivative [(I-8) in the case of (Ia), (I-14) in the case of (Ib), and (I-20) in the case of (Ic)] and Grignard reagent of a bromobenzene derivative [(I-9) in the case of (Ia), (I-15) in the case of (Ib), and (I-21) in the case of (Ic)] are reacted (Pure and Applied Chemistry 52, 545 (1980)), respectively, to form an alcohol having a three-ring structure [(I-10) in the case of (Ia), (I-16) in the case of (Ib), and (I-22) in the case of (Ic)], subjecting the alcohol to a dehydrating reaction and a reducing reaction, and then directly halogenate the benzene derivative thus obtained [(I-12) in the case of (Ia), (I-18) in the case of (Ib), and (I-24) in the case of (Ic)] to produce (I-13) in the case of (Ia), (I-19) in the case of (Ib), or (I-25) in the case of (Ic). This reaction is preferably conducted generally in a solvent of ether type such as diethyl ether and tetrahydrofuran at a temperature within the range of 0° C. to 100° C. As the catalyst to be used, a nickel-phosphine type catalyst and palladium chloride type catalyst are preferable.

Among the liquid crystalline compounds of the present invention expressed by general formula (I), compounds expressed by any one of the formulas (Id) to (If) can preferably be produced, for example, according to the following process:

Synthesis of (Id) to (If):

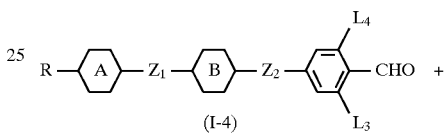
(I-4)

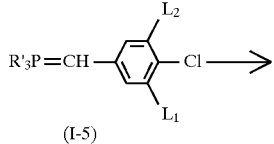
(I-5)

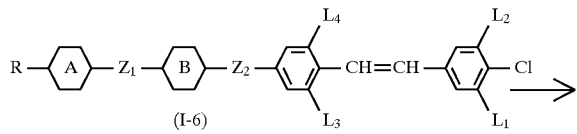
(I-6)

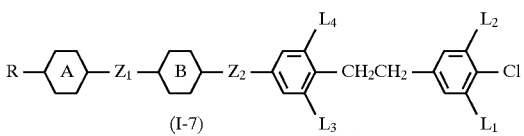
(I-7)

Synthesis of starting material (I-4)

Case of (Id):

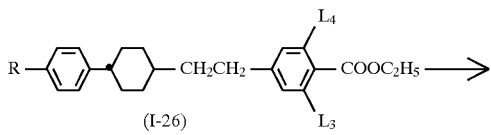
(I-26)

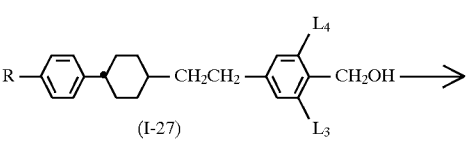
(I-27)

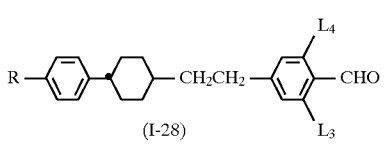
(I-28)

-continued

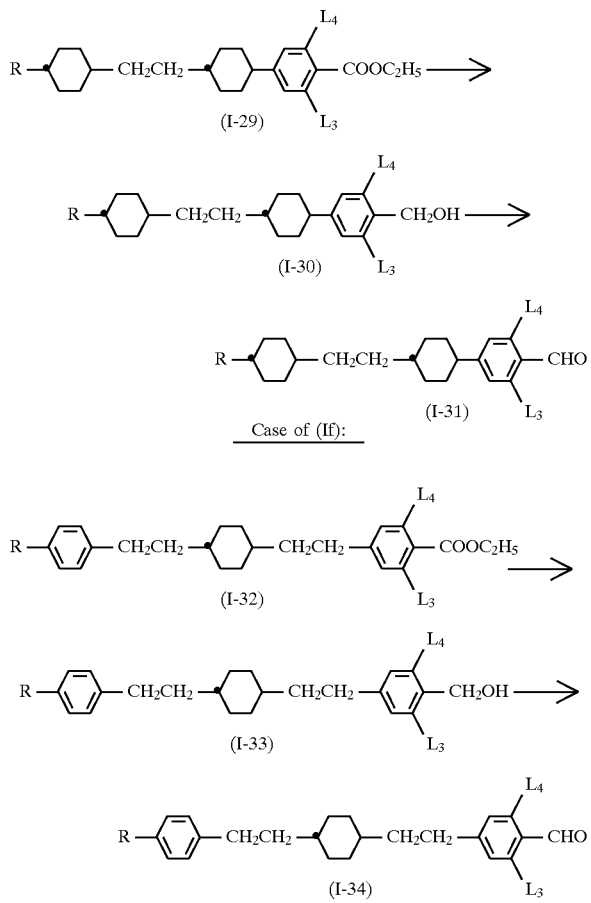

That is, an aldehyde derivative (I-4) derived from the compound expressed by the formula (I-1) mentioned above by a known method (reference is made to a description below) and a phosphorous ylide compound expressed by formula (I-5) are subjected to a Wittig reaction (Organic Reaction Vol. 14, 270 (1965)) to form Compound (I-6), and then reducing the Compound (I-6) to produce Compound (I-7). Phosphorous ylide compound (I-5) mentioned above can be obtained by reacting a phosphonium salt with an appropriate base, for example, potassium-t-butoxide, sodium methoxide, n-butyl lithium, or sodium hydride. All of these reactions are generally carried out in an organic solvent. As the organic solvent, ones which do not impede the reaction are satisfactorily used, and an ether type solvent such as diethyl ether and tetrahydrofuran can preferably the mentioned. While the temperature at the time of the reaction is suitably in the range of from −50° C. to the boiling point of the solvent to be used, it is preferably between −30° C. to room temperature in particular.

Aldehyde derivatives shown by the formula (I-4) mentioned above as example of starting materials can be produced, for example, by various methods typified by the one mentioned below:

That is, a halogenobenzene derivative expressed by the formula (I-1) is reacted with n-butyl lithium to form a lithium salt, and the salt is reacted with carbon dioxide to obtain a carboxylic acid derivative [(I-26) in the case of (Id), (I-29) in the case of (Ie), and (I-32) in the case of (If)]. Subsequently, the acid derivative is reacted with a metal hydride such as lithium aluminum hydride and boron sodium hydride to form an alcohol derivative [(I-27) in the case of (Id), (I-30) in the case of (Ie), and (I-33) in the case of (If)], and then the alcohol derivative is subjected to an oxidation treatment by a known method to produce (I-28) in the case of (Id), (I-31) in the case of (Ie), or (I-34) in the case of (If).

Since all of the liquid crystalline compounds (I) of the present invention obtained by such methods exhibit a large optical anisotropy (Δn), are readily mixed with various liquid crystal materials, and are excellent in miscibility even at low temperatures, the compounds (I) are extremely excellent as component which constitute nematic liquid crystal compositions, particularly liquid crystal compositions for display devices of active matrix mode typified by TFT mode.

While the liquid crystal compositions provided by the present invention may comprise only a first component comprising at least one liquid crystalline compound expressed by general formula (I), the compositions preferably comprise, as a second component, at least one compound selected from the group of compounds expressed by general formula (II), (III), or (IV) mentioned above (hereinafter referred to as second A component) and/or at least one compound selected from the group of compounds expressed by general formula (V), (VI), (VII), (VIII), or (IX) mentioned above (hereinafter referred to as second B component) in addition to the first component; and further, known compounds can be mixed as a third component for the purpose of adjusting threshold voltage, temperature range of liquid crystal phase, optical anisotropy, dielectric anisotropy, and viscosity.

Among the second A component mentioned above, the following (II-1) to (II-15) can be mentioned as preferable examples of compounds included in general formula (II), (III-1) to (III-48) as preferable examples included in general formula (III), and (IV-1) to (IV-41) can be mentioned as preferable examples included in general formula (IV), respectively:

 (II-1)

 (II-2)

 (II-3)

 (II-4)

 (II-5)

 (II-6)

-continued
 (II-7)
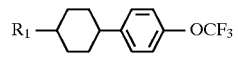 (II-8)
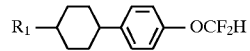 (II-9)
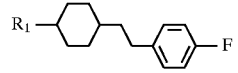 (II-10)
 (II-11)
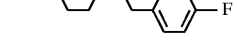 (II-12)
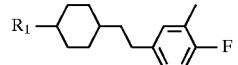 (II-13)
 (II-14)
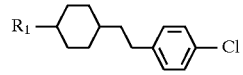 (II-15)
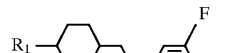 (III-1)
 (III-2)
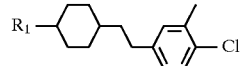 (III-3)
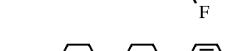 (III-4)
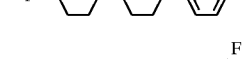 (III-5)
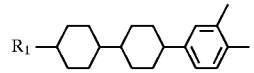 (III-6)
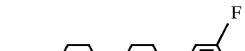 (III-7)
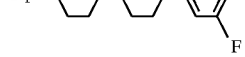 (III-8)
-continued
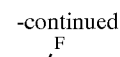 (III-9)
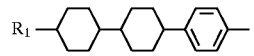 (III-10)
 (III-11)
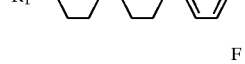 (III-12)
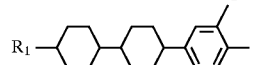 (III-13)
 (III-14)
 (III-15)
(III-16)
(III-17)
(III-18)
(III-19)
(III-20)
(III-21)
(III-22)
(III-23)

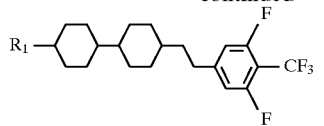 (III-24)
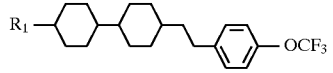 (III-25)
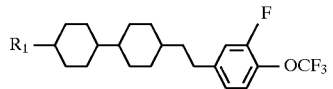 (III-26)
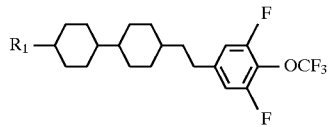 (III-27)
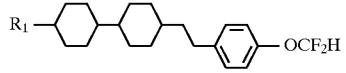 (III-28)
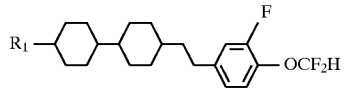 (III-29)
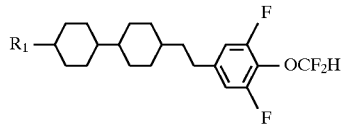 (III-30)
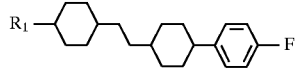 (III-31)
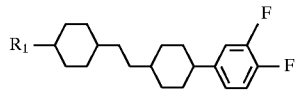 (III-32)
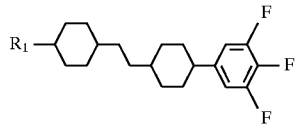 (III-33)
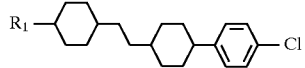 (III-34)
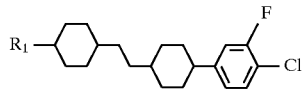 (III-35)
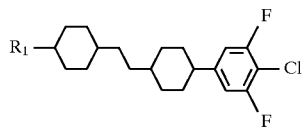 (III-36)
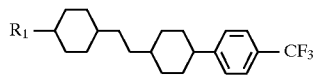 (III-37)
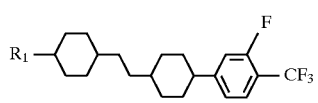 (III-38)
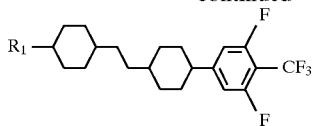 (III-39)
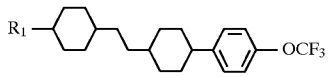 (III-40)
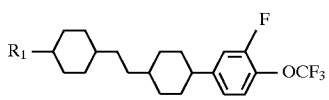 (III-41)
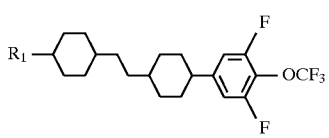 (III-42)
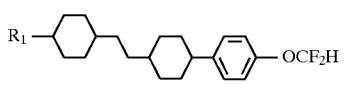 (III-43)
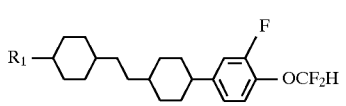 (III-44)
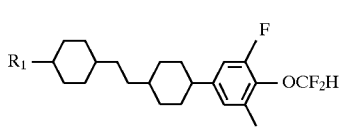 (III-45)
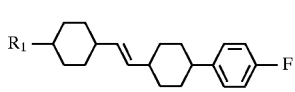 (III-46)
 (III-47)
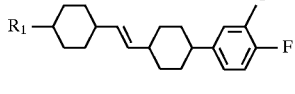 (III-48)
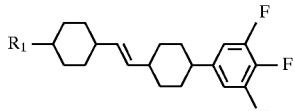 (IV-1)
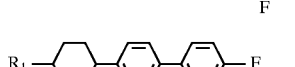 (IV-2)
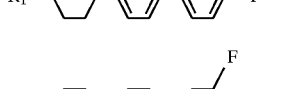 (IV-3)
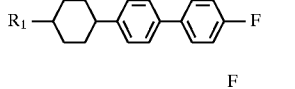 (IV-4)
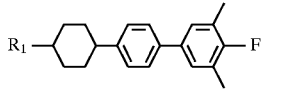 (IV-5)

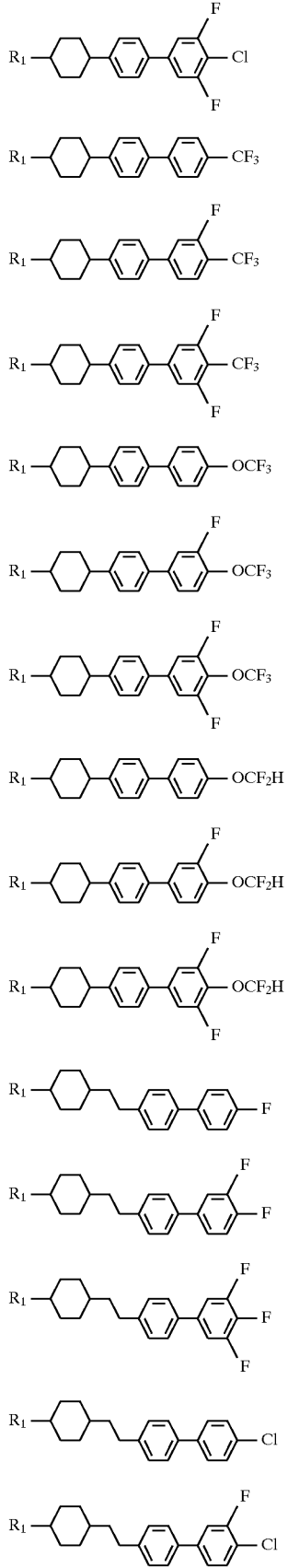
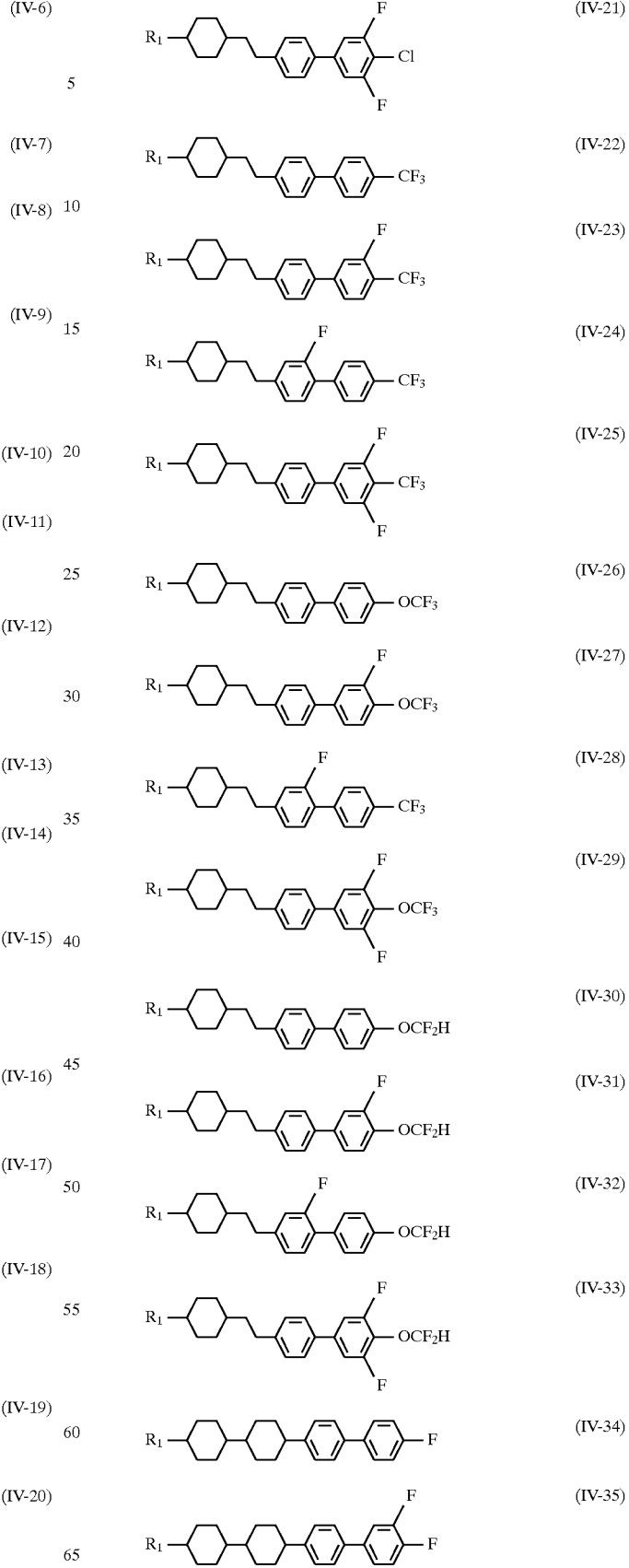

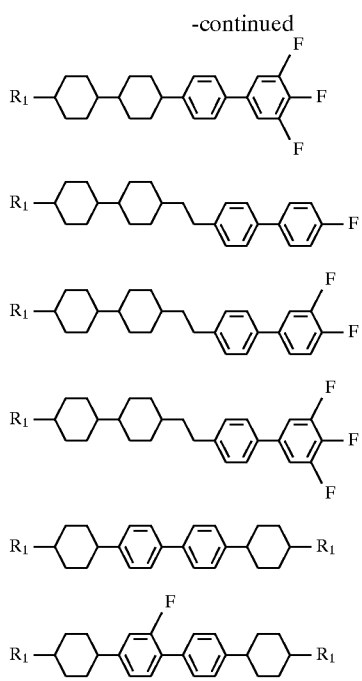

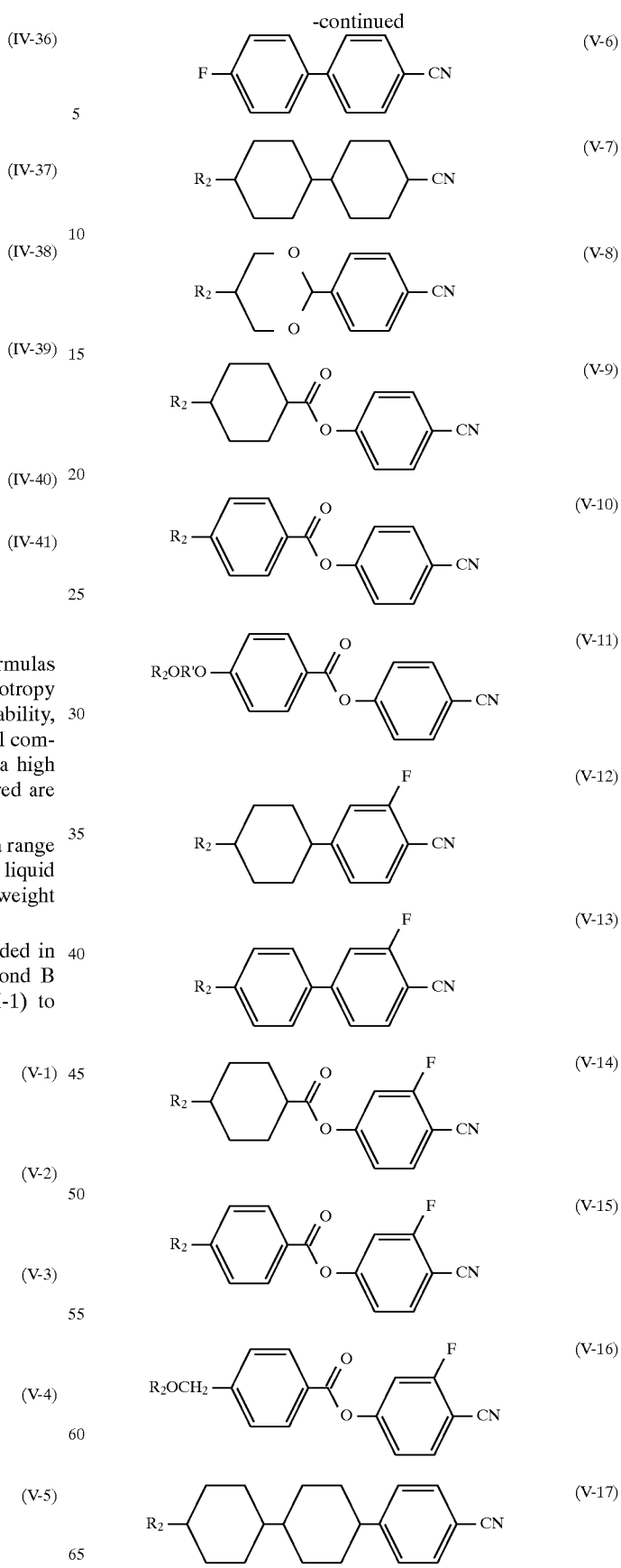

Since the compounds expressed by these general formulas (II) to (IV) exhibit a positive value of dielectric anisotropy and besides are remarkably excellent in thermal stability, they are indispensable compounds when liquid crystal compositions for AM-LCD (TFT) of which particularly a high voltage holding ratio and a high reliability are required are produced.

Amount of the compounds to be used is suitably in a range of 1 to 99% by weight based on the total weight of liquid crystal composition. Preferably, it is 10 to 97% by weight and more desirably 40 to 95% by weight.

Next, as preferable examples of compounds included in general formula (V), (VI), or (VII) among the second B component mentioned above, (V-1) to (V-27), (VI-1) to (VI-3), and (VII-1) to (VII-11) can be mentioned.

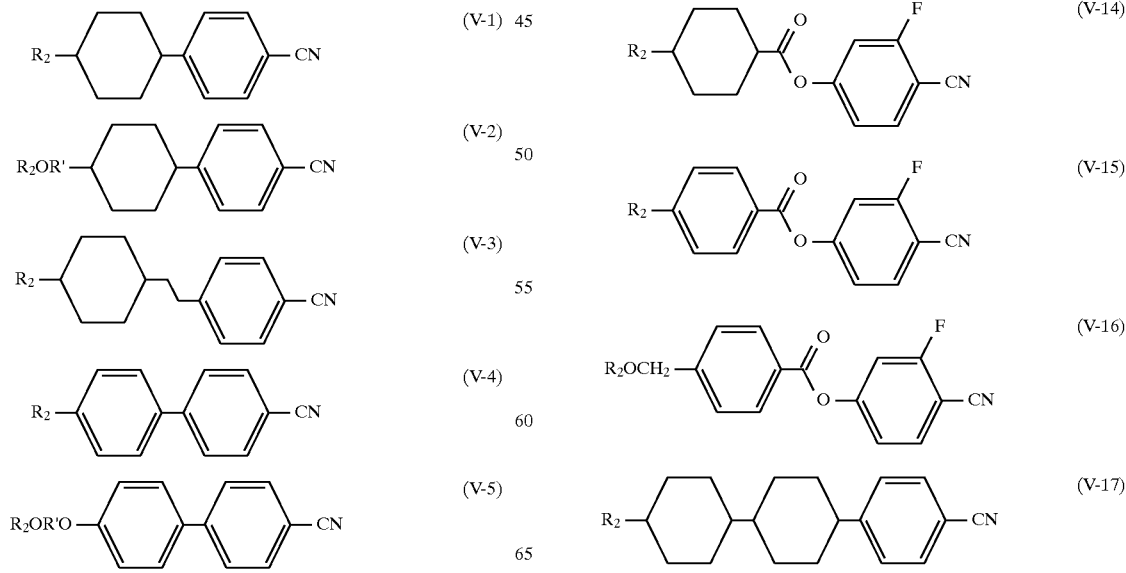

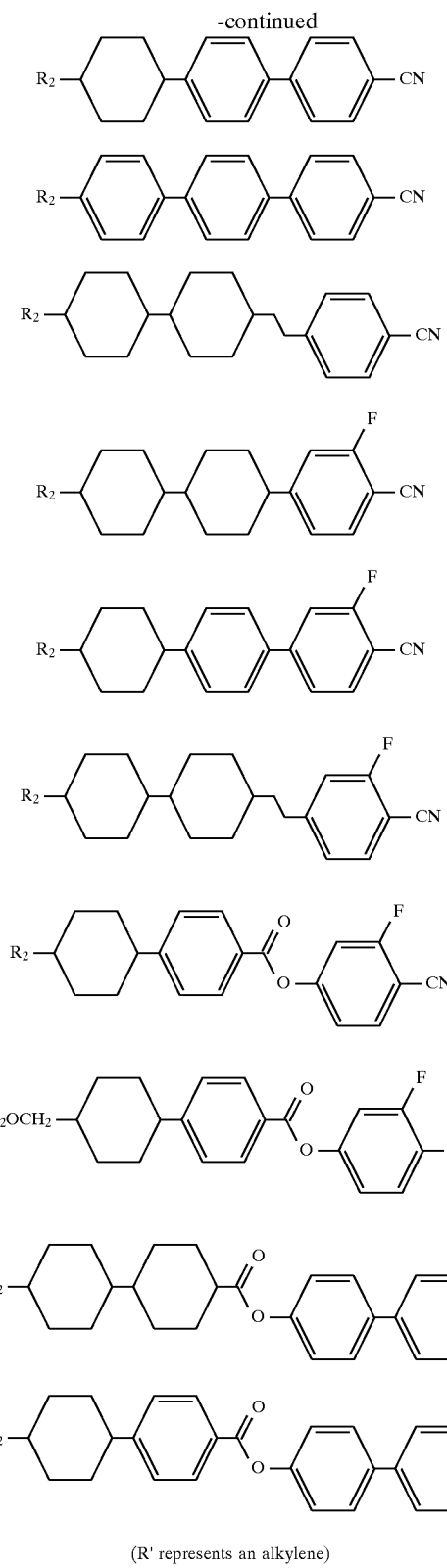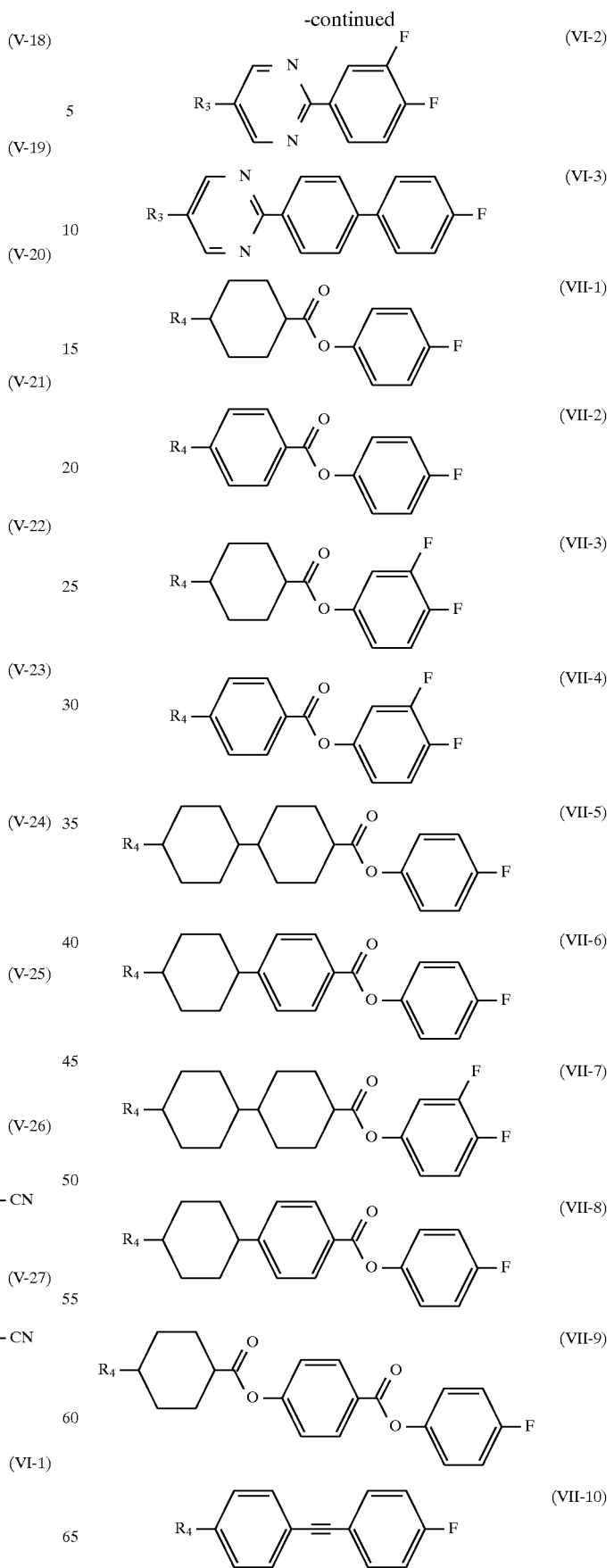

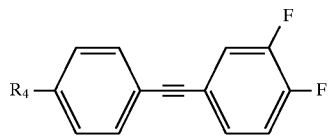
(VII-11)

Compounds expressed by general formula (V) to (VII) have a large positive value of dielectric anisotropy and are used as component of liquid crystal compositions particularly for the purpose of reducing threshold voltage. They are used also for the purpose of viscosity adjustment, Δn adjustment, and widening temperature range of nematic phase such as raising clearing point, and for the purpose of improving steepness.

As preferable examples of the compounds included in general formula (VIII) or (IX) among the compounds of the second B component, (VIII-1) to (VIII-15) and (IX-1) to (IX-14) can be mentioned.

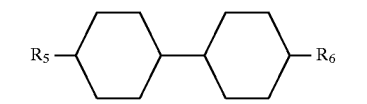
(VIII-1)

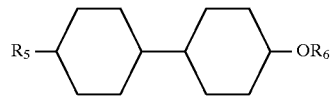
(VIII-2)

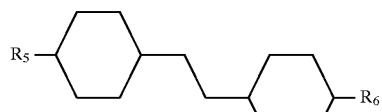
(VIII-3)

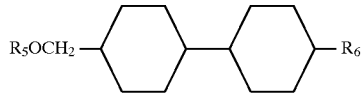
(VIII-4)

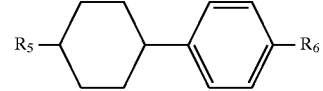
(VIII-5)

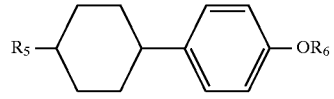
(VIII-6)

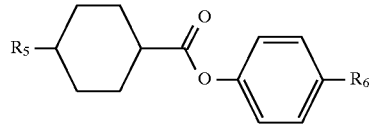
(VIII-7)

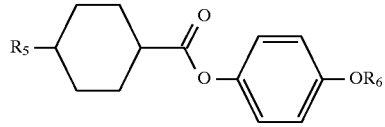
(VIII-8)

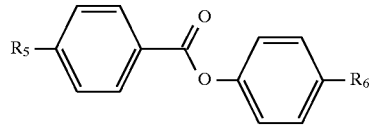
(VIII-9)

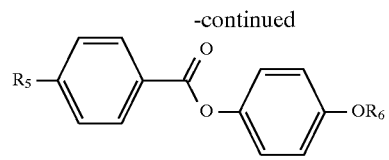
(VIII-10)

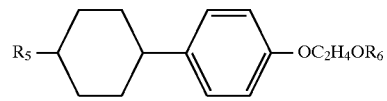
(VIII-11)

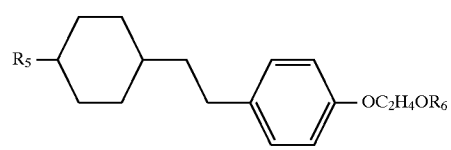
(VIII-12)

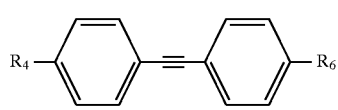
(VIII-13)

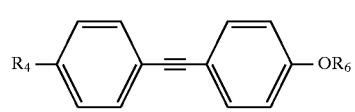
(VIII-14)

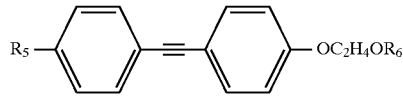
(VIII-15)

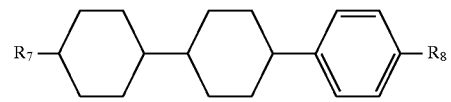
(IX-1)

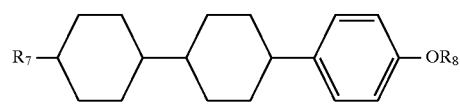
(IX-2)

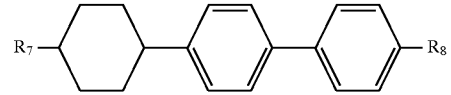
(IX-3)

(IX-4)

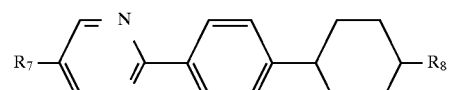
(IX-5)

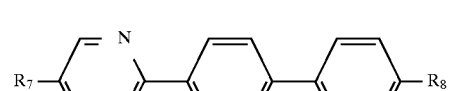
(IX-6)

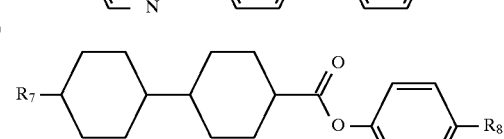
(IX-7)

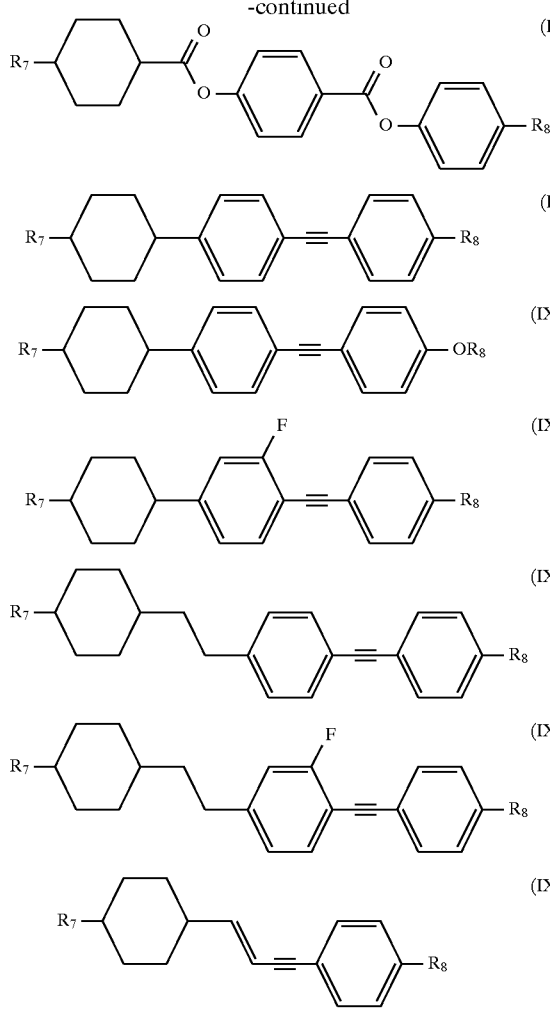

Compounds expressed by general formula (VIII) or (IX) have a negative or small positive value of dielectric anisotropy. Among the compounds, the compounds expressed by general formula (VIII) are used as component of liquid crystal compositions principally for the purpose of decreasing viscosity and adjusting Δn, and the compounds expressed by general formula (IX) are used for the purpose of widening nematic range such as raising clearing point and for the purpose of adjusting Δn.

Compounds expressed by any one of general formulas (V) to (IX) are indispensable when liquid crystal compositions particularly for STN type display mode and TN type display mode are produced.

Amount of the compounds to be used is suitably in a range of 1 to 99% by weight based on the total weight of liquid crystal composition when liquid crystal compositions for ordinary TN type display mode or STN type display mode are produced. Preferably it is 10 to 97% by weight and more desirably 40 to 95% by weight.

As mentioned above, while the liquid crystal compositions for TFT are satisfactorily composed of the first component and the second A component, the compositions may further comprise the second B component as a part of the compositions. Also, while the liquid crystal compositions for STN or TN are satisfactorily composed of the first component and the second B component, the compositions may comprise the second A component as a part of the compositions in addition to the first and second B components.

Liquid crystal compositions provided according to the present invention preferably comprise at least one crystalline compound expressed by general formula (I) in an amount of 0.1 to 99% by weight to develop excellent characteristics. The liquid crystal compositions are generally produced by methods which are conventional by themselves, for example, by a method wherein several components are dissolved in each other at a high temperature. Also, the liquid crystal compositions of the present invention are improved, depending on intended applications, by adding appropriate additives, if necessary, and optimized. Such additives are well known in the art and described in literatures in detail. Generally, a chiral dopant or the like are added to cause a helical structure of liquid crystal to adjust a required twisted angle and to avoid reverse-twist.

Further, the liquid crystal compositions of the present invention can be used as liquid crystal composition for guest-host (GH) mode by including therein a dichroic dye such as merocyanine type, styryl type, azo type, azomethine type, azoxy type, quinophthalone type, anthraquinone type, and tetrazine type. Still further, they can also be used as liquid crystal composition for polymer dispersion type liquid crystal display device (PDLCD) typified by NCAP which is prepared by forming a nematic liquid crystal into a microcapsule or typified by a polymer network liquid crystal display device (PNLCD) which is prepared by forming a polymer of a three-dimensional network structure in a liquid crystal. Also, the liquid crystal compositions of the present invention can be used for electrically controlled birefringence (ECB) mode or dynamic scattering (DS) mode.

As the nematic liquid crystal compositions comprising the compound of the present invention, the following can be mentioned, in which the number of compounds (shown in parentheses) is the same as that shown in Examples described below:

COMPOSITION EXAMPLE 1

-continued
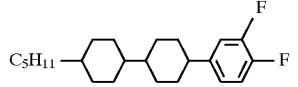 10%
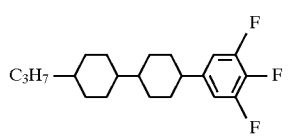 6%
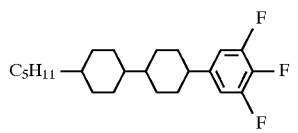 4%
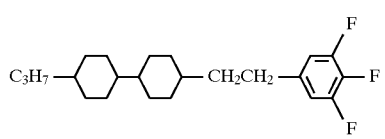 10%
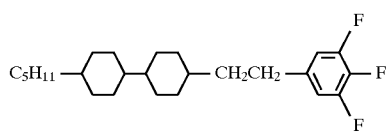 10%
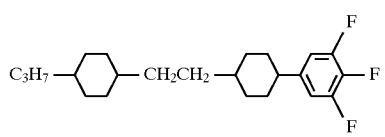 5%
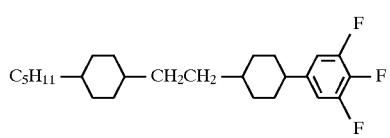 5%
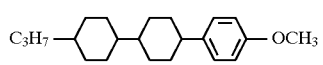 6%
COMPOSITION EXAMPLE 2
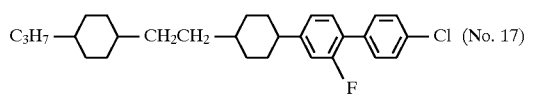 (No. 17) 5%
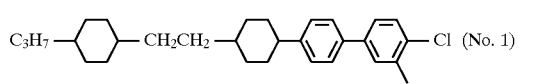 (No. 1) 5%
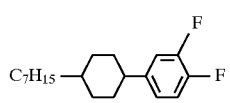 5%
 5%
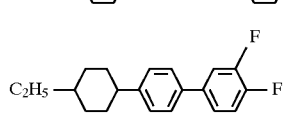 5%
-continued
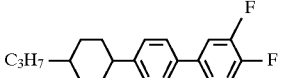 5%
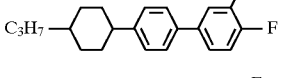 10%
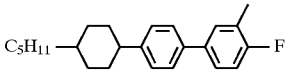 8%
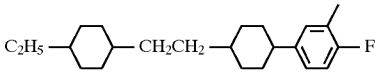 4%
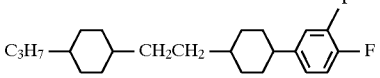 8%
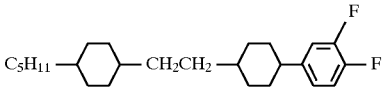 7%
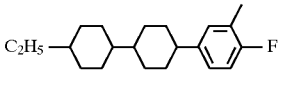 7%
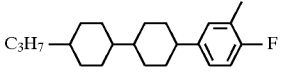 7%
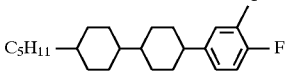 4%
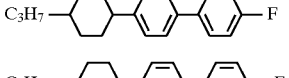 4%
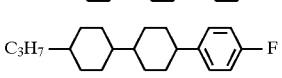 3%
 4%
 4%
| | |
|---|---|
| Cp (°C.) | 110.4 |
| (ηcP) | 26.1 |
| Δn | 0.107 |
| Δε | 4.7 |
| Vth | 2.37 |
COMPOSITION EXAMPLE 3
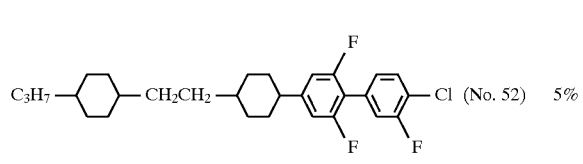 (No. 52) 5%
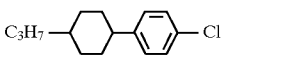 5%
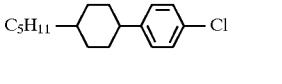 5%

-continued
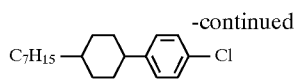 5%
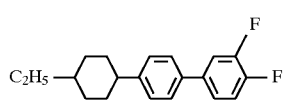 10%
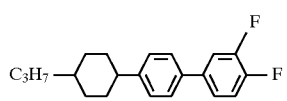 10%
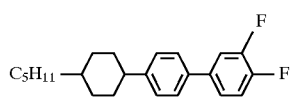 10%
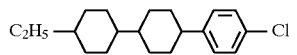 5%
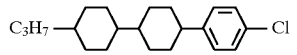 5%
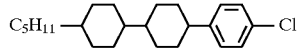 5%
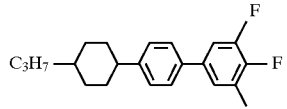 7%
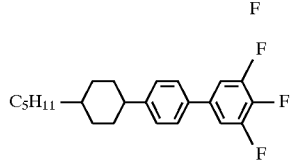 7%
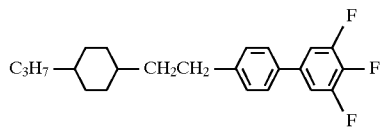 7%
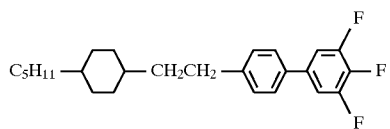 7%
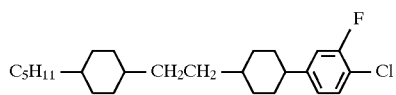 4%
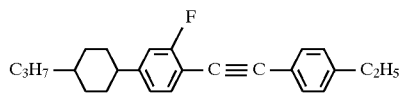 3%
| | |
|---|---|
| Cp (°C.) | 90.2 |
| (ηcP) | 25.0 |
| Δn | 0.129 |
| Δε | 6.2 |
| Vth | 2.14 |
COMPOSITION EXAMPLE 4
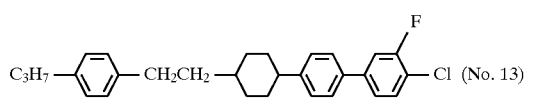 5%
-continued
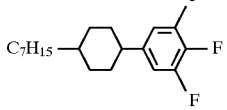 5%
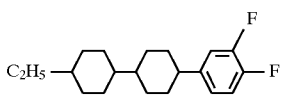 10%
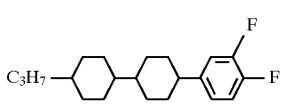 10%
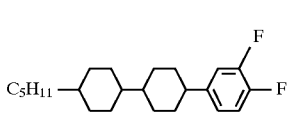 10%
 8%
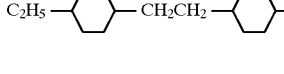 4%
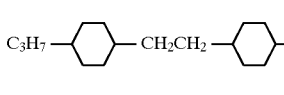 8%
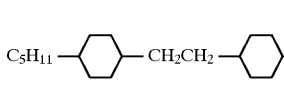 6%
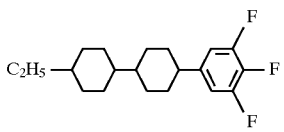 6%
 5%
 5%
 5%
 5%
 5%
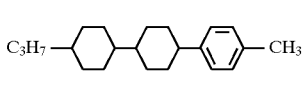 4%
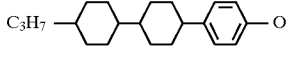 4%

COMPOSITION EXAMPLE 5
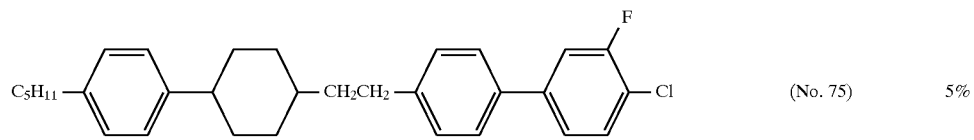 (No. 75) 5%
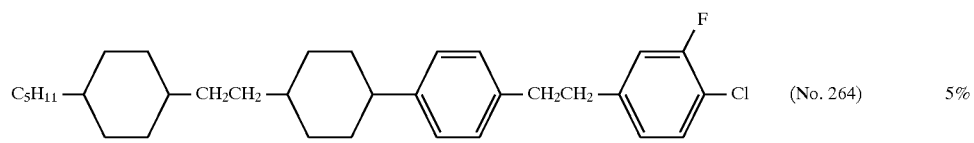 (No. 264) 5%
 9%
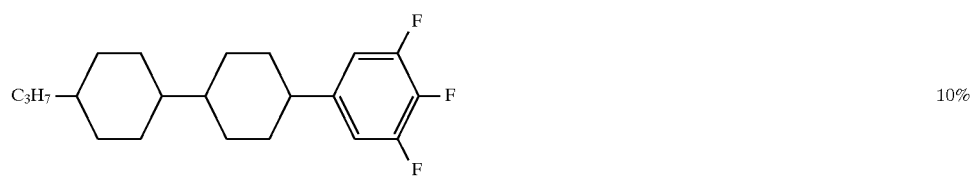 10%
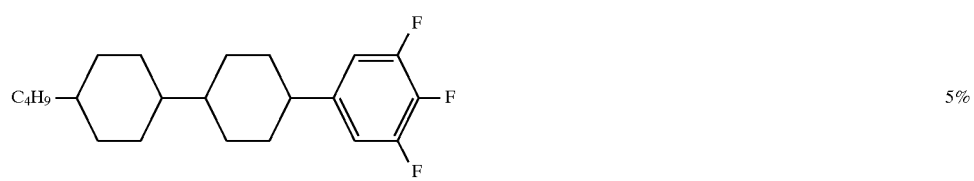 5%
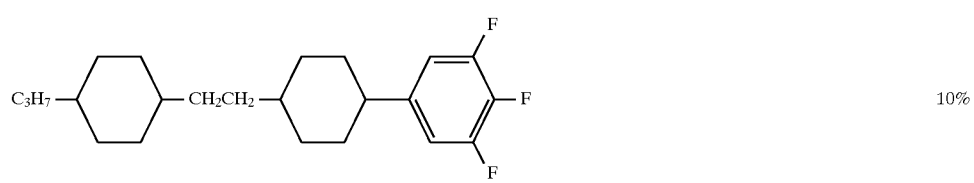 10%
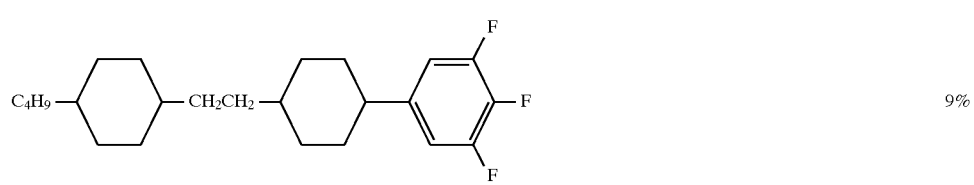 9%
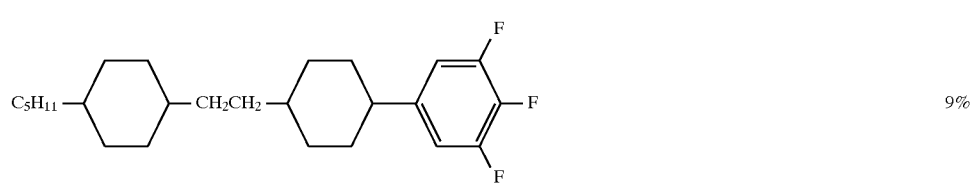 9%
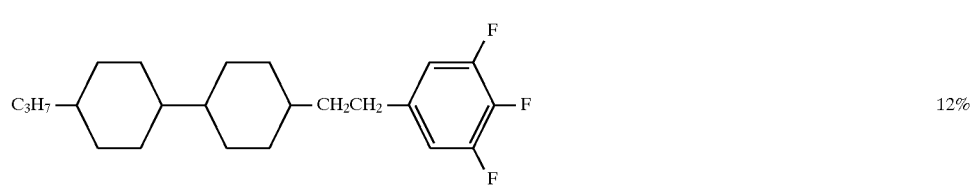 12%

-continued
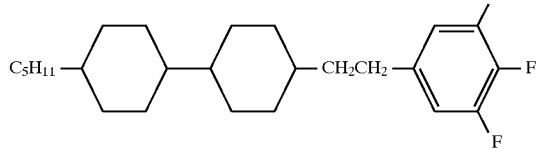  8%
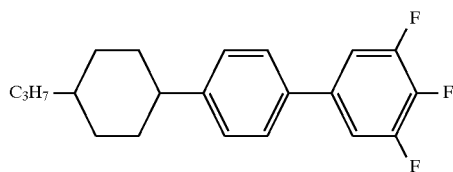  5%
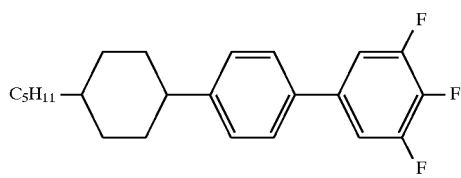  5%
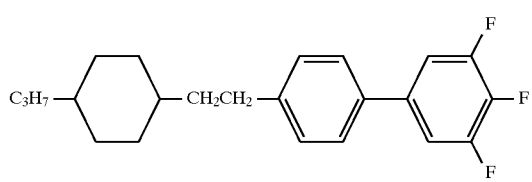  4%
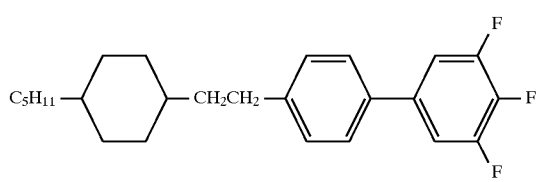  4%
COMPOSITION EXAMPLE 6
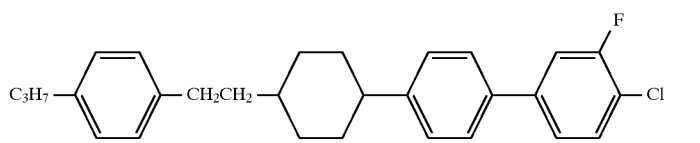  (No. 13)  5%
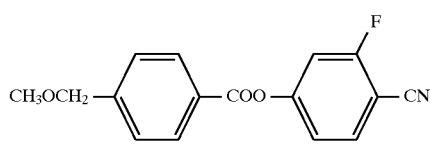  5%
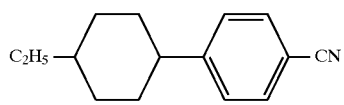  7%
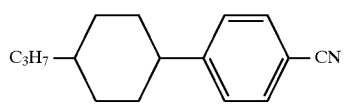  20%
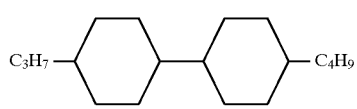  10%

-continued
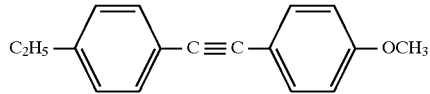 4%
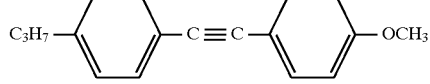 4%
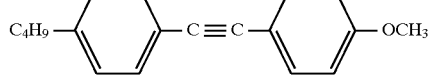 4%
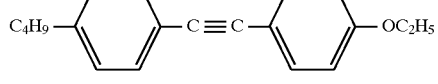 4%
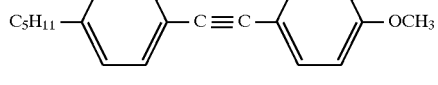 4%
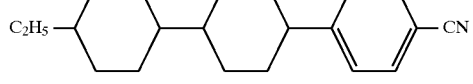 6%
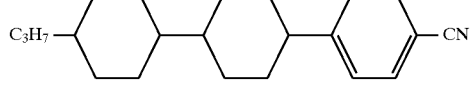 6%
 6%
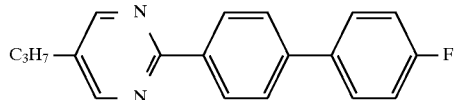 6%
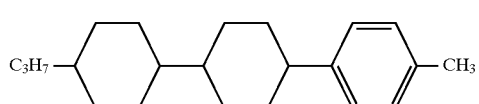 6%
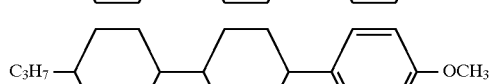 6%
COMPOSITION EXAMPLE 7
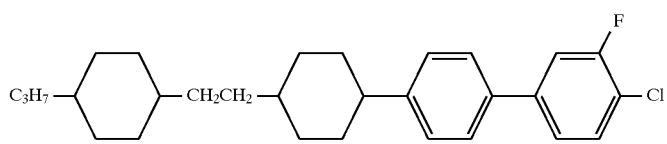 (No. 1) 5%
 11%

-continued
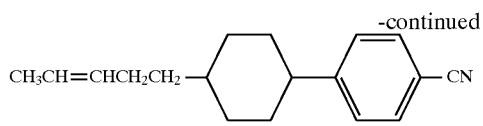 11%
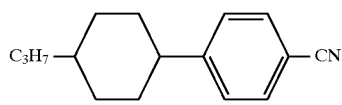 8%
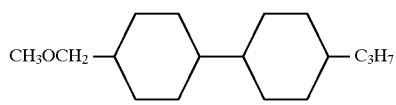 5%
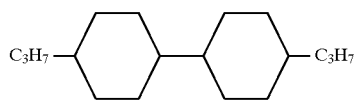 10%
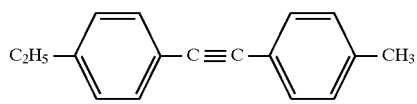 4%
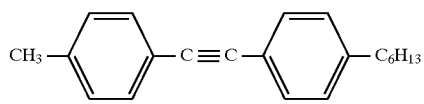 8%
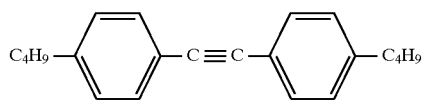 4%
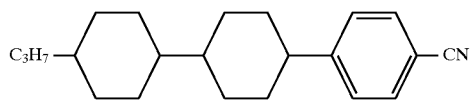 7%
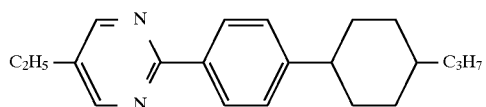 6%
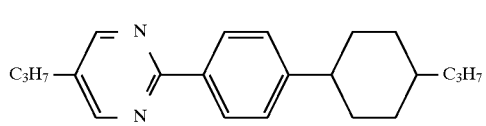 6%
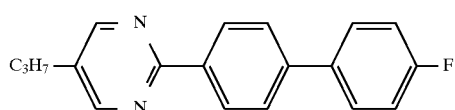 7%
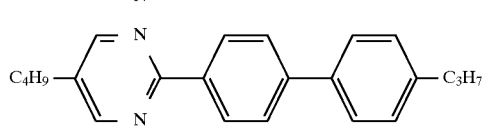 4%
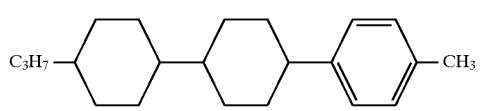 4%
| | |
|---|---|
| Cp (°C.) | 99.0 |
| (ηcP) | 24.3 |
| Δn | 0.162 |
| Δε | 7.0 |
| Vth | 2.16 |

COMPOSITION EXAMPLE 8
| Structure | | % |
|---|---|---|
| 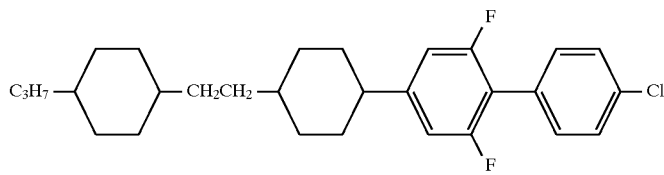 | (No. 38) | 6% |
| 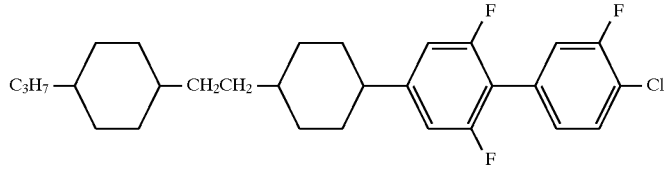 | (No. 52) | 6% |
| 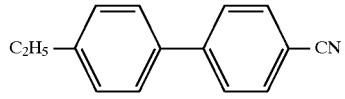 | | 8% |
| 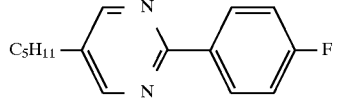 | | 6% |
| 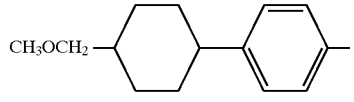 | | 10% |
| 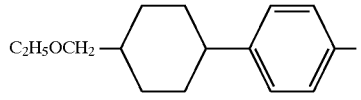 | | 10% |
| 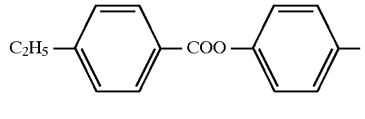 | | 5% |
| 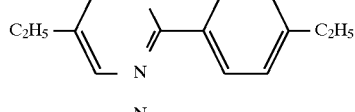 | | 3% |
| 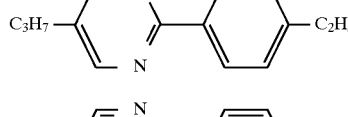 | | 3% |
| 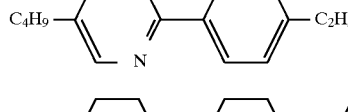 | | 3% |
|  | | 4% |
|  | | 6% |
| 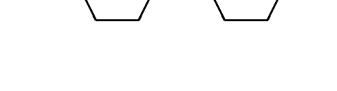 | | 9% |

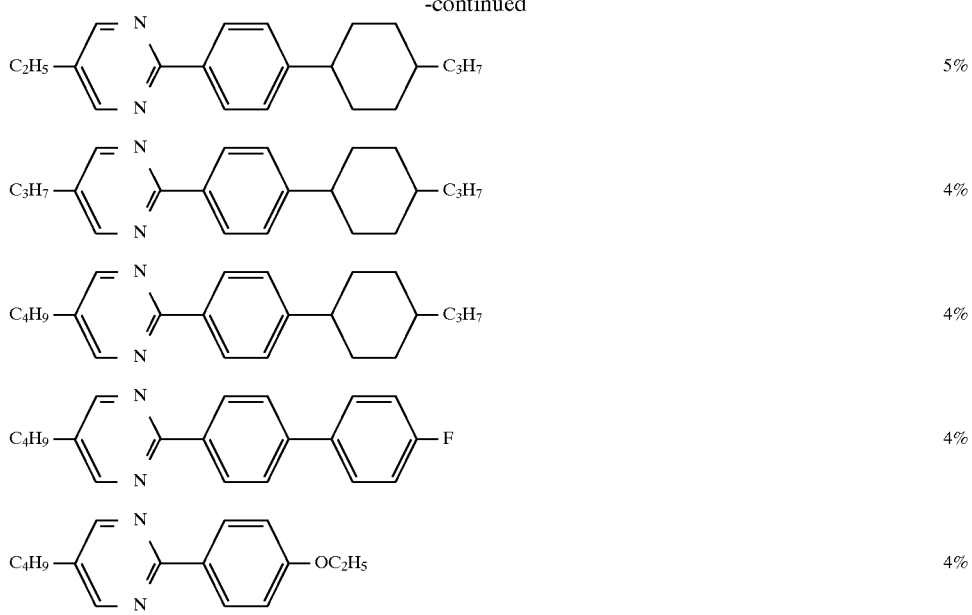
| | |
|---|---|
| | 5% |
| | 4% |
| | 4% |
| | 4% |
| | 4% |
COMPOSITION EXAMPLE 9
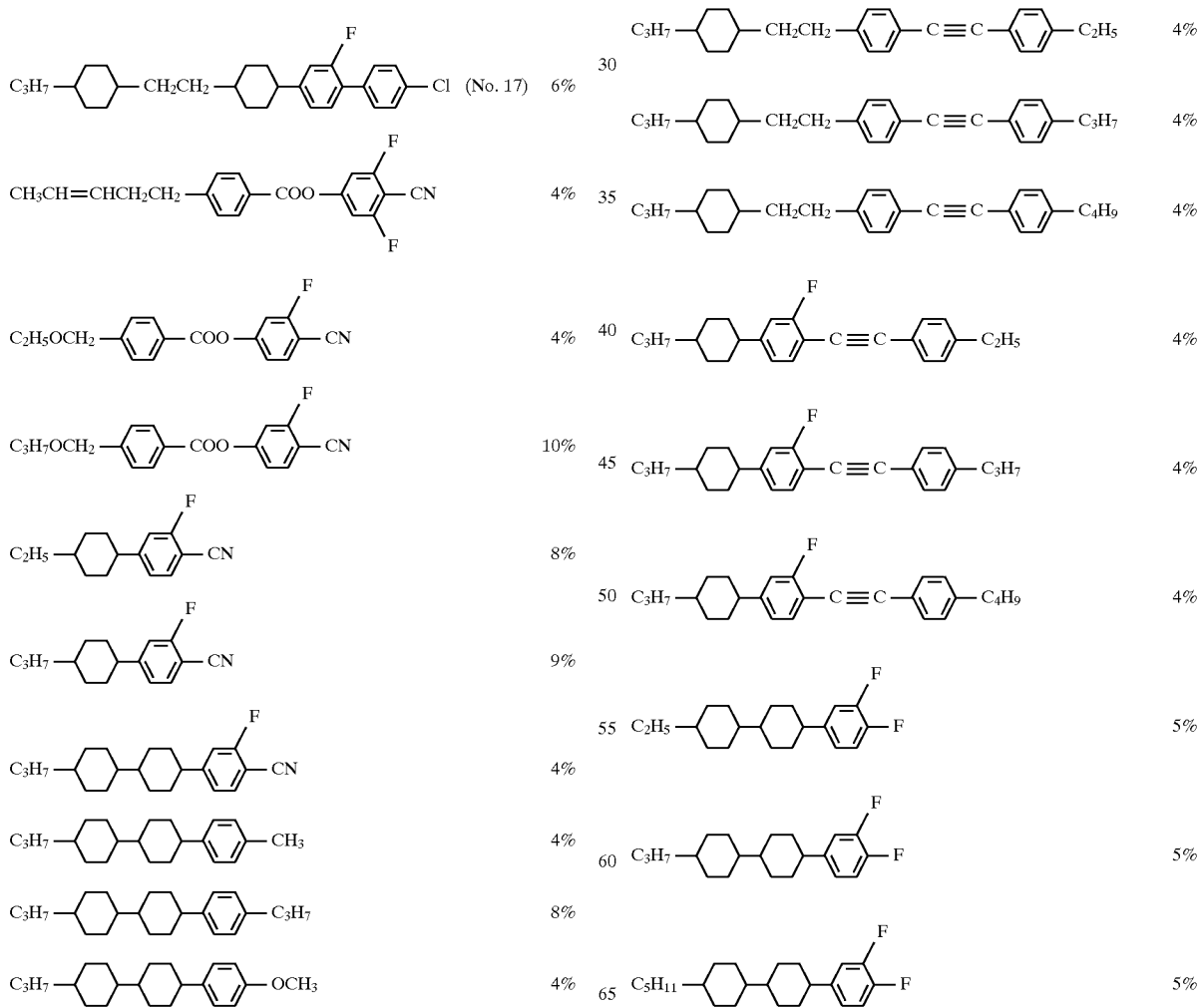
| | |
|---|---|
| (No. 17) | 6% |
| | 4% |
| | 4% |
| | 10% |
| | 8% |
| | 9% |
| | 4% |
| | 4% |
| | 8% |
| | 4% |
| -continued | |
| | 4% |
| | 4% |
| | 4% |
| | 4% |
| | 4% |
| | 4% |
| | 5% |
| | 5% |
| | 5% |

COMPOSITION EXAMPLE 10

| Compound | % |
|---|---|
| C$_3$H$_7$-Ph-CH$_2$CH$_2$-Cy-Ph-Ph(F)-Cl (No. 13) | 5% |
| C$_2$H$_5$-Ph-COO-Ph-CN | 8% |
| C$_2$H$_5$-Ph-Ph-CN | 15% |
| C$_3$H$_7$-Cy-Ph-CN | 8% |
| CH$_3$O-Ph-COO-Ph-C$_2$H$_5$ | 10% |
| C$_3$H$_7$-Cy-COO-Ph-OC$_4$H$_9$ | 10% |
| C$_4$H$_9$-Cy-COO-Ph-OC$_2$H$_5$ | 10% |
| C$_5$H$_{11}$-Cy-COO-Ph-OCH$_3$ | 10% |
| C$_3$H$_7$-Cy-Ph-COO-Ph-F | 4% |
| C$_3$H$_7$-Cy-Cy-COO-Ph-F | 4% |
| C$_5$H$_{11}$-Cy-Cy-COO-Ph-F | 4% |
| C$_3$H$_7$-Cy-COO-Ph-COO-Ph-F | 4% |
| C$_3$H$_7$-Cy-COO-Ph-COO-Ph-C$_2$H$_5$ | 4% |
| C$_3$H$_7$-Cy-COO-Ph-F | 4% |

COMPOSITION EXAMPLE 11

| Compound | % |
|---|---|
| C$_3$H$_7$-Cy-CH$_2$CH$_2$-Cy-Ph-Ph(F)-Cl (No. 17) | 5% |
| C$_3$H$_7$-Cy-CH$_2$CH$_2$-Cy-Ph(F,F)-Ph-Cl (No. 38) | 5% |
| C$_3$H$_7$-Cy-CH$_2$CH$_2$-Cy-Ph(F,F)-Ph(F)-Cl (No. 52) | 5% |
| C$_3$H$_7$-Cy-Cy-OCH$_3$ | 4% |
| C$_3$H$_7$-Cy-Cy-OC$_3$H$_7$ | 4% |
| C$_5$H$_{11}$-Cy-Cy-OCH$_3$ | 6% |
| C$_5$H$_{11}$-Cy-Ph-F | 6% |
| C$_2$H$_5$-Cy-Cy-Ph-OCF$_3$ | 4% |
| C$_3$H$_7$-Cy-Cy-Ph-OCF$_3$ | 4% |
| C$_4$H$_9$-Cy-Cy-Ph-OCF$_3$ | 6% |
| C$_6$H$_{13}$-Cy-Cy-Ph-OCF$_3$ | 6% |
| C$_3$H$_7$-Cy-Cy-CH$_2$CH$_2$-Ph(F,F) | 6% |
| C$_5$H$_{11}$-Cy-Cy-CH$_2$CH$_2$-Ph(F,F) | 6% |
| C$_3$H$_7$-Cy-Cy-Ph(F,F)-OCHF$_2$ | 10% |
| C$_3$H$_7$-Cy-Cy-COO-Ph(F,F) | 5% |
| C$_5$H$_{11}$-Cy-Ph-Ph(F,F) | 3% |
| C$_5$H$_{11}$-Cy-Ph-Ph(F)-C$_2$H$_5$ | 3% |
| C$_2$H$_5$-Cy-Cy-Ph-OCHF$_2$ | 6% |
| C$_3$H$_7$-Cy-Cy-Ph-OCHF$_2$ | 6% |

COMPOSITION EXAMPLE 12

| Compound | % |
|---|---|
| C$_5$H$_{11}$-Ph-Cy-CH$_2$CH$_2$-Ph-Ph(F)-Cl (No. 75) | 6% |
| C$_5$H$_{11}$-Cy-Ph-F | 10% |
| C$_6$H$_{13}$-Cy-Ph-F | 10% |
| C$_7$H$_{15}$-Cy-Ph-F | 10% |
| C$_2$H$_5$-Cy-Cy-Ph-OCF$_3$ | 7% |
| C$_3$H$_7$-Cy-Cy-Ph-OCF$_3$ | 7% |

-continued

| Structure | % |
|---|---|
| C$_4$H$_9$—[Cy]—[Cy]—[Ph]—OCF$_3$ | 7% |
| C$_5$H$_{11}$—[Cy]—[Cy]—[Ph]—OCF$_3$ | 7% |
| C$_3$H$_7$—[Cy]—[Cy]—CH$_2$CH$_2$—[Ph]—OCF$_3$ | 6% |
| C$_5$H$_{11}$—[Cy]—[Cy]—CH$_2$CH$_2$—[Ph]—OCF$_3$ | 6% |
| C$_3$H$_7$—[Cy]—[Ph]—[Ph(3,4-F$_2$)] | 9% |
| C$_5$H$_{11}$—[Cy]—[Ph]—[Ph(3,4-F$_2$)] | 9% |
| C$_3$H$_7$—[Cy]—[Ph(2-F)]—[Ph]—[Cy]—C$_3$H$_7$ | 3% |
| C$_5$H$_{11}$—[Cy]—[Ph(2-F)]—[Ph]—[Cy]—C$_3$H$_7$ | 3% |

COMPOSITION EXAMPLE 13

| Structure | | % |
|---|---|---|
| C$_5$H$_{11}$—[Cy]—CH$_2$CH$_2$—[Cy]—[Ph]—CH$_2$CH$_2$—[Ph(3-F,4-Cl)] | (No. 264) | 5% |
| C$_3$H$_7$—[Ph]—CH$_2$CH$_2$—[Cy]—[Ph]—[Ph(3-F,4-Cl)] | (No. 13) | 5% |
| CH$_2$=CHCH$_2$—[Cy]—[Ph]—CN | | 4% |
| C$_4$H$_9$—[Ph]—[Ph]—C$_2$H$_5$ | | 4% |
| C$_3$H$_7$—[Ph]—[Ph]—CN | | 6% |
| C$_5$H$_{11}$—[Ph]—[Ph]—CN | | 6% |

-continued

| Structure | % |
|---|---|
| C₂H₅–(Cy)–(Ph-3F)–CN | 6% |
| C₃H₇–(Cy)–CH₂CH₂–(Ph)–OC₂H₅ | 5% |
| C₅H₁₁–(Cy)–CH₂CH₂–(Ph)–OC₃H₇ | 9% |
| C₃H₇–(Cy)–COO–(Ph)–OCH₃ | 12% |
| C₅H₁₁–(Cy)–COO–(Ph)–OC₃H₇ | 12% |
| C₃H₇–(Cy)–COO–(Ph)–CN | 6% |
| C₅H₁₁–(Ph)–(Ph)–(Ph)–CN | 4% |
| C₄H₉–(Ph)–(Pyrimidine)–(Ph)–CN | 4% |
| C₄H₉–(Ph)–(Pyrimidine)–(Ph)–C₅H₁₁ | 4% |
| C₅H₁₁–(Cy)–(Ph)–CH₂CH₂–(Ph)–C₄H₉ | 4% |
| C₅H₁₁–(Cy)–(Ph)–(Ph)–CH₂CH₂–(Ph)–C₃H₇ | 4% |

COMPOSITION EXAMPLE 14

| Structure | % |
|---|---|
| C₃H₇–(Cy)–CH₂CH₂–(Cy)–(Ph-2,6-diF)–(Ph)–Cl (No. 38) | 5% |
| C₃H₇–(Cy)–CH₂CH₂–(Cy)–(Ph-2,6-diF)–(Ph-3F)–Cl (No. 52) | 5% |

-continued

| Structure | % |
|---|---|
| C₄H₉–(Cy)–COO–(Ph-3,4-diF) | 6% |
| C₅H₁₁–(Cy)–COO–(Ph-3,4-diF) | 6% |
| C₂H₅–(Cy)–COO–(Ph-3F)–CN | 5% |

-continued
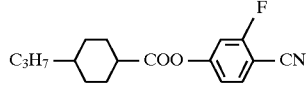 5%
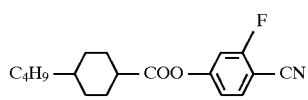 7%
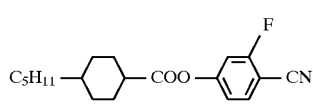 7%
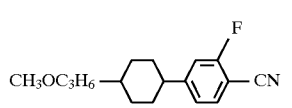 10%
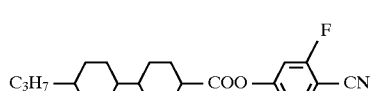 5%
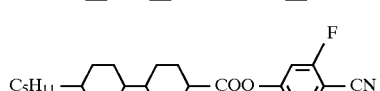 7%
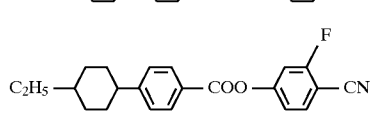 5%
 5%
 6%
 6%
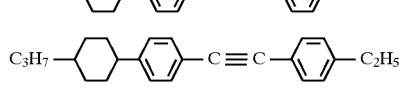 10%
COMPOSITION EXAMPLE 15
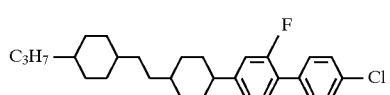 4.0%
(Compound No. 38)
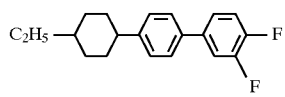 5.0%
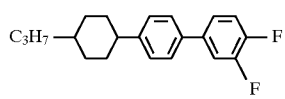 5.0%
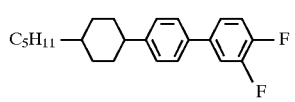 10.0%
-continued
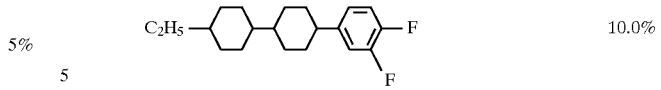 10.0%
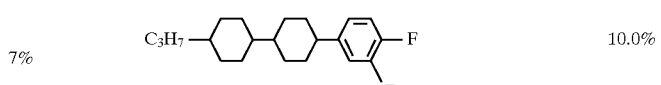 10.0%
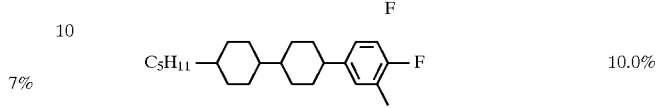 10.0%
 6.0%
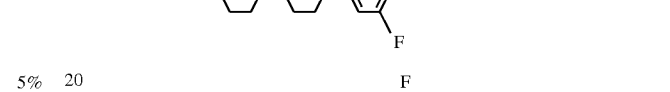 4.0%
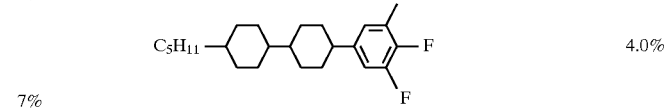 10.0%
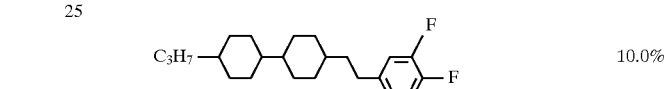 10.0%
 5.0%
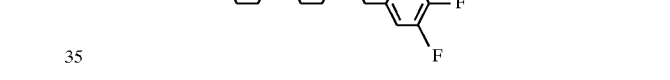 5.0%
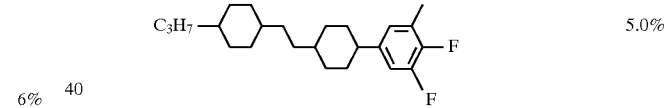 6.0%
| | |
|---|---|
| Cp(°C.) | 110.3 |
| η(cP) | 29.9 |
| Δn | 0.096 |
| Δε | 6.2 |
| Vth | 2.44 |
COMPOSITION EXAMPLE 16
 5.0%
(Compound No. 1)

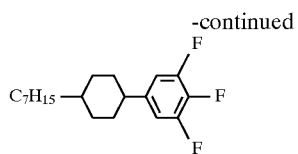 5.0%
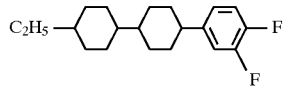 10.0%
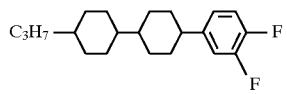 10.0%
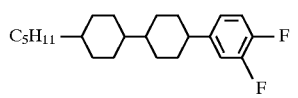 10.0%
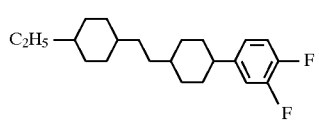 8.0%
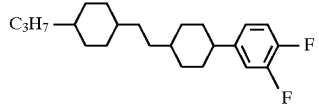 4.0%
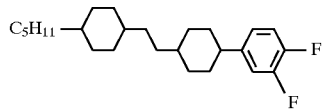 8.0%
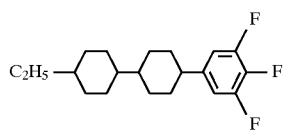 6.0%
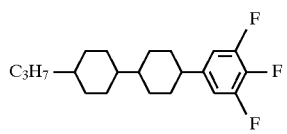 6.0%
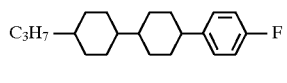 5.0%
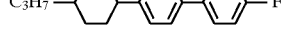 5.0%
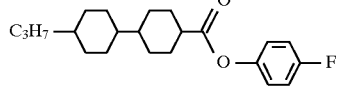 5.0%
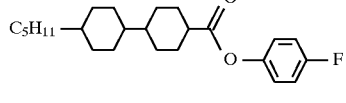 5.0%
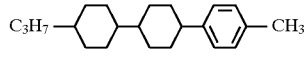 4.0%
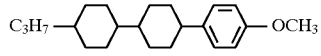 4.0%
Cp(°C.)  118.8
η(cP)    27.9
Δn       0.087
Δε       4.7
Vth      2.40
COMPOSITION EXAMPLE 17
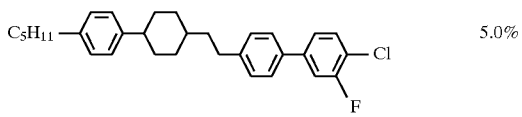 5.0%
(Compound No. 75)
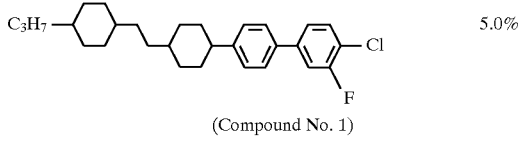 5.0%
(Compound No. 1)
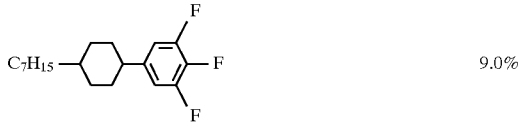 9.0%
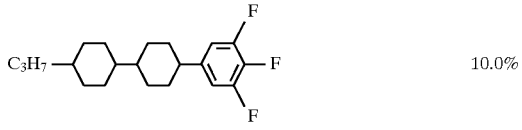 10.0%
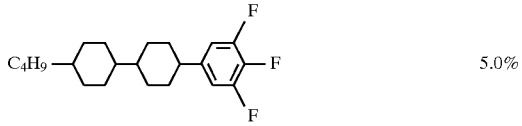 5.0%
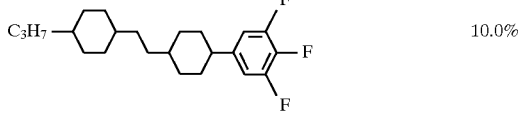 10.0%
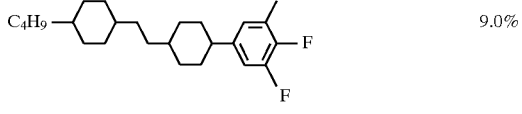 9.0%
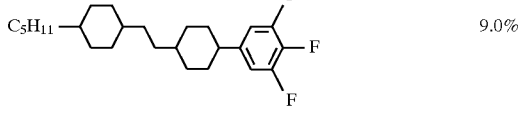 9.0%
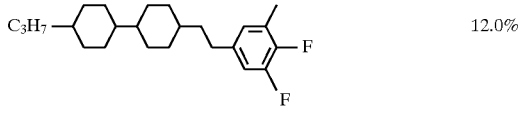 12.0%
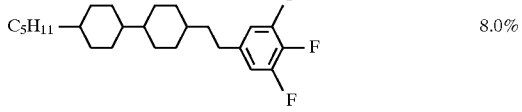 8.0%

-continued
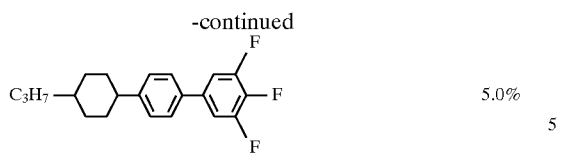 5.0%
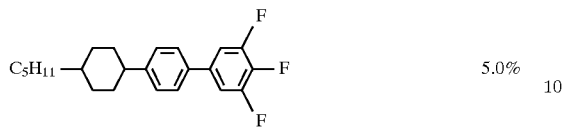 5.0%
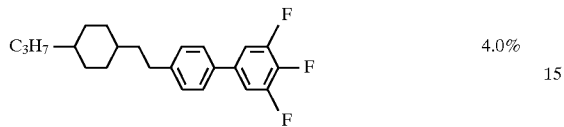 4.0%
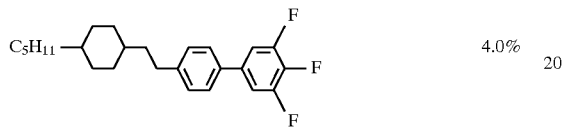 4.0%
| | |
|---|---|
| Cp(°C.) | 83.5 |
| η(cP) | 28.8 |
| Δn | 0.091 |
| Δε | 8.0 |
| Vth | 1.78 |
COMPOSITION EXAMPLE 18
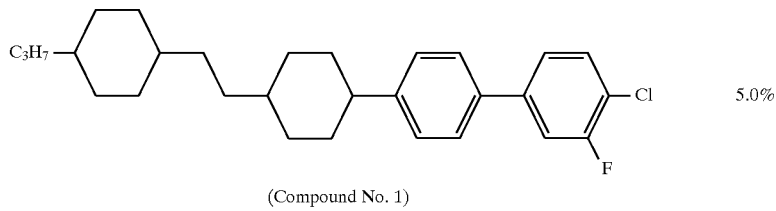 5.0%
(Compound No. 1)
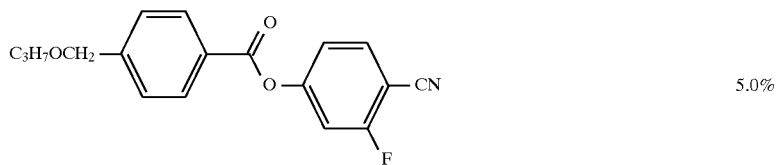 5.0%
 7.0%
 20.0%
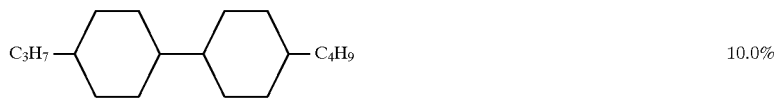 10.0%
 4.0%

-continued

C₃H₇—〈benzene〉—C≡C—〈benzene〉—OCH₃        4.0%

C₄H₉—〈benzene〉—C≡C—〈benzene〉—OCH₃        4.0%

C₄H₉—〈benzene〉—C≡C—〈benzene〉—OC₂H₅       4.0%

C₅H₁₁—〈benzene〉—C≡C—〈benzene〉—OCH₃       4.0%

C₂H₅—〈cyclohexane〉—〈cyclohexane〉—〈benzene〉—CN   6.0%

C₃H₇—〈cyclohexane〉—〈cyclohexane〉—〈benzene〉—CN   6.0%

C₄H₉—〈cyclohexane〉—〈cyclohexane〉—〈benzene〉—CN   6.0%

C₃H₇—〈pyrimidine〉—〈benzene〉—〈benzene〉—F        6.0%

C₃H₇—〈cyclohexane〉—〈cyclohexane〉—〈benzene〉—CH₃  6.0%

C₃H₇—〈cyclohexane〉—〈cyclohexane〉—〈benzene〉—OCH₃ 3.0%

Cp(°C.)  100.1
η(cP)    25.1
Δn       0.160
Δε       9.4
Vth      1.79

COMPOSITION EXAMPLE 19

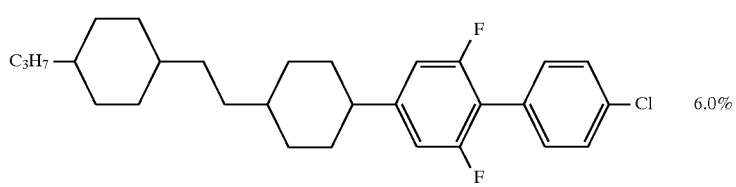

(Compound No. 38)   6.0%

-continued
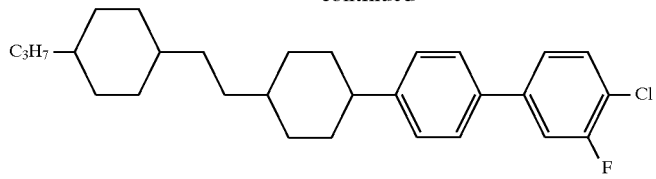 6.0%
(Compound No. 1)
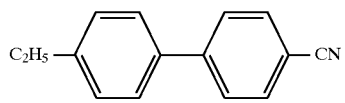 8.0%
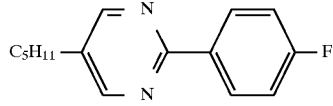 6.0%
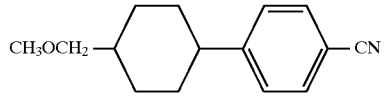 10.0%
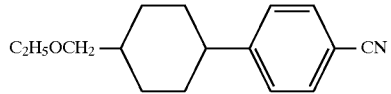 10.0%
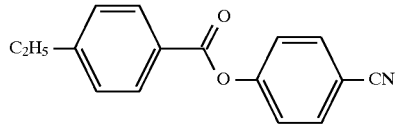 5.0%
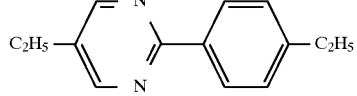 3.0%
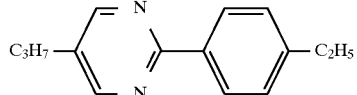 3.0%
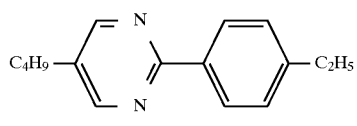 3.0%
 4.0%
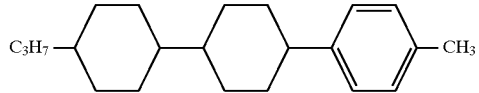 6.0%
 9.0%
 5.0%

-continued
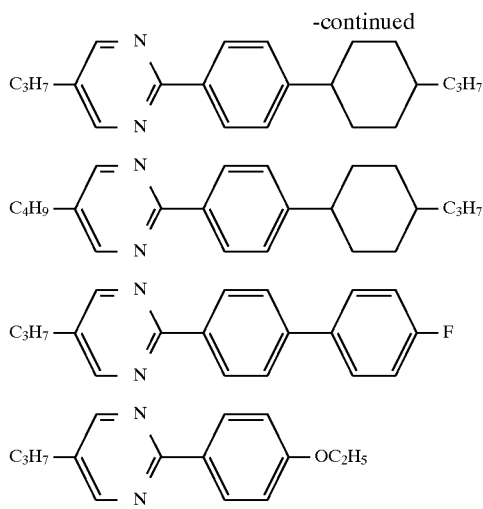
4.0%
4.0%
4.0%
4.0%
Cp(°C.)   85.8
η(cP)     35.3
Δn        0.152
Δε        10.2
Vth       1.35
COMPOSITION EXAMPLE 20
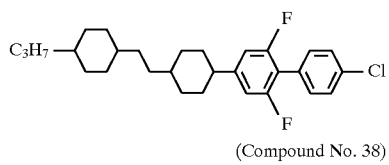   6.0%
(Compound No. 38)
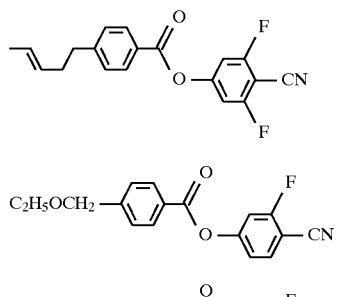
4.0%
10.0%
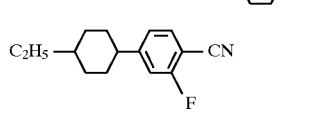   8.0%
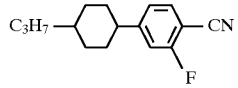   9.0%
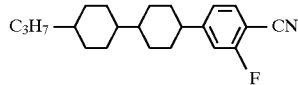   4.0%
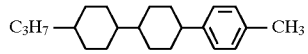   4.0%
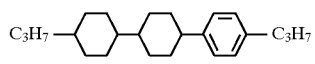   8.0%
-continued
4.0%
4.0%
4.0%
4.0%
4.0%
4.0%
4.0%
5.0%
5.0%
5.0%

-continued
Cp(°C.) 107.2
η(cP)   36.4
Δn      0.148
Δε      15.8
Vth     1.56
COMPOSITION EXAMPLE 21
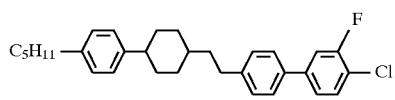 5.0%
(Compound No. 75)
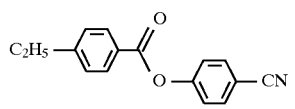 8.0%
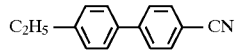 15.0%
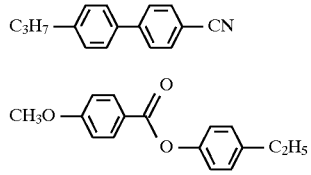 8.0%
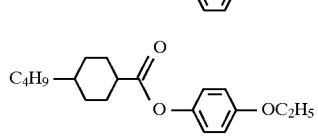 10.0%
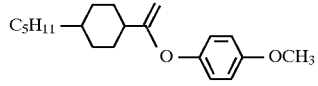 10.0%
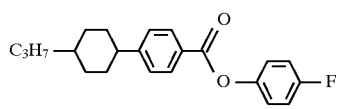 10.0%
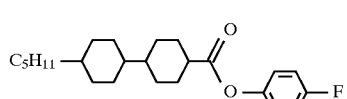 10.0%
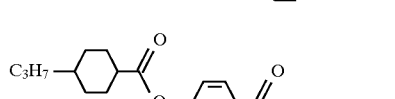 4.0%
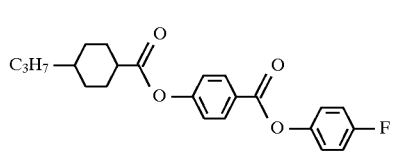 4.0%
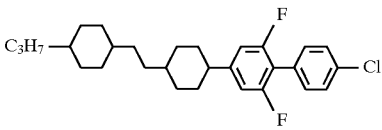 4.0%
 4.0%
-continued
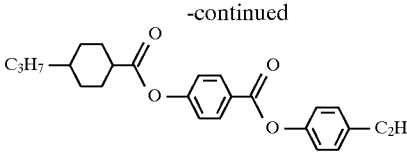 4.0%
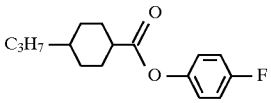 4.0%
Cp(°C.) 73.7
η(cP)   36.4
Δn      0.131
Δε      8.0
Vth     1.54
COMPOSITION EXAMPLE 22
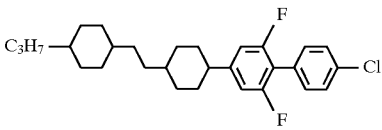 5.0%
(Compound No. 38)
 4.0%
 7.0%
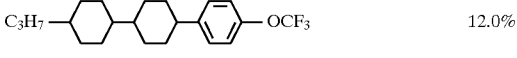 12.0%
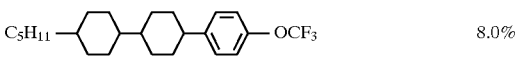 8.0%
 5.0%
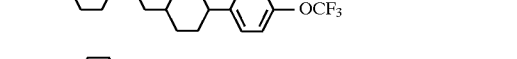 5.0%
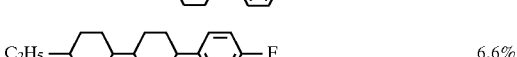 6.6%
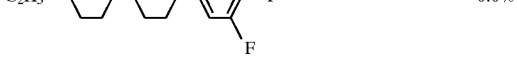 6.7%
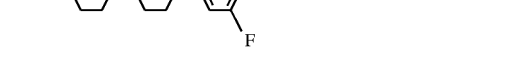 6.7%
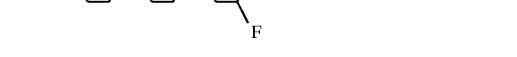 5.0%
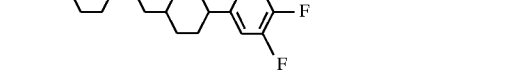 4.0%

-continued
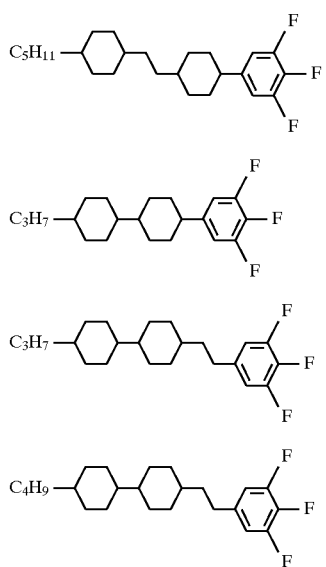
| | |
|---|---|
| Cp(°C.) | 98.8 |
| η(cP) | 21.6 |
| Δn | 0.080 |
| Δε | 5.5 |
| Vth | 2.17 |
-continued
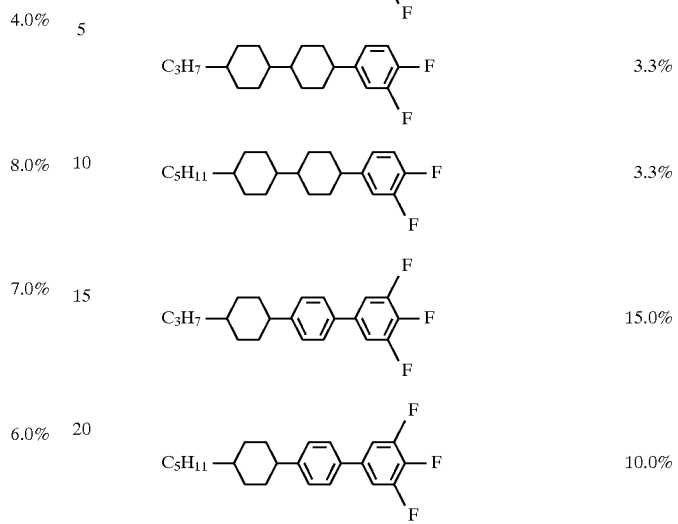
| | |
|---|---|
| Cp(°C.) | 99.6 |
| η(cP) | 22.5 |
| Δn | 0.117 |
| Δε | 6.3 |
| Vth | 2.10 |
COMPOSITION EXAMPLE 23
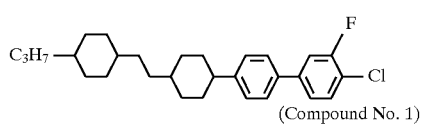 3.0% (Compound No. 1)
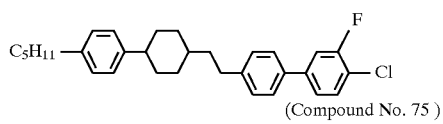 3.0% (Compound No. 75)
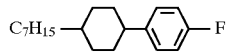 8.0%
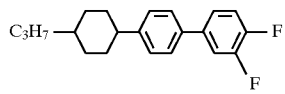 13.0%
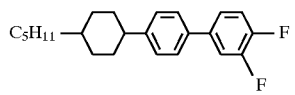 13.0%
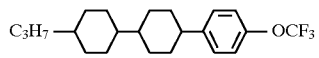 10.0%
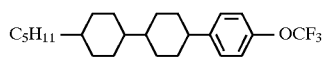 7.0%
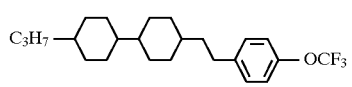 4.0%
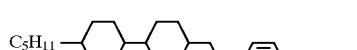 4.0%
COMPOSITION EXAMPLE 24
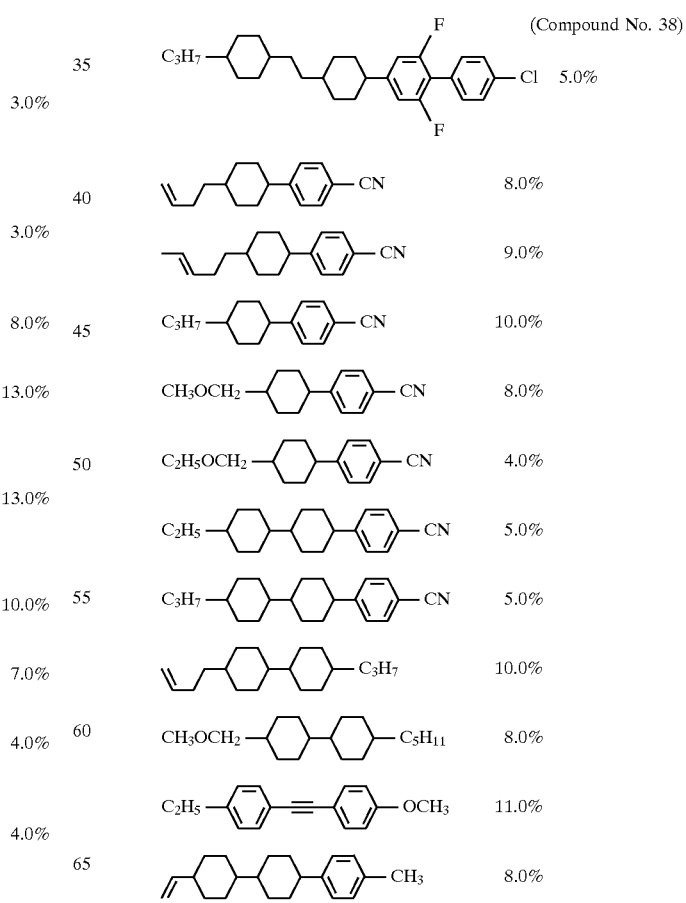

-continued

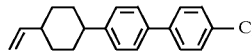 C₂H₅  5.0%

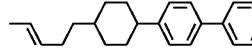 C₂H₅  4.0%

| | |
|---|---|
| Cp(° C.) | 86.4 |
| η(cP) | 21.0 |
| Δn | 0.136 |
| Δε | 8.1 |
| Vth | 1.93 |

COMPOSITION EXAMPLE 25

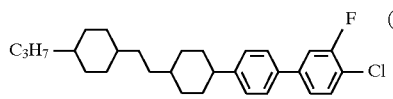 (Compound No. 1) 5.0%

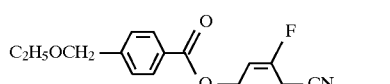 6.0%

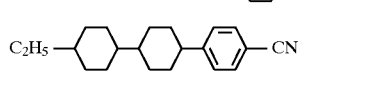 CN 4.0%

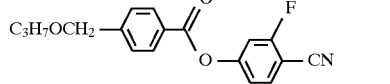 12.0%

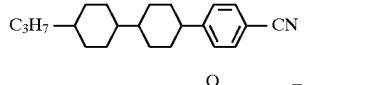 CN 4.0%

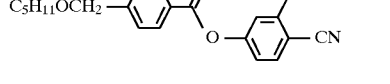 6.0%

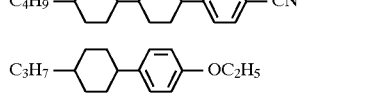 CN 4.0%

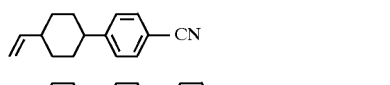 OC₂H₅ 7.0%

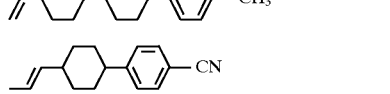 CN 10.0%

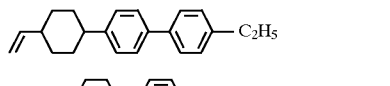 CH₃ 7.0%

 CN 10.0%

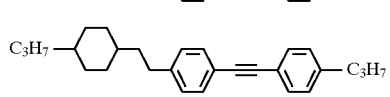 C₂H₅ 4.0%

 CN 11.0%

 C₂H₅ 4.0%

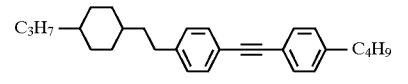 C₃H₇ 3.0%

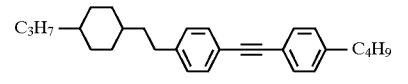 C₄H₉ 3.0%

| | |
|---|---|
| Cp(° C.) | 83.0 |
| η(cP) | 35.9 |
| Δn | 0.149 |
| Δε | 16.9 |
| Vth | 1.26 |

Now, the present invention will be described in more detail with reference to Examples. However, it should be understood that the present invention is by no means restricted by such specific Examples. In each of the Examples, CN represents a crystal phase-nematic phase transition point (°C.) and NI represents a nematic phase-isotropic phase transition point (°C.).

EXAMPLE 1

Preparation of 3-fluoro-4-chloro-4'-(trans-4-(2-(trans-4-n-propylcyclohexyl)ethyl)cyclohexyl)biphenyl (compound expressed by general formula (I) wherein both ring A and ring B represent 1,4-cyclohexylene, ring C represent 1,4-phenylene, $Z_1$ represents —CH₂CH₂—, both $Z_2$ and $Z_3$ represent covalent bond, $L_1$ represents F atom, $L_2$ represents H atom, and R represents n-propyl group; Compound No. 1)

(1) Metal magnesium in an amount of 11.6 g was suspended in 100 ml of tetrahydrofuran (hereinafter referred to as THF) under nitrogen gas stream, and a solution prepared by dissolving 69 g of bromobenzene in 200 ml of THF was added dropwise in the suspension and then stirred at room temperature for 1 hour. A solution prepared by dissolving 100 g of 4-(2-(trans-4-n-propylcyclohexyl)ethyl) cyclohexanone in 300 ml of THF was added dropwise thereto and stirred at room temperature for 1 hour. After finishing of the reaction, 500 ml of dilute hydrochloric acid was added thereto and extracted with 1 l of ethyl acetate. Organic layer was washed with water and dried over anhydrous magnesium sulfate, and the solvent was distilled off under a reduced pressure to obtain 119 g of (1-hydroxy-4-(2-(trans-4-n-propylcyclohexyl)ethyl)cyclohexyl)benzene.

(2) To 500 ml of toluene was dissolved 119 g of (1-hydroxy-(4-(2-(trans-4-n-propylcyclohexyl)ethyl) cyclohexyl)benzene, 10 g of Amberlist 15E was added as catalyst to the solution, and the solution was stirred under a reflux for 2 hours. After the reaction solution was cooled, the catalyst was filtered off. Organic layer was washed with water and dried over anhydrous magnesium sulfate, and the solvent was distilled off under a reduced pressure to obtain 92 g of (4-(2-(trans-4-n-propylcycloheyxl)ethyl) cyclohexene-1-yl)benzene.

(3) To a liquid mixture comprising 250 ml of ethanol and 250 ml of toluene was dissolved 92 g of the (4-(2-(trans-4-n-propylcyclohexyl)ethyl)cyclohexene-1-yl)benzene mentioned above, 5 g of palladium/carbon (5%) was added as catalyst thereto, and they were subjected to a catalytic reduction in hydrogen gas atmosphere. After finishing of the reaction, the catalyst was filtered off and the solvent was distilled off under a reduced pressure to obtain a yellow oily product. This product was recrystallized from ethanol to obtain 58.5 g of (trans-4-(2-(trans-4-n-propylcyclohexyl) ethyl)cyclohexyl)benzene.

(4) To a mixed solution comprising 500 ml of acetic acid, 50 ml of carbon tetrachloride, 50 ml of concentrated sulfuric acid, and 100 ml of water were added 58.5 g of the (trans-4-(2-(trans-4-n-propylcyclohexyl)ethyl)cyclohexyl) benzene mentioned above, 22.1 g of iodine, and 18.4 g of iodic acid, and the mixture was stirred under a reflux for 2 hours. After cooled, the mixture was washed with a saturated aqueous solution of sodium thiosulfate. Organic layer was washed with water and dried over anhydrous magnesium sulfate, and the solvent was distilled off under a reduced pressure to obtain a yellow-brown oily product. This product was purified by a column chromatography over an alumina by using heptane as an eluent. Further, it was recrystallized from heptane to obtain 9.7 g of 4-(trans-4-(2-(trans-4-n-propylcyclohexyl)ethyl)cyclohexyl)iodobenzene.

(5) Metal magnesium in an amount of 1.2 g was suspended in 20 ml of THF under nitrogen gas stream, and a solution prepared by dissolving 9.6 g of 3-fluoro-4-chloro-bromobenzene in 50 ml of THF was added dropwise thereto and stirred at room temperature for 1 hour to prepare a solution of Grignard reagent.

In 30 ml of THF was dissolved 9.7 g of the 4-(trans-4-(2-(trans-4-n-propylcyclohexyl)ethyl)cyclohexyl) iodobenzene mentioned above, 1 g of palladium chloride was added thereto, and they were stirred under a reflux. The Grignard reagent prepared by the procedures mentioned above was added dropwise thereto and they were reacted while stirring for 2 hours. Reaction solution thus obtained was added to 100 ml of dilute hydrochloric acid and the product was extracted with 100 ml of heptane. Organic layer was washed with water and dried over anhydrous magnesium sulfate, and the solvent was distilled off under a reduced pressure to obtain a yellow-brown oily product. This product was purified by a column chromatography over an alumina by using heptane as an eluent. Further, the product was recrystallized from heptane to obtain 2.3 g of the subject compound. CN 138.1, NI 227.7

According to the procedures mentioned above, following Compounds No. 2 to No. 63 were synthesized:
No.
2. 4-chloro-4'-(trans-4-(2-(trans-4-methylcyclohexyl)ethyl) cyclohexyl)biphenyl
3. 4-chloro-4'-(trans-4-(2-(trans-4-ethylcyclohexyl)ethyl) cyclohexyl)biphenyl
4. 4-chloro-4'-(trans-4-(2-(trans-4-n-propylcyclohexyl) ethyl)cyclohexyl)biphenyl
5. 4-chloro-4'-(trans-4-(2-(trans-4-n-butylcyclohexyl)ethyl) cyclohexyl)biphenyl
6. 4-chloro-4'-(trans-4-(2-(trans-4-n-pentylcyclohexyl) ethyl)cyclohexyl)biphenyl
7. 4-chloro-4'-(trans-4-(2-(trans-4-n-hexylcyclohexyl)ethyl) cyclohexyl)biphenyl
8. 4-chloro-4'-(trans-4-(2-(trans-4-n-heptylcyclohexyl) ethyl)cyclohexyl)biphenyl
9. 3-fluoro-4-chloro-4'-(trans-4-(2-(trans-4-methylcyclohexyl)ethyl)cyclohexyl)biphenyl
10. 3-fluoro-4-chloro-4'-(trans-4-(2-(trans-4-ethylcyclohexyl)ethyl)cyclohexyl)biphenyl
11. 3-fluoro-4-chloro-4'-(trans-4-(2-(trans-4-n-butylcyclohexyl)ethyl)cyclohexyl)biphenyl
12. 3-fluoro-4-chloro-4'-(trans-4-(2-(trans-4-n-pentylcyclohexyl)ethyl)cyclohexyl)biphenyl
13. 3-fluoro-4-chloro-4'-(trans-4-(2-(trans-4-n-propylcyclohexyl)ethyl)cyclohexyl)biphenyl
14. 3-fluoro-4-chloro-4'-(trans-4-(2-(trans-4-n-heptylcyclohexyl)ethyl)cyclohexyl)biphenyl
15. 2'-fluoro-4-chloro-4'-(trans-4-(2-(trans-4-methylcyclohexyl)ethyl)cyclohexyl)biphenyl
16. 2'-fluoro-4-chloro-4'-(trans-4-(2-(trans-4-ethylcyclohexyl)ethyl)cyclohexyl)biphenyl
17. 2'-fluoro-4-chloro-4'-(trans-4-(2-(trans-4-n-propylcyclohexyl)ethyl)cyclohexyl)biphenyl

CN 117.6, NI 250

18. 2'-fluoro-4-chloro-4'-(trans-4-(2-(trans-4-n-butylcyclohexyl)ethyl)cyclohexyl)biphenyl
19. 2'-fluoro-4-chloro-4'-(trans-4-(2-(trans-4-n-pentylcyclohexyl)ethyl)cyclohexyl)biphenyl
20. 2'-fluoro-4-chloro-4'-(trans-4-(2-(trans-4-n-nonylcyclohexyl)ethyl)cyclohexyl)biphenyl
21. 2'-fluoro-4-chloro-4'-(trans-4-(2-(trans-4-n-hexylcyclohexyl)ethyl)cyclohexyl)biphenyl
22. 2',3-difluoro-4-chloro-4'-(trans-4-(2-(trans-4-methylcyclohexyl)ethyl)cyclohexyl)biphenyl
23. 2',3-difluoro-4-chloro-4'-(trans-4-(2-(trans-4-ethylcyclohexyl)ethyl)cyclohexyl)biphenyl
24. 2',3-difluoro-4-chloro-4'-(trans-4-(2-(trans-4-n-propylcyclohexyl)ethyl)cyclohexyl)biphenyl

CN 109.1, NI 221,6

25. 2',3-difluoro-4-chloro-4'-(trans-4-(2-(trans-4-n-butylcyclohexyl)ethyl)cyclohexyl)biphenyl
26. 2',3-difluoro-4-chloro-4'-(trans-4-(2-(trans-4-n-pentylcyclohexyl)ethyl)cyclohexyl)biphenyl
27. 2',3-difluoro-4-chloro-4'-(trans-4-(2-(trans-4-n-hexylcyclohexyl)ethyl)cyclohexyl)biphenyl
28. 2',3-difluoro-4-chloro-4'-(trans-4-(2-(trans-4-n-heptylcyclohexyl)ethyl)cyclohexyl)biphenyl
29. 3,5-difluoro-4-chloro-4'-(trans-4-(2-(trans-4-methylcyclohexyl)ethyl)cyclohexyl)biphenyl
30. 3,5-difluoro-4-chloro-4'-(trans-4-(2-(trans-4-ethylcyclohexyl)ethyl)cyclohexyl)biphenyl
31. 3,5-difluoro-4-chloro-4'-(trans-4-(2-(trans-4-n-propylcyclohexyl)ethyl)cyclohexyl)biphenyl
32. 3,5-difluoro-4-chloro-4'-(trans-4-(2-(trans-4-n-butylcyclohexyl)ethyl)cyclohexyl)biphenyl
33. 3,5-difluoro-4-chloro-4'-(trans-4-(2-(trans-4-n-pentylcyclohexyl)ethyl)cyclohexyl)biphenyl
34. 3,5-difluoro-4-chloro-4'-(trans-4-(2-(trans-4-n-hexylcyclohexyl)ethyl)cyclohexyl)biphenyl
35. 3,5-difluoro-4-chloro-4'-(trans-4-(2-(trans-4-n-octylcyclohexyl)ethyl)cyclohexyl)biphenyl
36. 2',6'-difluoro-4-chloro-4'-(trans-4-(2-(trans-4-methylcyclohexyl)ethyl)cyclohexyl)biphenyl
37. 2',6'-difluoro-4-chloro-4'-(trans-4-(2-(trans-4-ethylcyclohexyl)ethyl)cyclohexyl)biphenyl
38. 2',6'-difluoro-4-chloro-4'-(trans-4-(2-(trans-4-n-propylcyclohexyl)ethyl)cyclohexyl)biphenyl

CN 110.6, NI 234.6

39. 2',6'-difluoro-4-chloro-4'-(trans-4-(2-(trans-4-n-butylcyclohexyl)ethyl)cyclohexyl)biphenyl
40. 2',6'-difluoro-4-chloro-4'-(trans-4-(2-(trans-4-n-pentylcyclohexyl)ethyl)cyclohexyl)biphenyl
41. 2',6'-difluoro-4-chloro-4'-(trans-4-(2-(trans-4-n-hexylcyclohexyl)ethyl)cyclohexyl)biphenyl
42. 2',6'-difluoro-4-chloro-4'-(trans-4-(2-(trans-4-n-heptylcyclohexyl)ethyl)cyclohexyl)biphenyl
43. 2',3,5-trifluoro-4-chloro-4'-(trans-4-(2-(trans-4-methylcyclohexyl)ethyl)cyclohexyl)biphenyl
44. 2',3,5-trifluoro-4-chloro-4'-(trans-4-(2-(trans-4-ethylcyclohexyl)ethyl)cyclohexyl)biphenyl
45. 2',3,5-trifluoro-4-chloro-4'-(trans-4-(2-(trans-4-n-propylcyclohexyl)ethyl)cyclohexyl)biphenyl 46. 2',3,5-trifluoro-4-chloro-4'-(trans-4-(2-(trans-4-n-butylcyclohexyl)ethyl)cyclohexyl)biphenyl
47. 2',3,5-trifluoro-4-chloro-4'-(trans-4-(2-(trans-4-n-pentylcyclohexyl)ethyl)cyclohexyl)biphenyl
48. 2',3,5-trifluoro-4-chloro-4'-(trans-4-(2-(trans-4-n-hexylcyclohexyl)ethyl)cyclohexyl)biphenyl
49. 2',3,5-trifluoro-4-chloro-4'-(trans-4-(2-(trans-4-n-decylcyclohexyl)ethyl)cyclohexyl)biphenyl
50. 2',3,6'-trifluoro-4-chloro-4'-(trans-4-(2-(trans-4-methylcyclohexyl)ethyl)cyclohexyl)biphenyl
51. 2',3,6'-trifluoro-4-chloro-4'-(trans-4-(2-(trans-4-ethylcyclohexyl)ethyl)cyclohexyl)biphenyl
52. 2',3,6'-trifluoro-4-chloro-4'-(trans-4-(2-(trans-4-n-propylcyclohexyl)ethyl)cyclohexyl)biphenyl

CN 107.6, NI 228.5

53. 2',3,6'-trifluoro-4-chloro-4'-(trans-4-(2-(trans-4-n-butylcyclohexyl)ethyl)cyclohexyl)biphenyl
54. 2',3,6'-trifluoro-4-chloro-4'-(trans-4-(2-(trans-4-n-pentylcyclohexyl)ethyl)cyclohexyl)biphenyl
55. 2',3,6'-trifluoro-4-chloro-4'-(trans-4-(2-(trans-4-n-hexylcyclohexyl)ethyl)cyclohexyl)biphenyl
56. 2',3,6'-trifluoro-4-chloro-4'-(trans-4-(2-(trans-4-n-heptylcyclohexyl)ethyl)cyclohexyl)biphenyl
57. 2',3,5,6'-tetrafluoro-4-chloro-4'-(trans-4-(2-(trans-4-methoxycyclohexyl)ethyl)cyclohexyl)biphenyl
58. 2',3,5,6'-tetrafluoro-4-chloro-4'-(trans-4-(2-(trans-4-ethylcyclohexyl)ethyl)cyclohexyl)biphenyl
59. 2',3,5,6'-tetrafluoro-4-chloro-4'-(trans-4-(2-(trans-4-n-propylcyclohexyl)ethyl)cyclohexyl)biphenyl
60. 2',3,5,6'-tetrafluoro-4-chloro-4'-(trans-4-(2-(trans-4-n-butylcyclohexyl)ethyl)cyclohexyl)biphenyl
61. 2',3,5,6'-tetrafluoro-4-chloro-4'-(trans-4-(2-(trans-4-n-pentylcyclohexyl)ethyl)cyclohexyl)biphenyl
62. 2',3,5,6'-tetrafluoro-4-chloro-4'-(trans-4-(2-(trans-4-n-hexylcyclohexyl)ethyl)cyclohexyl)biphenyl
63. 2',3,5,6'-tetrafluoro-4-chloro-4'-(trans-4-(2-(trans-4-n-heptylcyclohexyl)ethyl)cyclohexyl)biphenyl

EXAMPLE 2

Preparation of 3-fluoro-4-chloro-4'-(2-(trans-4-(4-n-propylphenyl)cyclohexyl)ethyl)biphenyl (compound expressed by general formula (I) wherein both ring A and ring C represent 1,4-phenylene, ring B represents trans-1,4-cyclohexylene, $Z_2$ represents —$CH_2CH_2$—, $Z_1$ and $Z_3$ represent covalent bond, $L_1$ represents F atom, $L_2$ represents H atom, and R represents n-propyl group, Compound No. 64)

(1) Metal magnesium in an amount of 12 g was suspended in 50 ml of THF under nitrogen gas stream, and a solution prepared by dissolving 100 g of 4-n-propylbromobenzene in 300 ml of THF was added dropwise and stirred at room temperature for 1 hour. A solution prepared by dissolving 78 g of 1,4-cyclohexanedione-monoethylene ketal in 300 ml of THF was added dropwise thereto and stirred at room temperature for 1 hour. After finishing of the reaction, 500 ml of a saturated aqueous solution of ammonium chloride was added and extracted with 500 ml of ethyl acetate. Organic layer was washed with water and dried over anhydrous magnesium sulfate, and the solvent was distilled off under a reduced pressure to obtain 98 g of 1,1-ethylenedioxy-4-hydroxy-4-(4-n-propylphenyl)cyclohexane.

(2) To 500 ml of toluene was dissolved 98 g of the 1,1-ethylenedioxy-4-hydroxy-4-(4-n-propylphenyl)cyclohexane mentioned above, 5 g of Amberlist 15E was added as catalyst thereto, and stirred under a reflux for 2 hours. After the reaction solution was cooled, the catalyst was filtered off. Organic layer was washed with water and dried over anhydrous magnesium sulfate, and the solvent was distilled off under a reduced pressure to obtain 90 g of 1,1-ethylenedioxy-4-(4-n-propylphenyl)-4-cyclohexene.

(3) To a mixed solution comprising 250 ml of ethanol and 250 ml of toluene was dissolved 80 g of the 1,1-ethylenedioxy-4-(4-n-propylphenyl)-4-cyclohexene, 5 g of palladium/carbon (5%) was added as catalyst thereto, and subjected to a catalytic reduction under hydrogen gas atmosphere. After finishing of the reaction, the catalyst was filtered off and the solvent was distilled off under a reduced pressure to obtain 84 g of 1,1-ethylenedioxy-4-(4-n-propylphenyl)cyclohexane.

(4) To 300 ml of formic acid (99%) was put 84 g of the 1,1-ethylenedioxy-4-(4-n-propylphenyl)cyclohexane mentioned above, and stirred under a reflux for 2 hours. After cooled, the reaction solution was added to 500 ml of water and extracted with 500 ml of ethyl acetate. Organic layer was washed with water and dried over anhydrous magnesium sulfate, and the solvent was distilled off under a reduced pressure to obtain 65.6 g of 4-n-propylphenylcyclohexanone.

(5) Metal magnesium in an amount of 15.3 g was suspended in 100 ml of THF under nitrogen gas stream, and a solution prepared by dissolving 111 g of phenethyl bromide in 300 ml of THF was added dropwise thereto and stirred at room temperature for 1 hour. Solution prepared by dissolving 65.6 g of 4-n-propylphenylcyclohexanone in 200 ml of THF was added dropwise thereto and they were stirred at room temperature for 1 hour. After finishing of the reaction, 300 ml of dilute hydrochloric acid was added and extracted with 500 ml of ethyl acetate. Organic layer was washed with water and dried over anhydrous magnesium sulfate, and the solvent was distilled off under a reduced pressure to obtain 68 g of 4-(4-n-propylphenyl)-1-hydroxy-1-(2-phenyl)ethylcyclohexane.

(6) To 500 ml of toluene was dissolved 68 g of the 4-(4-n-propylphenyl)-1-hydroxy-1-(2-phenyl)ethylcyclohexane, 5 g of Amberlist 15E was added as catalyst to the solution, and the solution was stirred under a reflux for 2 hours. After the reaction solution was cooled, the catalyst was filtered off. Organic layer was washed with water and dried over anhydrous magnesium sulfate, and the solvents was distilled off under a reduced pressure to obtain 57 g of 4-(4-n-propylphenyl)-1-(2-phenyl)ethylcylcohexene.

(7) To a mixed solution comprising 250 ml of ethanol and 250 ml of toluene was dissolved 57 g of the 4-(4-n-propylphenyl)-1-(2-phenyl)ethylcyclohexene mentioned above, 5 g of palladium/carbon (5%) was added as catalyst to the solution, and the solution was subjected to a catalytic reduction in hydrogen gas atmosphere. After finishing of the reaction, the catalyst was filtered off and the solvent was distilled off under a reduced pressure to obtain a yellow oily product. This product was recrystallized from ethanol to obtain 20 g of (2-(trans-4-(4-n-propylphenyl)cyclohexyl)ethyl)benzene.

(8) To a liquid mixture comprising 50 ml of acetic acid, 5 ml of carbon tetrachloride, 5 ml of concentrated sulfuric acid, and 10 ml of water, were added 5.8 g of the (2-(trans-4-(4-n-propylphenyl)cyclohexyl)ethyl)benzene mentioned above, 2.4 g of iodine, and 2 g of iodic acid, and they were stirred under a reflux for 2 hours. After cooled, the mixture was washed with a saturated aqueous solution of sodium thiosulfate. Organic layer was washed with water and dried over anhydrous magnesium sulfate, and the solvent was distilled off under a reduced pressure to obtain a yellow-brown oily product. This product was purified by a column chromatography over an alumina by using heptane as an eluent, and further recrystallized from heptane to obtain 5.8 g of 4-(2-(trans-4-(4-n-propylphenyl)cyclohexyl)ethyl)iodobenzene.

(9) Metal magnesium in an amount of 0.7 g was suspended in 10 ml of THF under nitrogen gas stream, and a solution prepared by dissolving 6 g of 3-fluoro-4-chloro-bromobenzene in 30 ml of THF was added dropwise to the suspension, and the suspension was stirred at room temperature for 1 hour to prepare a solution of Grignard reagent. In 30 ml of THF was dissolved 5.8 g of the 4-(2-(trans-4-(4-n-propylphenyl)cyclohexyl)ethyl)iodobenzene mentioned above, 1 g of palladium chloride was added thereto, and they were stirred under a reflux. Subsequently, the solution of Grignard reagent prepared in the previous procedures was added dropwise thereto, reacted under a heated condition while stirring for 2 hours, the reaction solution thus obtained was added to 20 ml of dilute hydrochloric acid, and the product was extracted with 50 ml of heptane. Organic layer was washed with water and dried over anhydrous magnesium sulfate, and the solvent was distilled off under a reduced pressure to obtain a yellow-brown oily product. This product was purified by a column chromatography over an alumina by using heptane as an eluent, and further recrystallized from heptane to obtain 1.2 g of the subject compound.

According to the procedures mentioned above, following Compounds No. 65 to No. 126 were synthesized:
No.
65. 4-chloro-4'-(2-(trans-4-(4-methylphenyl)cyclohexyl)ethyl)biphenyl
66. 4-chloro-4'-(2-(trans-4-(4-ethylphenyl)cyclohexyl)ethyl)biphenyl
67. 4-chloro-4'-(2-(trans-4-(4-n-propylphenyl)cyclohexyl)ethyl)biphenyl
68. 4-chloro-4'-(2-(trans-4-(4-n-butylphenyl)cyclohexyl)ethyl)biphenyl
69. 4-chloro-4'-(2-(trans-4-(4-n-pentylphenyl)cyclohexyl)ethyl)biphenyl
70. 4-chloro-4'-(2-(trans-4-(4-n-hexylphenyl)cyclohexyl)ethyl)biphenyl
71. 4-chloro-4'-(2-(trans-4-(4-n-nonylphenyl)cyclohexyl)ethyl)biphenyl
72. 3-fluoro-4-chloro-4'-(2-(trans-4-(4-methylphenyl)cyclohexyl)ethyl)biphenyl
73. 3-fluoro-4-chloro-4'-(2-(trans-4-(4-ethylphenyl)cyclohexyl)ethyl)biphenyl
74. 3-fluoro-4-chloro-4'-(2-(trans-4-(4-n-butylphenyl)cyclohexyl)ethyl)biphenyl
75. 3-fluoro-4-chloro-4'-(2-(trans-4-(4-n-pentylphenyl)cyclohexyl)ethyl)biphenyl

CN 88.5, NI 262.4

76. 3-fluoro-4-chloro-4'-(2-(trans-4-(4-n-heptylphenyl)cyclohexyl)ethyl)biphenyl?
77. 3-fluoro-4-chloro-4'-(2-(trans-4-(4-n-heptylphenyl)cyclohexyl)ethyl)biphenyl
78. 2'-fluoro-4-chloro-4'-(2-(trans-4-(4-methylphenyl)cyclohexyl)ethyl)biphenyl
79. 2'-fluoro-4-chloro-4'-(2-(trans-4-(4-ethylphenyl)cyclohexyl)ethyl)biphenyl
80. 2'-fluoro-4-chloro-4'-(2-(trans-4-(4-n-propylphenyl)cyclohexyl)ethyl)biphenyl
81. 2'-fluoro-4-chloro-4'-(2-(trans-4-(4-n-butylphenyl)cyclohexyl)ethyl)biphenyl
82. 2'-fluoro-4-chloro-4'-(2-(trans-4-(4-n-pentylphenyl)cyclohexyl)ethyl)biphenyl
83. 2'-fluoro-4-chloro-4'-(2-(trans-4-(4-n-octylphenyl)cyclohexyl)ethyl)biphenyl
84. 2'-fluoro-4-chloro-4'-(2-(trans-4-(4-n-heptylphenyl)cyclohexyl)ethyl)biphenyl
85. 2',3-difluoro-4-chloro-4'-(2-(trans-4-(4-methylphenyl)cyclohexyl)ethyl)biphenyl
86. 2',3-difluoro-4-chloro-4'-(2-(trans-4-(4-ethylphenyl)cyclohexyl)ethyl)biphenyl
87. 2',3-difluoro-4-chloro-4'-(2-(trans-4-(4-n-propylphenyl)cyclohexyl)ethyl)biphenyl
88. 2',3-difluoro-4-chloro-4'-(2-(trans-4-(4-n-butylphenyl)cyclohexyl)ethyl)biphenyl
89. 2',3-difluoro-4-chloro-4'-(2-(trans-4-(4-n-pentylphenyl)cyclohexyl)ethyl)biphenyl
90. 2',3-difluoro-4-chloro-4'-(2-(trans-4-(4-n-hexylphenyl)cyclohexyl)ethyl)biphenyl
91. 2',3-difluoro-4-chloro-4'-(2-(trans-4-(4-n-heptylphenyl)cyclohexyl)ethyl)biphenyl
92. 3,5-difluoro-4-chloro-4'-(2-(trans-4-(4-methylphenyl)cyclohexyl)ethyl)biphenyl
93. 3,5-difluoro-4-chloro-4'-(2-(trans-4-(4-ethylphenyl)cyclohexyl)ethyl)biphenyl
94. 3,5-difluoro-4-chloro-4'-(2-(trans-4-(4-n-propylphenyl)cyclohexyl)ethyl)biphenyl
95. 3,5-difluoro-4-chloro-4'-(2-(trans-4-(4-n-butylphenyl)cyclohexyl)ethyl)biphenyl
96. 3,5-difluoro-4-chloro-4'-(2-(trans-4-(4-n-pentylphenyl)cyclohexyl)ethyl)biphenyl
97. 3,5-difluoro-4-chloro-4'-(2-(trans-4-(4-n-hexylphenyl)cyclohexyl)ethyl)biphenyl
98. 3,5-difluoro-4-chloro-4'-(2-(trans-4-(4-n-decylphenyl)cyclohexyl)ethyl)biphenyl
99. 2',6'-difluoro-4-chloro-4'-(2-(trans-4-(4-methylphenyl)cyclohexyl)ethyl)biphenyl
100. 2',6'-difluoro-4-chloro-4'-(2-(trans-4-(4-ethylphenyl)cyclohexyl)ethyl)biphenyl
101. 2',6'-difluoro-4-chloro-4'-(2-(trans-4-(4-n-propylphenyl)cyclohexyl)ethyl)biphenyl
102. 2',6'-difluoro-4-chloro-4'-(2-(trans-4-(4-n-butylphenyl)cyclohexyl)ethyl)biphenyl
103. 2',6'-difluoro-4-chloro-4'-(2-(trans-4-(4-n-pentylphenyl)cyclohexyl)ethyl)biphenyl
104. 2',6'-difluoro-4-chloro-4'-(2-(trans-4-(4-n-hexylphenyl)cyclohexyl)ethyl)biphenyl
105. 2',6'-difluoro-4-chloro-4'-(2-(trans-4-(4-n-heptylphenyl)cyclohexyl)ethyl)biphenyl
106. 2',3,5-trifluoro-4-chloro-4'-(2-(trans-4-(4-methylphenyl)cyclohexyl)ethyl)biphenyl
107. 2',3,5-trifluoro-4-chloro-4'-(2-(trans-4-(4-ethylphenyl)cyclohexyl)ethyl)biphenyl
108. 2',3,5-trifluoro-4-chloro-4'-(2-(trans-4-(4-n-propylphenyl)cyclohexyl)ethyl)biphenyl
109. 2',3,5-trifluoro-4-chloro-4'-(2-(trans-4-(4-n-butylphenyl)cyclohexyl)ethyl)biphenyl
110. 2',3,5-trifluoro-4-chloro-4'-(2-(trans-4-(4-n-pentylphenyl)cyclohexyl)ethyl)biphenyl
111. 2',3,5-trifluoro-4-chloro-4'-(2-(trans-4-(4-n-hexylphenyl)cyclohexyl)ethyl)biphenyl
112. 2',3,5-trifluoro-4-chloro-4'-(2-(trans-4-(4-n-heptylphenyl)cyclohexyl)ethyl)biphenyl
113. 2',3,6'-trifluoro-4-chloro-4'-(2-(trans-4-(4-methylphenyl)cyclohexyl)ethyl)biphenyl
114. 2',3,6'-trifluoro-4-chloro-4'-(2-(trans-4-(4-ethylphenyl)cyclohexyl)ethyl)biphenyl
115. 2',3,6'-trifluoro-4-chloro-4'-(2-(trans-4-(4-n-propylphenyl)cyclohexyl)ethyl)biphenyl 116. 2',3,6'-trifluoro-4-chloro-4'-(2-(trans-4-(4-n-butylphenyl)cyclohexyl)ethyl)biphenyl 117. 2',3,6'-trifluoro-4-chloro-4'-(2-(trans-4-(4-n-pentylphenyl)cyclohexyl)ethyl)biphenyl 118. 2',3,6'-trifluoro-4-chloro-4'-(2-(trans-4-(4-n-hexylphenyl)cyclohexyl)ethyl)biphenyl 119, 2',3,6'-trifluoro-4-chloro-4'-(2-(trans-4-(4-n-heptylphenyl)cyclohexyl)ethyl)biphenyl 120. 2',3,5,6'-tetrafluoro-4-chloro-4'-(2-(trans-4-(4-methylphenyl)cyclohexyl)ethyl)biphenyl 121 2',3,5,6'-tetrafluoro-4-chloro-4'-(2-(trans-4-(4-ethylphenyl)cyclohexyl)ethyl)biphenyl 122. 2',3,5,6'-tetrafluoro-4-chloro-4'-(2-(trans-4-(4-n-propylphenyl)cyclohexyl)ethyl)biphenyl 123. 2',3,5,6'-tetrafluoro-4-chloro-4'-(2-(trans-4-(4-n-butylphenyl)cyclohexyl)ethyl)biphenyl 124. 2',3,5,6'-tetrafluoro-4-chloro-4'-(2-(trans-4-(4-n-pentylphenyl)cyclohexyl)ethyl)biphenyl 125. 2',3,5,6'-tetrafluoro-4-chloro-4'-(2-(trans-4-(4-n-hexylphenyl)cyclohexyl)ethyl)biphenyl 126. 2',3,5,6'-tetrafluoro-4-chloro-4'-(2-(trans-4-(4-n-heptylphenyl)cyclohexyl)ethyl)biphenyl

EXAMPLE 3

Preparation of 3-fluoro-4-chloro-4'-(2-(trans-4-(2-(4-n-propylphenyl)ethyl)cyclohexyl)ethyl)biphenyl (compound expressed by general formula (I) wherein both ring A and ring C represent 1,4-phenylene, ring B represents trans-1,4-cyclohexylene, $Z_1$ and $Z_2$ represent —$CH_2CH_2$—, $Z_3$ represents covalent bond, $L_1$ represents F atom, $L_2$ represents H atom, and R represents n-propyl group, Compound No. 127)

(1) Suspension of 114 g of 4-n-propylbenzyltriphenyl phosphonium bromide in 500 ml of THF was stirred under nitrogen gas stream and 32.3 g of potassium-t-butoxide was added thereto at room temperature. After stirred at room temperature for 1 hour, a solution of 31.2 g of 4-formylcyclohexanone in 200 ml of THF was added dropwise to the suspension. After stirred at room temperature for 2 hours, 1 l of water was added thereto and then it was extracted with 1 l of ethyl acetate. Organic layer was washed with water and dried over anhydrous magnesium sulfate, the solvent was distilled off under a reduced pressure, and then 500 ml of heptane was added thereto. Precipitate thus separated was filtered off and purified by a column chromatography over a silica gel by using ethyl acetate/heptane (1/5) as an eluent, and the solvent was distilled off under a reduced pressure to obtain 42 g of 4-(2-(4-n-propylphenyl) ethenyl)cyclohexanone.

(2) In a liquid mixture comprising 200 ml of ethanol and 200 ml of toluene was dissolved 42 g of the 4-(2-(4-n-propylphenyl)ethenyl)cyclohexanone mentioned above, 4 g of palladium/carbon (5%) was added as catalyst, and they were subjected to a catalytic reduction in hydrogen gas atmosphere. After finishing of the reaction, the catalyst was filtered off and the solvent was distilled off under a reduced pressure to obtain 39.8 g of 4-(2-(4-n-propylphenyl)ethyl) cyclohexanone.

(3) Metal magnesium in an amount of 4.7 g was suspended in 25 ml of THF under nitrogen gas atmosphere, and a solution prepared by dissolving 35.5 g of phenethyl bromide in 100 ml of THF was added dropwise to the suspension and stirred at room temperature for 1 hour to prepare a solution of Grignard reagent. To the solution was added dropwise a solution prepared by dissolving 39.8 g of the 4-(2-(4-n-propylphenyl)ethyl)cyclohexanone mentioned above in 300 ml of THF and stirred at room temperature for 1 hour. After finishing of the reaction, 300 ml of dilute hydrochloric acid was added thereto and extracted with 300 ml of ethyl acetate. Organic layer was washed with water and dried over anhydrous magnesium sulfate, and the solvent was distilled off under a reduced pressure to obtain 40 g of 4-(2-(4-n-propylphenyl)ethyl)-1-hydroxy-1-(2-phenyl) ethyl)cyclohexane.

(4) To 200 ml of toluene was dissolved 40 g of the 4-(2-(4-n-propylphenyl)ethyl)-1-hydorxy-1-(2-phenyl) ethylcyclohexane mentioned above, and 4 g of Amberlist 15E was added as catalyst thereto, and they were stirred under a reflux for 2 hours. After the reaction solution was cooled, the catalyst was filtered off. Organic layer was washed with water and dried over anhydrous magnesium sulfate, and the solvent was distilled off under a reduced pressure to obtain 30 g of 4-(2-(4-n-propylphenyl)ethyl)-1-(2-phenyl)ethylcyclohexene.

(5) In a mixed solution comprising 100 ml of ethanol and 100 ml of toluene was dissolved 30 g of the 4-(2-(4-n-propylphenyl)ethyl)-1-(2-phenyl)ethylcyclohexane mentioned above, 3 g of palladium/carbon (5%) was added as catalyst thereto, and they were subjected to a catalytic reduction in hydrogen gas atmosphere. After finishing of the reaction, the catalyst was filtered off and the solvent was distilled off under a reduced pressure to obtain a yellow oily product. This product was recrystallized from ethanol to obtain 26 g of (2-(trans-4-(2-(4-n-propylphenyl)ethyl) cyclohexyl)ethyl)benzene.

(6) To a mixed solution comprising 250 ml of acetic acid, 25 ml of carbon tetrachloride, 25 ml of concentrated sulfuric acid, and 50 ml of water were added 26 g of the (2-(trans-4-(2-(4-n-propylphenyl)ethyl)cyclohexyl)ethyl)benzene mentioned above, 10 g of iodine, and 8.4 g of iodic acid, and they were stirred under a reflux for 2 hours. After cooled, they were washed with a saturated aqueous solution of sodium thiosulfate. Organic layer was washed with water and dried over anhydrous magnesium sulfate, and the solvent was distilled off under a reduced pressure to obtain a yellow-brown oily product. This product was purified by a column chromatography over an alumina by using heptane as an eluent, and then recrystallized from heptane to obtain 10.3 g of 4-(2-(trans-4-(2-(4-n-propylphenyl)ethyl) cyclohexyl)ethyl)iodobenzene.

(7) Metal magnesium in an amount of 12 g was suspended in 10 ml of THF under nitrogen gas stream, and a solution prepared by dissolving 10.3 g of 3-fluoro-4-chloro-bromobenzene in 50 ml of THF was added dropwise thereto and stirred at room temperature for 1 hour to prepare a solution of Grignard reagent. In 50 ml of THF was dissolved 10.6 of the 4-(2-(trans-4-(2-(4-n-propylphenyl)ethyl) cyclohexyl)ethyl)iodobenzene, and 1 g of palladium chloride was added thereto and stirred under a reflux. The solution of Grignard reagent prepared in the previous procedures was added dropwise thereto and reacted while stirring for 2 hours. Reaction solution thus obtained was added to 200 ml of dilute hydrochloric acid, and the product was extracted with 200 ml of heptane. Organic layer was washed with water and dried over anhydrous magnesium sulfate, and the solvent was distilled off under a reduced pressure to obtain a yellow-brown oily product. This product was purified by a column chromatography over an alumina by using heptane as an eluent, and further recrystallized from heptane to obtain 2 g of the subject compound.

According to the procedures mentioned above, the following Compounds No. 128 to 189 were synthesized:

No.

128. 4-chloro-4'-(2-(trans-4-(2-(4-methylphenyl)ethyl) cyclohexyl)ethyl)biphenyl
129. 4-chloro-4'-(2-(trans-4-(2-(4-ethylphenyl)ethyl) cyclohexyl)ethyl)biphenyl
130. 4-chloro-4'-(2-(trans-4-(2-(4-n-propylphenyl)ethyl) cyclohexyl)ethyl)biphenyl
131. 4-chloro-4'-(2-(trans-4-(2-(4-n-butylphenyl)ethyl) cyclohexyl)ethyl)biphenyl
132. 4-chloro-4'-(2-(trans-4-(2-(4-n-pentylphenyl)ethyl) cyclohexyl)ethyl)biphenyl
133. 4-chloro-4'-(2-(trans-4-(2-(4-n-hexylphenyl)ethyl) cyclohexyl)ethyl)biphenyl
134. 4-chloro-4'-(2-(trans-4-(2-(4-n-heptylphenyl)ethyl) cyclohexyl)ethyl)biphenyl
135. 3-fluoro-4-chloro-4'-(2-(trans-4-(2-(4-methylphenyl) ethyl)cyclohexyl)ethyl)biphenyl
136. 3-fluoro-4-chloro-4'-(2-(trans-4-(2-(4-ethylphenyl) ethyl)cyclohexyl)ethyl)biphenyl
137. 3-fluoro-4-chloro-4'-(2-(trans-4-(2-(4-n-butylphenyl) ethyl)cyclohexyl)ethyl)biphenyl
138. 3-fluoro-4-chloro-4'-(2-(trans-4-(2-(4-n-pentylphenyl) ethyl)cyclohexyl)ethyl)biphenyl
139. 3-fluoro-4-chloro-4'-(2-(trans-4-(2-(4-n-hexylphenyl) ethyl)cyclohexyl)ethyl)biphenyl
140. 3-fluoro-4-chloro-4'-(2-(trans-4-(2-(4-n-nonylphenyl) ethyl)cyclohexyl)ethyl)biphenyl
141. 2'-fluoro-4-chloro-4'-(2-(trans-4-(2-(4-methylphenyl) ethyl)cyclohexyl)ethyl)biphenyl
142. 2'-fluoro-4-chloro-4'-(2-(trans-4-(2-(4-ethylphenyl) ethyl)cyclohexyl)ethyl)biphenyl
143. 2'-fluoro-4-chloro-4'-(2-(trans-4-(2-(4-n-propylphenyl) ethyl)cyclohexyl)ethyl)biphenyl
144. 2'-fluoro-4-chloro-4'-(2-(trans-4-(2-(4-n-butylphenyl) ethyl)cyclohexyl)ethyl)biphenyl
145. 2'-fluoro-4-chloro-4'-(2-(trans-4-(2-(4-n-pentylphenyl) ethyl)cyclohexyl)ethyl)biphenyl
146. 2'-fluoro-4-chloro-4'-(2-(trans-4-(2-(4-n-hexylphenyl) ethyl)cyclohexyl)ethyl)biphenyl
147. 2'-fluoro-4-chloro-4'-(2-(trans-4-(2-(4-n-heptylphenyl) ethyl)cyclohexyl)ethyl)biphenyl
148. 2',3-difluoro-4-chloro-4'-(2-(trans-4-(2-(4-methylphenyl)ethyl)cyclohexyl)ethyl)biphenyl
149. 2',3-difluoro-4-chloro-4'-(2-(trans-4-(2-(4-ethylphenyl) ethyl)cyclohexyl)ethyl)biphenyl
150. 2',3-difluoro-4-chloro-4'-(2-(trans-4-(2-(4-n-propylphenyl)ethyl)cyclohexyl)ethyl)biphenyl
151. 2',3-difluoro-4-chloro-4'-(2-(trans-4-(2-(4-n-butylphenyl)ethyl)cyclohexyl)ethyl)biphenyl
152. 2',3-difluoro-4-chloro-4'-(2-(trans-4-(2-(4-n-pentylphenyl)ethyl)cyclohexyl)ethyl)biphenyl
153. 2',3-difluoro-4-chloro-4'-(2-(trans-4-(2-(4-n-hexylphenyl)ethyl)cyclohexyl)ethyl)biphenyl
154. 2',3-difluoro-4-chloro-4'-(2-(trans-4-(2-(4-n-octylphenyl)ethyl)cyclohexyl)ethyl)biphenyl
155. 3,5-difluoro-4-chloro-4'-(2-(trans-4-(2-(4-methylphenyl)ethyl)cyclohexyl)ethyl)biphenyl
156. 3,5-difluoro-4-chloro-4'-(2-(trans-4-(2-(4-ethylphenyl) ethyl)cyclohexyl)ethyl)biphenyl
157. 3,5-difluoro-4-chloro-4'-(2-(trans-4-(2-(4-n-propylphenyl)ethyl)cyclohexyl)ethyl)biphenyl
158. 3,5-difluoro-4-chloro-4'-(2-(trans-4-(2-(4-n-butylphenyl)ethyl)cyclohexyl)ethyl)biphenyl
159. 3,5-difluoro-4-chloro-4'-(2-(trans-4-(2-(4-n-pentylphenyl)ethyl)cyclohexyl)ethyl)biphenyl
160. 3,5-difluoro-4-chloro-4'-(2-(trans-4-(2-(4-n-hexylphenyl)ethyl)cyclohexyl)ethyl)biphenyl
161. 3,5-difluoro-4-chloro-4'-(2-(trans-4-(2-(4-n-heptylphenyl)ethyl)cyclohexyl)ethyl)biphenyl
162. 2',6'-difluoro-4-chloro-4'-(2-(trans-4-(2-(4-methylphenyl)ethyl)cyclohexyl)ethyl)biphenyl
163. 2',6'-difluoro-4-chloro-4'-(2-(trans-4-(2-(4-ethylphenyl)ethyl)cyclohexyl)ethyl)biphenyl
164. 2',6'-difluoro-4-chloro-4'-(2-(trans-4-(2-(4-n-propylphenyl)ethyl)cyclohexyl)ethyl)biphenyl
165. 2',6'-difluoro-4-chloro-4'-(2-(trans-4-(2-(4-n-butylphenyl)ethyl)cyclohexyl)ethyl)biphenyl
166. 2',6'-difluoro-4-chloro-4'-(2-(trans-4-(2-(4-pentylphenyl)ethyl)cyclohexyl)ethyl)biphenyl
167. 2',6'-difluoro-4-chloro-4'-(2-(trans-4-(2-(4-n-hexylphenyl)ethyl)cyclohexyl)ethyl)biphenyl
168. 2',6'-difluoro-4-chloro-4'-(2-(trans-4-(2-(4-n-heptylphenyl)ethyl)cyclohexyl)ethyl)biphenyl
169. 2',3,5,-trifluoro-4-chloro-4'-(2-(trans-4-(2-(4-methylphenyl)ethyl)cyclohexyl)ethyl)biphenyl
170. 2',3,5,-trifluoro-4-chloro-4'-(2-(trans-4-(2-(4-n-ethylphenyl)ethyl)cyclohexyl)ethyl)biphenyl
171. 2',3,5,-trifluoro-4-chloro-4'-(2-(trans-4-(2-(4-n-propylphenyl)ethyl)cyclohexyl)ethyl)biphenyl
172. 2',3,5,-trifluoro-4-chloro-4'-(2-(trans-4-(2-(4-n-butylphenyl)ethyl)cyclohexyl)ethyl)biphenyl
173. 2',3,5,-trifluoro-4-chloro-4'-(2-(trans-4-(2-(4-n-pentylphenyl)ethyl)cyclohexyl)ethyl)biphenyl
174. 2',3,5,-trifluoro-4-chloro-4'-(2-(trans-4-(2-(4-n-decylphenyl)ethyl)cyclohexyl)ethyl)biphenyl
175. 2',3,5,-trifluoro-4-chloro-4'-(2-(trans-4-(2-(4-n-heptylphenyl)ethyl)cyclohexyl)ethyl)biphenyl
176. 2',3,6'-trifluoro-4-chloro-4'-(2-(trans-4-(2-(4-methylphenyl)ethyl)cyclohexyl)ethyl)biphenyl
177. 2',3,6'-trifluoro-4-chloro-4'-(2-(trans-4-(2-(4-ethylphenyl)ethyl)cyclohexyl)ethyl)biphenyl
178. 2',3,6'-trifluoro-4-chloro-4'-(2-(trans-4-(2-(4-n-propylphenyl)ethyl)cyclohexyl)ethyl)biphenyl
179. 2',3,6'-trifluoro-4-chloro-4'-(2-(trans-4-(2-(4-n-butylphenyl)ethyl)cyclohexyl)ethyl)biphenyl
180. 2',3,6'-trifluoro-4-chloro-4'-(2-(trans-4-(2-(4-n-pentylphenyl)ethyl)cyclohexyl)ethyl)biphenyl
181. 2',3,6'-trifluoro-4-chloro-4'-(2-(trans-4-(2-(4-n-hexylphenyl)ethyl)cyclohexyl)ethyl)biphenyl
182. 2',3,6'-trifluoro-4-chloro-4'-(2-(trans-4-(2-(4-n-heptylphenyl)ethyl)cyclohexyl)ethyl)biphenyl
183. 2',3,5,6'-tetrafluoro-4-chloro-4'-(2-(trans-4-(2-(4-methylphenyl)ethyl)cyclohexyl)ethyl)biphenyl
184. 2',3,5,6'-tetrafluoro-4-chloro-4'-(2-(trans-4-(2-(4-ethylphenyl)ethyl)cyclohexyl)ethyl)biphenyl
185. 2',3,5,6'-tetrafluoro-4-chloro-4'-(2-(trans-4-(2-(4-n-propylphenyl)ethyl)cyclohexyl)ethyl)biphenyl
186. 2',3,5,6'-tetrafluoro-4-chloro-4'-(2-(trans-4-(2-(4-n-butylphenyl)ethyl)cyclohexyl)ethyl)biphenyl
187. 2',3,5,6'-tetrafluoro-4-chloro-4'-(2-(trans-4-(2-(4-n-pentylphenyl)ethyl)cyclohexyl)ethyl)biphenyl
188. 2',3,5,6'-tetrafluoro-4-chloro-4'-(2-(trans-4-(2-(4-n-hexylphenyl)ethyl)cyclohexyl)ethyl)biphenyl
189. 2',3,5,6'-tetrafluoro-4-chloro-4'-(2-(trans-4-(2-(4-n-heptylphenyl)ethyl)cyclohexyl)ethyl)biphenyl

EXAMPLE 4

Preparation of 4-(2-(4-(2-(trans-4-(4-n-propylphenyl) cyclohexyl)ethyl)phenyl)ethyl)chlorobenzene (compound expressed by general formula (I) wherein both ring A and ring C represent 1,4-phenylene, ring B represents trans-1,4-cyclohexylene, both $Z_2$ and $Z_3$ represent —$CH_2CH_2$—, $Z_1$ represents covalent bond, both $L_1$ and $L_2$ represent H atom, and R represents n-propyl group, Compound No. 190)

(1) After 27.6 g of the (2-(trans-4-(4-n-propylphenyl) cyclohexyl)ethyl)benzene obtained in (7) of Example 2 was dissolved in 200 ml of methylene chloride, it was cooled down to 0° C., and 24 g of aluminum chloride was added to the solution and stirred. Oxalyl chloride in an amount of 22.8 g was added dropwise little by little to the solution, and after the temperature of the solution was raised up to room temperature, it was stirred for 2 hours. After finishing of the reaction, it was added to 500 ml of water and extracted with 200 ml of methylene chloride. Organic layer was washed with water and dried over anhydrous magnesium sulfate, and the solvent was distilled off under a reduced pressure to obtain 20 g of 4-(2-(trans-4-(4-n-propylphenyl)cyclohexyl) ethyl)benzoyl chloride.

(2) To 500 ml of toluene were added 5 ml of ethanol and 8.5 g of pyridine, and stirred. A liquid mixture of 19.8 g of the 4-(2-(trans-4-(4-n-propylphenyl)cyclohexyl)ethyl) benzoyl chloride mentioned above in 100 ml of toluene was added dropwise thereto and stirred under reflux for 2 hours. After cooled, the reaction solution was added to 500 ml of water and extracted with 200 ml of toluene. Organic layer was washed with water and dried over anhydrous magnesium sulfate, and the solvent was distilled off under a reduced pressure to obtain 16.2 g of 4-(2-(trans-4-(4-n-propylphenyl)cyclohexyl)ethyl)ethylbenzoate.

(3) Under cooled condition with ice, 1.6 g of lithium aluminum hydride was added little by little to 100 ml of THF and stirred. A liquid mixture of 16.2 g of the 4-(2-(trans-4-(4-n-propylphenyl)cyclohexyl)ethyl)ethylbenzoate mentioned above in 200 ml of THF was added dropwise thereto. It was stirred as it was cooled with ice for 2 hours, and then 200 ml of ethyl acetate was added dropwise thereto. The reaction solution was added to 200 ml of dilute hydrochloric acid cooled with ice and extracted with 200 ml of ethyl acetate. Organic layer was washed with water and dried over anhydrous magnesium sulfate, and the solvent was distilled off under a reduced pressure to obtain 10.1 g of 4-(2-(trans-4-(4-n-propylphenyl)cyclohexyl)ethyl)benzyl alcohol.

(4) Dicyclohexylcarbodiimide in an amount of 12.9 g was suspended in 200 ml of methylene chloride and stirred. To the suspension was added dropwise a solution prepared by dissolving 10.1 g of the 4-(2-(trans-4-(4-n-propylphenyl) cyclohexyl)ethyl)benzyl alcohol mentioned above in 200 ml of methylene chloride, and stirred at room temperature for 2 hours. Crude reaction solution thus obtained was purified by a column chromatography over a silica gel, and then the solvent was distilled off under a reduced pressure to obtain 2.8 g of 4-(2-(trans-4-(4-n-propylphenyl)cyclohexyl)ethyl) benzaldehyde.

(5) Suspension of 11.8 g of 4-chlorobenzyltriphenylphosphonium bromide in 100 ml of THF was stirred under nitrogen gas stream, and 2.8 g of potassium-t-butoxide was added to the suspension at room temperature. After stirred at room temperature for 1 hour, a solution of 7 g of the 4-(2-(trans-4-(4-n-propylphenyl)cyclohexyl)ethyl) benzaldehyde in 50 ml of THF was added dropwise. After stirred at room temperature for 2 hours, 300 ml of water was added and extracted with 300 ml of ethyl acetate. Organic layer was washed with water and dried over anhydrous magnesium sulfate, the solvent was distilled off under a reduced pressure, and then 200 ml of heptane was added. Precipitate thus separated was filtered off, and subjected to a column chromatography over a silica gel by using ethyl acetate/heptane (1/5) as an eluent. Solvent was distilled off under a reduced pressure to obtain 5.6 g 4-(2-(4-(2-(trans-4-(4-n-propylphenyl)cyclohexyl)ethyl)phenyl)ethenyl) chlorobenzene.

(6) To a mixed solution comprising 25 ml of ethanol and 25 ml of toluene was dissolved 5.6 g of the 4-(2-(4-(2-(trans-4-(4-n-propylphenyl)cyclohexyl)ethyl)phenyl)ethenyl) chlorobenzene mentioned above, 0.5 g of palladium/barium sulfate was added as catalyst thereto, and subjected to a catalytic reduction in hydrogen gas atmosphere. After finishing of the reaction, the catalyst was filtered off and the solvent was distilled off under a reduced pressure to obtain 2.8 g of the subject compound.

According to the procedures mentioned above, the following Compounds No. 191 to No. 252 were synthesized:

No.
191. 4-(2-(4-(2-(trans-4-(4-methylphenyl)cyclohexyl)ethyl) phenyl)ethyl)chlorobenzene
192. 4-(2-(4-(2-(trans-4-(4-ethylphenyl)cyclohexyl)ethyl) phenyl)ethyl)chlorobenzene
193. 4-(2-(4-(2-(trans-4-(4-n-butylphenyl)cyclohexyl)ethyl) phenyl)ethyl)chlorobenzene
194. 4-(2-(4-(2-(trans-4-(4-n-pentylphenyl)cyclohexyl) ethyl)phenyl)ethyl)chlorobenzene
195. 4-(2-(4-(2-(trans-4-(4-n-hexylphenyl)cyclohexyl) ethyl)phenyl)ethyl)chlorobenzene
196. 4-(2-(4-(2-(trans-4-(4-n-heptylphenyl)cyclohexyl) ethyl)phenyl)ethyl)chlorobenzene
197. 2-fluoro-4-(2-(4-(2-(trans-4-(4-methylphenyl) cyclohexyl)ethyl)phenyl)ethyl)chlorobenzene
198. 2-fluoro-4-(2-(4-(2-(trans-4-(4-ethylphenyl) cyclohexyl)ethyl)phenyl)ethyl)chlorobenzene
199. 2-fluoro-4-(2-(4-(2-(trans-4-(4-n-propylphenyl) cyclohexyl)ethyl)phenyl)ethyl)chlorobenzene
200. 2-fluoro-4-(2-(4-(2-(trans-4-(4-n-butylphenyl) cyclohexyl)ethyl)phenyl)ethyl)chlorobenzene
201. 2-fluoro-4-(2-(4-(2-(trans-4-(4-n-pentylphenyl) cyclohexyl)ethyl)phenyl)ethyl)chlorobenzene
202. 2-fluoro-4-(2-(4-(2-(trans-4-(4-n hexylphenyl) cyclohexyl)ethyl)phenyl)ethyl)chlorobenzene
203. 2-fluoro-4-(2-(4-(2-(trans-4-(4-n-nonylphenyl) cyclohexyl)ethyl)phenyl)ethyl)chlorobenzene
204. 4-(2-(2-fluoro-4-(2-(trans-4-(4-methylphenyl) cyclohexyl)ethyl)phenyl)ethyl)chlorobenzene
205. 4-(2-(2-fluoro-4-(2-(trans-4-(4-ethylphenyl) cyclohexyl)ethyl)phenyl)ethyl)chlorobenzene
206. 4-(2-(2-fluoro-4-(2-(trans-4-(4-n-propylphenyl) cyclohexyl)ethyl)phenyl)ethyl)chlorobenzene
207. 4-(2-(2-fluoro-4-(2-(trans-4-(4-n-butylphenyl) cyclohexyl)ethyl)phenyl)ethyl)chlorobenzene
208. 4-(2-(2-fluoro-4-(2-(trans-4-(4-n-pentylphenyl) cyclohexyl)ethyl)phenyl)ethyl)chlorobenzene
209. 4-(2-(2-fluoro-4-(2-(trans-4-(4-n-hexylphenyl) cyclohexyl)ethyl)phenyl)ethyl)chlorobenzene
210. 4-(2-(2-fluoro-4-(2-(trans-4-(4-n-heptylphenyl) cyclohexyl)ethyl)phenyl)ethyl)chlorobenzene
211. 2-fluoro-4-(2-(2-fluoro-4-(2-(trans-4-(4-methylphenyl) cyclohexyl)ethyl)phenyl)ethyl)chlorobenzene
212. 2-fluoro-4-(2-(2-fluoro-4-(2-(trans-4-(4-ethylphenyl) cyclohexyl)ethyl)phenyl)ethyl)chlorobenzene
213. 2-fluoro-4-(2-(2-fluoro-4-(2-(trans-4-(4-n-propylphenyl)cyclohexyl)ethyl)phenyl)ethyl) chlorobenzene
214. 2-fluoro-4-(2-(2-fluoro-4-(2-(trans-4-(4-n-butylphenyl)cyclohexyl)ethyl)phenyl)ethyl) chlorobenzene
215. 2-fluoro-4-(2-(2-fluoro-4-(2-(trans-4-(4-n-pentylphenyl)cyclohexyl)ethyl)phenyl)ethyl) chlorobenzene
216. 2-fluoro-4-(2-(2-fluoro-4-(2-(trans-4-(4-n-hexylphenyl)cyclohexyl)ethyl)phenyl)ethyl) chlorobenzene
217. 2-fluoro-4-(2-(2-fluoro-4-(2-(trans-4-(4-n-octylphenyl) cyclohexyl)ethyl)phenyl)ethyl)chlorobenzene 218. 2,6-difluoro-4-(2-(4-(2-(trans-4-(4-methylphenyl)cyclohexyl)ethyl)phenyl)ethyl)chlorobenzene
219. 2,6-difluoro-4-(2-(4-(2-(trans-4-(4-ethylphenyl)cyclohexyl)ethyl)phenyl)ethyl)chlorobenzene
220. 2,6-difluoro-4-(2-(4-(2-(trans-4-(4-n-propylphenyl)cyclohexyl)ethyl)phenyl)ethyl)chlorobenzene
221. 2,6-difluoro-4-(2-(4-(2-(trans-4-(4-n-butylphenyl)cyclohexyl)ethyl)phenyl)ethyl)chlorobenzene
222. 2,6-difluoro-4-(2-(4-(2-(trans-4-(4-n-pentylphenyl)cyclohexyl)ethyl)phenyl)ethyl)chlorobenzene
223. 2,6-difluoro-4-(2-(4-(2-(trans-4-(4-n-hexylphenyl)cyclohexyl)ethyl)phenyl)ethyl)chlorobenzene
224. 2,6-difluoro-4-(2-(4-(2-(trans-4-(4-n-heptylphenyl)cyclohexyl)ethyl)phenyl)ethyl)chlorobenzene
225. 4-(2-(2,6-difluoro-4-(2-(trans-4-(4-methylphenyl)cyclohexyl)ethyl)phenyl)ethyl)chlorobenzene
226. 4-(2-(2,6-difluoro-4-(2-(trans-4-(4-ethylphenyl)cyclohexyl)ethyl)phenyl)ethyl)chlorobenzene
227. 4-(2-(2,6-difluoro-4-(2-(trans-4-(4-n-propylphenyl)cyclohexyl)ethyl)phenyl)ethyl)chlorobenzene
228. 4-(2-(2,6-difluoro-4-(2-(trans-4-(4-n-butylphenyl)cyclohexyl)ethyl)phenyl)ethyl)chlorobenzene
229. 4-(2-(2,6-difluoro-4-(2-(trans-4-(4-n-pentylphenyl)cyclohexyl)ethyl)phenyl)ethyl)chlorobenzene
230. 4-(2-(2,6-difluoro-4-(2-(trans-4-(4-n-hexylphenyl)cyclohexyl)ethyl)phenyl)ethyl)chlorobenzene
231. 4-(2-(2,6-difluoro-4-(2-(trans-4-(4-n-decylphenyl)cyclohexyl)ethyl)phenyl)ethyl)chlorobenzene
232. 2,6-difluoro-4-(2-(2-fluoro-4-(2-(trans-4-(4-methylphenyl)cyclohexyl)ethyl)phenyl)ethyl)chlorobenzene
233. 2,6-difluoro-4-(2-(2-fluoro-4-(2-(trans-4-(4-ethylphenyl)cyclohexyl)ethyl)phenyl)ethyl)chlorobenzene
234. 2,6-difluoro-4-(2-(2-fluoro-4-(2-(trans-4-(4-n-propylphenyl)cyclohexyl)ethyl)phenyl)ethyl)chlorobenzene
235. 2,6-difluoro-4-(2-(2-fluoro-4-(2-(trans-4-(4-n-butylphenyl)cyclohexyl)ethyl)phenyl)ethyl)chlorobenzene
236. 2,6-difluoro-4-(2-(2-fluoro-4-(2-(trans-4-(4-n-pentylphenyl)cyclohexyl)ethyl)phenyl)ethyl)chlorobenzene
237. 2,6-difluoro-4-(2-(2-fluoro-4-(2-(trans-4-(4-n-hexylphenyl)cyclohexyl)ethyl)phenyl)ethyl)chlorobenzene
238. 2,6-difluoro-4-(2-(2-fluoro-4-(2-(trans-4-(4-n-heptylphenyl)cyclohexyl)ethyl)phenyl)ethyl)chlorobenzene
239. 2-fluoro-4-(2-(2,6-difluoro-4-(2-(trans-4-(4-methylphenyl)cyclohexyl)ethyl)phenyl)ethyl)chlorobenzene
240. 2-fluoro-4-(2-(2,6-difluoro-4-(2-(trans-4-(4-ethylphenyl)cyclohexyl)ethyl)phenyl)ethyl)chlorobenzene
241. 2-fluoro-4-(2-(2,6-difluoro-4-(2-(trans-4-(4-n-propylphenyl)cyclohexyl)ethyl)phenyl)ethyl)chlorobenzene
242. 2-fluoro-4-(2-(2,6-difluoro-4-(2-(trans-4-(4-n-butylphenyl)cyclohexyl)ethyl)phenyl)ethyl)chlorobenzene
243. 2-fluoro-4-(2-(2,6-difluoro-4-(2-(trans-4-(4-n-pentylphenyl)cyclohexyl)ethyl)phenyl)ethyl)chlorobenzene
244. 2-fluoro-4-(2-(2,6-difluoro-4-(2-(trans-4-(4-n-hexylphenyl)cyclohexyl)ethyl)phenyl)ethyl)chlorobenzene
245. 2-fluoro-4-(2-(2,6-difluoro-4-(2-(trans-4-(4-n-heptylphenyl)cyclohexyl)ethyl)phenyl)ethyl)chlorobenzene
246. 2,6-difluoro-4-(2-(2,6-difluoro-4-(2-(trans-4-(4-methylphenyl)cyclohexyl)ethyl)phenyl)ethyl)chlorobenzene
247. 2,6-difluoro-4-(2-(2,6-difluoro-4-(2-(trans-4-(4-ethylphenyl)cyclohexyl)ethyl)phenyl)ethyl)chlorobenzene
248. 2,6-difluoro-4-(2-(2,6-difluoro-4-(2-(trans-4-(4-n-propylphenyl)cyclohexyl)ethyl)phenyl)ethyl)chlorobenzene
249. 2,6-difluoro-4-(2-(2,6-difluoro-4-(2-(trans-4-(4-n-butylphenyl)cyclohexyl)ethyl)phenyl)ethyl)chlorobenzene
250. 2,6-difluoro-4-(2-(2,6-difluoro-4-(2-(trans-4-(4-n-pentylphenyl)cyclohexyl)ethyl)phenyl)ethyl)chlorobenzene
251. 2,6-difluoro-4-(2-(2,6-difluoro-4-(2-(trans-4-(4-n-hexylphenyl)cyclohexyl)ethyl)phenyl)ethyl)chlorobenzene
252. 2,6-difluoro-4-(2-(2,6-difluoro-4-(2-(trans-4-(4-n-heptylphenyl)cyclohexyl)ethyl)phenyl)ethyl)chlorobenzene

EXAMPLE 5

Preparation of 4-(2-(4-(trans-4-(2-(trans-4-n-propylcyclohexyl)ethyl)cyclohexyl)phenyl)ethyl)chlorobenzene (compound expressed by general formula (I) wherein ring C represents 1,4-phenylene, both ring A and ring B represent trans-1,4-cyclohexylene, both $Z_1$ and $Z_3$ represent —$CH_2CH_2$—, $Z_2$ represents single bond, $L_1$ and $L_2$ represent H atom, and R represents n-propyl group, Compound No. 253)

(1) Solution prepared by dissolving 25.5 g of (trans-4-(2-(trans-4-n-propylcyclohexyl)ethyl)cyclohexyl)benzene in 200 ml of methylene chloride was cooled to 0° C., and 24 g of aluminum chloride was added to the solution and stirred. To the solution was added dropwise little by little 21.5 g of oxalyl chloride, and its temperature was raised to room temperature and stirred for 2 hours. After finishing of the reaction, it was added to 500 ml of water and extracted with 200 ml of methylene chloride. Organic layer was washed with water and dried over anhydrous magnesium sulfate, and the solvent was distilled off under a reduced pressure to obtain 18 g of (trans-4-(2-(trans-4-n-propylcyclohexyl)ethyl)cyclohexyl)benzoylchloride.

(2) To 500 ml of toluene was added 5 ml of ethanol and 8 g of pyridine, and they were stirred. Liquid mixture of 18.5 g of the (trans-4-(2-(trans-4-n-propylcyclohexyl)ethyl)cyclohexyl)benzoylchloride mentioned above and 10 ml of toluene was added dropwise thereto, and stirred under a reflux for 2 hours. After it was cooled, the reaction solution was added to 500 ml of water and extracted with 500 ml of toluene. Organic layer was washed with water and dried over anhydrous magnesium sulfate, and the solvent was distilled off under a reduced pressure to obtain 15.5 g of (trans-4-(2-(trans-4-n-propylcyclohexyl)ethyl)cyclohexyl) ethylbenzoate.

(3) Under cooled condition with ice, 1.4 g of lithium aluminum hydride was added little by little to 100 ml of THF and stirred. Liquid mixture of 15.5 g of the (trans-4-(2-(trans-4-n-propylcyclohexyl)ethyl)cyclohexyl) ethylbenzoate mentioned above and 200 ml of THF was added dropwise thereto, stirred while cooling with ice for 2 hours, and then 200 ml of ethyl acetate was added dropwise thereto. The reaction solution was added to 200 ml of dilute hydrochloric acid cooled with ice, and extracted with 200 ml of ethyl acetate. Organic layer was washed with water and dried over anhydrous magnesium sulfate, and the solvent was distilled off under a reduced pressure to obtain 9.7 g of (trans-4-(2-(trans-4-n-propylcyclohexyl)ethyl)cyclohexyl) benzyl alcohol.

(4) Dicyclohexylcarbodiimide in an amount of 12.0 g was suspended in 200 ml of methylene chloride and stirred. Solution prepared by dissolving 9.7 g of the (trans-4-(2-(trans-4-n-propylcyclohexyl)ethyl)cyclohexyl)benzyl alcohol in 200 ml of ethylene chloride was added dropwise and stirred at room temperature for 2 hours. Crude reaction solution was purified by a column chromatography over a silica gel. Solvent was distilled off to obtain 6 g of (trans-4-(2-(trans-4-n-propylcyclohexyl)ethyl)cyclohexyl) benzaldehyde.

(5) Suspension of 10.7 g of 4-chlorobenzyltriphenyl phosphonium bromide in 100 ml of THF was stirred under nitrogen gas stream and 2.5 g of potassium-t-butoxide was added thereto at room temperature. After stirred at room temperature for 1 hour, a solution prepared by dissolving 6 g of the (trans-4-(2-(trans-4-n-propylcyclohexyl)ethyl) cyclohexyl)benzaldehyde mentioned above in 50 ml of THF was added dropwise. After stirred at room temperature for 2 hours, 300 ml of water was added and extracted with 300 ml of ethyl acetate. Organic layer was washed with water and dried over anhydrous magnesium sulfate, the solvent was distilled off under a reduced pressure, and then 250 ml of heptane was added thereto. Precipitate thus separated was filtered off and purified by a column chromatography over silica gel by using ethyl acetate/heptane (1/5) as an eluent. Solvent was distilled off under a reduced pressure to obtain 5.4 g of 4-(2-(4-(trans-4-(2-(trans-4-n-propylcyclohexyl) ethyl)cyclohexyl)phenyl)ethenyl)chlorobenzene.

(6) To 25 ml of ethanol and 25 ml of toluene, was dissolved 5.4 g of the 4-(2-(4-(trans-4-(2-(trans-4-n-propylcyclohexyl)ethyl)cyclohexyl)phenyl)ethenyl) chlorobenzene mentioned above, 0.5 g of palladium/barium sulfate was added as catalyst thereto, and then subjected to a catalytic reduction in hydrogen gas atmosphere. After finishing of the reaction, the catalyst was filtered off and the solvent was distilled off under a reduced pressure to obtain a light yellow oily product. This product was recrystallized from heptane to obtain 2.0 g of the subject compound.

According to the procedures mentioned above, the following Compounds No. 254 to 315 were synthesized:
No.
254. 4-(2-(4-(trans-4-(2-(trans-4-methylcyclohexyl)ethyl) cyclohexyl)phenyl)ethyl)chlorobenzene
255. 4-(2-(4-(trans-4-(2-(trans-4-ethylcyclohexyl)ethyl) cyclohexyl)phenyl)ethyl)chlorobenzene
256. 4-(2-(4-(trans-4-(2-(trans-4-n-butylcyclohexyl)ethyl) cyclohexyl)phenyl)ethyl)chlorobenzene
257. 4-(2-(4-(trans-4-(2-(trans-4-n-pentylcyclohexyl)ethyl) cyclohexyl)phenyl)ethyl)chlorobenzene
258. 4-(2-(4-(trans-4-(2-(trans-4-n-hexylcyclohexyl)ethyl) cyclohexyl)phenyl)ethyl)chlorobenzene
259. 4-(2-(4-(trans-4-(2-(trans-4-n-heptylcyclohexyl)ethyl) cyclohexyl)phenyl)ethyl)chlorobenzene
260. 2-fluoro-4-(2-(4-(trans-4-(2-(trans-4-methylcyclohexyl)ethyl)cyclohexyl)phenyl)ethyl) chlorobenzene
261. 2-fluoro-4-(2-(4-(trans-4-(2-(trans-4-ethylcyclohexyl) ethyl)cyclohexyl)phenyl)ethyl)chlorobenzene
262. 2-fluoro-4-(2-(4-(trans-4-(2-(trans-4-n-propylcyclohexyl)ethyl)cyclohexyl)phenyl)ethyl) chlorobenzene
263. 2-fluoro-4-(2-(4-(trans-4-(2-(trans-4-n-butylcyclohexyl)ethyl)cyclohexyl)phenyl)ethyl) chlorobenzene
264. 2-fluoro-4-(2-(4-(trans-4-(2-(trans-4-n-pentylcyclohexyl)ethyl)cyclohexyl)phenyl)ethyl) chlorobenzene
265. 2-fluoro-4-(2-(4-(trans-4-(2-(trans-4-n-hexylcyclohexyl)ethyl)cyclohexyl)phenyl)ethyl) chlorobenzene
266. 2-fluoro-4-(2-(4-(trans-4-(2-(trans-4-n-heptylcyclohexyl)ethyl)cyclohexyl)phenyl)ethyl) chlorobenzene
267. 4-(2-(2-fluoro-4-(2-(trans-4-methylcyclohexyl)ethyl) cyclohexyl)phenyl)ethyl)chlorobenzene
268. 4-(2-(2-fluoro-4-(2-(trans-4-ethylcyclohexyl)ethyl) cyclohexyl)phenyl)ethyl)chlorobenzene
269. 4-(2-(2-fluoro-4-(2-(trans-4-n-propylcyclohexyl)ethyl) cyclohexyl)phenyl)ethyl)chlorobenzene
270. 4-(2-(2-fluoro-4-(2-(trans-4-n-butylcyclohexyl)ethyl) cyclohexyl)phenyl)ethyl)chlorobenzene
271. 4-(2-(2-fluoro-4-(2-(trans-4-n-pentylcyclohexyl)ethyl) cyclohexyl)phenyl)ethyl)chlorobenzene
272. 4-(2-(2-fluoro-4-(2-(trans-4-n-nonylcyclohexyl)ethyl) cyclohexyl)phenyl)ethyl)chlorobenzene
273. 4-(2-(2-fluoro-4-(2-(trans-4-n-heptylcyclohexyl)ethyl) cyclohexyl)phenyl)ethyl)chlorobenzene
274. 2-fluoro-4-(2-(2-fluoro-4-(trans-4-(2-(trans-4-methylcyclohexyl)ethyl)cyclohexyl)phenyl)ethyl) chlorobenzene
275. 2-fluoro-4-(2-(2-fluoro-4-(trans-4-(2-(trans-4-ethylcyclohexyl)ethyl)cyclohexyl)phenyl)ethyl) chlorobenzene
276. 2-fluoro-4-(2-(2-fluoro-4-(trans-4-(2-(trans-4-n-propylcyclohexyl ethyl cyclohexyl)phenyl)ethyl) chlorobenzene
277. 2-fluoro-4-(2-(2-fluoro-4-(trans-4-(2-(trans-4-n-butylcyclohexyl)ethyl)cyclohexyl)phenyl)ethyl) chlorobenzene
278. 2-fluoro-4-(2-(2-fluoro-4-(trans-4-(2-(trans-4-n-pentylcyclohexyl)ethyl)cyclohexyl)phenyl)ethyl) chlorobenzene
279. 2-fluoro-4-(2-(2-fluoro-4-(trans-4-(2-(trans-4-n-hexylcyclohexyl)ethyl)cyclohexyl)phenyl)ethyl) chlorobenzene
280. 2-fluoro-4-(2-(2-fluoro-4-(trans-4-(2-(trans-4-n-octylcyclohexyl)ethyl)cyclohexyl)phenyl)ethyl) chlorobenzene
281. 2,6-difluoro-4-(2-(4-(trans-4-(2-(trans-4-methylcyclohexyl)ethyl)cyclohexyl)phenyl)ethyl) chlorobenzene
282. 2,6-difluoro-4-(2-(4-(trans-4-(2-(trans-4-ethylcyclohexyl)ethyl)cyclohexyl)phenyl)ethyl) chlorobenzene
283. 2,6-difluoro-4-(2-(4-(trans-4-(2-(trans-4-n-propylcyclohexyl)ethyl)cyclohexyl)phenyl)ethyl) chlorobenzene
284. 2,6-difluoro-4-(2-(4-(trans-4-(2-(trans-4-n-butylcyclohexyl)ethyl)cyclohexyl)phenyl)ethyl) chlorobenzene
285. 2,6-difluoro-4-(2-(4-(trans-4-(2-(trans-4-n-pentylcyclohexyl)ethyl)cyclohexyl)phenyl)ethyl) chlorobenzene
286. 2,6-difluoro-4-(2-(4-(trans-4-(2-(trans-4-n-hexylcyclohexyl)ethyl)cyclohexyl)phenyl)ethyl) chlorobenzene
287. 2,6-difluoro-4-(2-(4-(trans-4-(2-(trans-4-n-heptylcyclohexyl)ethyl)cyclohexyl)phenyl)ethyl) chlorobenzene 288. 4-(2-(2,6-difluoro-4-(trans-4-(2-(trans-4-methylcyclohexyl)ethyl)cyclohexyl)phenyl)ethyl) chlorobenzene
289. 4-(2-(2,6-difluoro-4-(trans-4-(2-(trans-4-ethylcyclohexyl)ethyl)cyclohexyl)phenyl)ethyl) chlorobenzene
290. 4-(2-(2,6-difluoro-4-(trans-4-(2-(trans-4-n-propylcyclohexyl)ethyl)cyclohexyl)phenyl)ethyl) chlorobenzene
291. 4-(2-(2,6-difluoro-4-(trans-4-(2-(trans-4-n-butylcyclohexyl)ethyl)cyclohexyl)phenyl)ethyl) chlorobenzene
292. 4-(2-(2,6-difluoro-4-(trans-4-(2-(trans-4-n-pentylcyclohexyl)ethyl)cyclohexyl)phenyl)ethyl) chlorobenzene
293. 4-(2-(2,6-difluoro-4-(trans-4-(2-(trans-4-n-decylcyclohexyl)ethyl)cyclohexyl)phenyl)ethyl) chlorobenzene
294. 4-(2-(2,6-difluoro-4-(trans-4-(2-(trans-4-n-heptylcyclohexyl)ethyl)cyclohexyl)phenyl)ethyl) chlorobenzene
295. 2,6-difluoro-4-(2-(2-fluoro-4-(trans-4-(2-(trans-4-methylcyclohexyl)ethyl)cyclohexyl)phenyl)ethyl) chlorobenzene
296. 2,6-difluoro-4-(2-(2-fluoro-4-(trans-4-(2-(trans-4-ethylcyclohexyl)ethyl)cyclohexyl)phenyl)ethyl) chlorobenzene
297. 2,6-difluoro-4-(2-(2-fluoro-4-(trans-4-(2-(trans-4-n-propylcyclohexyl)ethyl)cyclohexyl)phenyl)ethyl) chlorobenzene
298. 2,6-difluoro-4-(2-(2-fluoro-4-(trans-4-(2-(trans-4-n-butylcyclohexyl)ethyl)cyclohexyl)phenyl)ethyl) chlorobenzene
299. 2,6-difluoro-4-(2-(2-fluoro-4-(trans-4-(2-(trans-4-n-pentylcyclohexyl)ethyl)cyclohexyl)phenyl)ethyl) chlorobenzene
300. 2,6-difluoro-4-(2-(2-fluoro-4-(trans-4-(2-(trans-4-n-hexylcyclohexyl)ethyl)cyclohexyl)phenyl)ethyl) chlorobenzene
301. 2,6-difluoro-4-(2-(2-fluoro-4-(trans-4-(2-(trans-4-n-heptylcyclohexyl)ethyl)cyclohexyl)phenyl)ethyl) chlorobenzene
302. 2-fluoro-4-(2-(2,6-difluoro-4-(trans-4-(2-(trans-4-methylcyclohexyl)ethyl)cyclohexyl)phenyl)ethyl) chlorobenzene
303. 2-fluoro-4-(2-(2,6-difluoro-4-(trans-4-(2-(trans-4-ethylcyclohexyl)ethyl)cyclohexyl)phenyl)ethyl) chlorobenzene
304. 2-fluoro-4-(2-(2,6-difluoro-4-(trans-4-(2-(trans-4-n-propylcyclohexyl)ethyl)cyclohexyl)phenyl)ethyl) chlorobenzene
305. 2-fluoro-4-(2-(2,6-difluoro-4-(trans-4-(2-(trans-4-n-butylcyclohexyl)ethyl)cyclohexyl)phenyl)ethyl) chlorobenzene
306. 2-fluoro-4-(2-(2,6-difluoro-4-(trans-4-(2-(trans-4-n-pentylcyclohexyl)ethyl)cyclohexyl)phenyl)ethyl) chlorobenzene
307. 2-fluoro-4-(2-(2,6-difluoro-4-(trans-4-(2-(trans-4-n-hexylcyclohexyl)ethyl)cyclohexyl)phenyl)ethyl) chlorobenzene
308. 2-fluoro-4-(2-(2,6-difluoro-4-(trans-4-(2-(trans-4-n-heptylcyclohexyl)ethyl)cyclohexyl)phenyl)ethyl) chlorobenzene
309. 2,6-difluoro-4-(2-(2,6-difluoro-4-(trans-4-(2-(trans-4-methylcyclohexyl)ethyl)cyclohexyl)phenyl)ethyl) chlorobenzene
310. 2,6-difluoro-4-(2-(2,6-difluoro-4-(trans-4-(2-(trans-4-ethylcyclohexyl)ethyl)cyclohexyl)phenyl)ethyl) chlorobenzene
311. 2,6-difluoro-4-(2-(2,6-difluoro-4-(trans-4-(2-(trans-4-n-propylcyclohexyl)ethyl)cyclohexyl)phenyl)ethyl) chlorobenzene
312. 2,6-difluoro-4-(2-(2,6-difluoro-4-(trans-4-(2-(trans-4-n-butylcyclohexyl)ethyl)cyclohexyl)phenyl)ethyl) chlorobenzene
313. 2,6-difluoro-4-(2-(2,6-difluoro-4-(trans-4-(2-(trans-4-n-pentylcyclohexyl)ethyl)cyclohexyl)phenyl)ethyl) chlorobenzene
314. 2,6-difluoro-4-(2-(2,6-difluoro-4-(trans-4-(2-(trans-4-n-hexylcyclohexyl)ethyl)cyclohexyl)phenyl)ethyl) chlorobenzene
315. 2,6-difluoro-4-(2-(2,6-difluoro-4-(trans-4-(2-(trans-4-n-heptylcyclohexyl)ethyl)cyclohexyl)phenyl)ethyl) chlorobenzene

EXAMPLE 6

Preparation of 4-(2-(4-(2-(trans-4-(2-(4-n-propylphenyl)ethyl)cyclohexyl)ethyl)phenyl)ethyl)chlorobenzene (compound expressed by general formula (I) wherein both ring A and ring C represent 1,4-phenylene, ring B represents trans-1,4-cyclohexylene, all of $Z_1$, $Z_2$, and $Z_3$ represent —$CH_2CH_2$—, both $L_1$ and $L_2$ represent H atom, and R represents n-propyl group, Compound No. 316)

(1) Solution prepared by dissolving 47.2 g of (2-(trans-4-(2-(4-n-propylphenyl)ethyl)cyclohexyl)ethyl)benzene in 500 ml of methylene chloride was cooled down to 0° C., and 34.7 g of aluminum chloride was added thereto and stirred. Oxalyl chloride in an amount of 33 g was added dropwise little by little thereto, it was raised up to room temperature, and stirred for 2 hours. After finishing of the reaction, it was added to 500 ml of water and extracted with 500 ml of methylene chloride. Organic layer was washed with water and dried over anhydrous magnesium sulfate, and the solvent was distilled off under a reduced pressure to obtain 33.2 g of (2-(trans-4-(2-(4-n-propylphenyl)ethyl)cyclohexyl)ethyl)benzoyl chloride.

(2) To 200 ml of toluene was added 7 ml of ethanol and 13 g of pyridine, and stirred. Liquid mixture of 33.2 g of the (2-(trans-4-(2-(4-n-propylphenyl)ethyl)cyclohexyl)ethyl) benzoyl chloride mentioned above and 200 ml of toluene was added dropwise thereto, and stirred under reflux for 2 hours. After cooled, the reaction solution was added to 500 ml of water and extracted with 200 ml of toluene. Organic layer was washed with water and dried over anhydrous magnesium sulfate, and the solvent was distilled off under a reduced pressure to obtain 26.9 g of (2-(trans-4-(2-(4-n-propylphenyl)ethyl)cyclohexyl)ethyl)ethylbenzoate.

(3) Under cooled condition with ice, 2.4 g of lithium aluminum hydride was added little by little to 200 ml of THF, and stirred. Liquid mixture of 26.9 g of the (2-(trans-4-(2-(4-n-propylphenyl)ethyl)cyclohexyl)ethyl) ethylbenzoate mentioned above and 100 ml of THF was added dropwise thereto, and stirred as it was cooled with ice for 2 hours. Ethyl acetate in an amount of 100 ml was added thereto. Reaction solution was added to 200 ml of dilute hydrochloric acid cooled with ice, and extracted with 500 ml of ethyl acetate. Organic layer was washed with water and dried over anhydrous magnesium sulfate, and the solvent was distilled off under a reduced pressure to obtain 19.5 g of (2-(trans-4-(2-(4-n-propylphenyl)ethyl)cyclohexyl)ethyl) benzyl alcohol.

(4) Dicyclohexylcarbodiimide in an amount of 11.9 g was suspended in 200 ml of methylene chloride and stirred. Solution prepared by dissolving 19.5 g of the (2-(trans-4-(2-(4-n-propylphenyl)ethyl)cyclohexyl)ethyl)benzyl alcohol mentioned above in 200 ml of methylene chloride was added dropwise therein and stirred at room temperature for 2 hours. Crude reaction solution was purified by a column chromatography over a silica gel and then the solvent was distilled off under a reduced pressure to obtain 11.8 g of (2-(trans-4-(2-(4-n-propylphenyl)ethyl)cyclohexyl)ethyl) benzaldehyde.

(5) Suspension of 16.8 g of 4-chlorobenzyltriphenyl-phosphonium bromide in 150 ml of THF was stirred under nitrogen gas stream, and 4 g of potassium-t-butoxide was added at room temperature. After stirred at room temperature for 1 hour, a solution of 11.8 g of the (2-(trans-4-(2-(4-n-propylphenyl)ethyl)cyclohexyl)ethyl)benzaldehyde mentioned above and 100 ml of THF was added thereto. After stirred at room temperature for 2 hours, 300 ml of water was added, and extracted with 500 ml of ethyl acetate. Organic layer was washed with water and dried over anhydrous magnesium sulfate, the solvent was distilled off under a reduced pressure, and then 500 ml of heptane was added thereto. Precipitate thus separated was filtered off, purified by a column chromatography over a silica gel by using ethyl acetate/heptane (1/5) as an eluent, and then the solvent was distilled off under a reduced pressure to obtain 10 of 4-(2-(4-(2-(trans-4-(2-(4-n-propylphenyl)ethyl)cyclohexyl) ethyl)phenyl)ethenyl)chlorobenzene.

(6) In a liquid mixture comprising 10 ml of ethanol and 10 ml of toluene was dissolved 3.0 g of the 4-(2-(4-(2-(trans-4-(2-(4-n-propylphenyl)ethyl)cyclohexyl)ethyl)phenyl) ethenyl)chlorobenzene, and 0.3 g of palladium/barium sulfate was added as catalyst and subjected to a catalytic reduction in hydrogen gas atmosphere. After finishing of the reaction, the catalyst was filtered off and the solvent was distilled off under a reduced pressure to obtain a light yellow oily product. This product was recrystallized from heptane to obtain 1.5 g of the subject compound.

According to the procedures mentioned above, the following Compounds No. 317 to No. 378 were synthesized:
No.
317. 4-(2-(4-(2-(trans-4-(2-(4-methylphenyl)ethyl) cyclohexyl)ethyl)phenyl)ethyl)chlorobenzene
318. 4-(2-(4-(2-(trans-4-(2-(4-ethylphenyl)ethyl) cyclohexyl)ethyl)phenyl)ethyl)chlorobenzene
319. 4-(2-(4-(2-(trans-4-(2-(4-n-butylphenyl)ethyl) cyclohexyl)ethyl)phenyl)ethyl)chlorobenzene
320. 4-(2-(4-(2-(trans-4-(2-(4-n-pentylphenyl)ethyl) cyclohexyl)ethyl)phenyl)ethyl)chlorobenzene
321. 4-(2-(4-(2-(trans-4-(2-(4-n-hexylphenyl)ethyl) cyclohexyl)ethyl)phenyl)ethyl)chlorobenzene
322. 4-(2-(4-(2-(trans-4-(2-(4-n-heptylphenyl)ethyl) cyclohexyl)ethyl)phenyl)ethyl)chlorobenzene
323. 2-fluoro-4-(2-(4-(2-(trans-4-(2-(4-methylphenyl)ethyl) cyclohexyl)ethyl)phenyl)ethyl)chlorobenzene
324. 2-fluoro-4-(2-(4-(2-(trans-4-(2-(4-ethylphenyl)ethyl) cyclohexyl)ethyl)phenyl)ethyl)chlorobenzene
325. 2-fluoro-4-(2-(4-(2-(trans-4-(2-(4-n-propylphenyl) ethyl)cyclohexyl)ethyl)phenyl)ethyl)chlorobenzene
326. 2-fluoro-4-(2-(4-(2-(trans-4-(2-(4-n-butylphenyl)ethyl) cyclohexyl)ethyl)phenyl)ethyl)chlorobenzene
327. 2-fluoro-4-(2-(4-(2-(trans-4-(2-(4-n-pentylphenyl) ethyl)cyclohexyl)ethyl)phenyl)ethyl)chlorobenzene
328. 2-fluoro-4-(2-(4-(2-(trans-4-(2-(4-n-hexylphenyl) ethyl)cyclohexyl)ethyl)phenyl)ethyl)chlorobenzene
329. 2-fluoro-4-(2-(4-(2-(trans-4-(2-(4-n-nonylphenyl) ethyl)cyclohexyl)ethyl)phenyl)ethyl)chlorobenzene
330. 4-(2-(2-fluoro-4-(2-(trans-4-(2-(4-methylphenyl)ethyl) cyclohexyl)ethyl)phenyl)ethyl)chlorobenzene
331. 4-(2-(2-fluoro-4-(2-(trans-4-(2-(4-ethylphenyl)ethyl) cyclohexyl)ethyl)phenyl)ethyl)chlorobenzene
332. 4-(2-(2-fluoro-4-(2-(trans-4-(2-(4-n-propylphenyl) ethyl)cyclohexyl)ethyl)phenyl)ethyl)chlorobenzene
333. 4-(2-(2-fluoro-4-(2-(trans-4-(2-(4-n-butylphenyl)ethyl) cyclohexyl)ethyl)phenyl)ethyl)chlorobenzene
334. 4-(2-(2-fluoro-4-(2-(trans-4-(2-(4-n-pentylphenyl) ethyl)cyclohexyl)ethyl)phenyl)ethyl)chlorobenzene
335. 4-(2-(2-fluoro-4-(2-(trans-4-(2-(4-n-hexylphenyl) ethyl)cyclohexyl)ethyl)phenyl)ethyl)chlorobenzene
336. 4-(2-(2-fluoro-4-(2-(trans-4-(2-(4-n-heptylphenyl) ethyl)cyclohexyl)ethyl)phenyl)ethyl)chlorobenzene
337. 2-fluoro-4-(2-(2-fluoro-4-(2-(trans-4-(2-(4-methylphenyl)ethyl)cyclohexyl)ethyl)phenyl)ethyl) chlorobenzene
338. 2-fluoro-4-(2-(2-fluoro-4-(2-(trans-4-(2-(4-ethylphenyl)ethyl)cyclohexyl)ethyl)phenyl)ethyl) chlorobenzene
339. 2-fluoro-4-(2-(2-fluoro-4-(2-(trans-4-(2-(4-n-propylphenyl)ethyl)cyclohexyl)ethyl)phenyl)ethyl) chlorobenzene
340. 2-fluoro-4-(2-(2-fluoro-4-(2-(trans-4-(2-(4-n-butylphenyl)ethyl)cyclohexyl)ethyl)phenyl)ethyl) chlorobenzene
341. 2-fluoro-4-(2-(2-flouro-4-(2-(trans-4-(2-(4-n-pentylphenyl)ethyl)cyclohexyl)ethyl)phenyl)ethyl) chlorobenzene
342. 2-fluoro-4-(2-(2-flouro-4-(2-(trans-4-(2-(4-n-hexylphenyl)ethyl)cyclohexyl)ethyl)phenyl)ethyl) chlorobenzene
343. 2-fluoro-4-(2-(2-fluoro-4-(2-(trans-4-(2-(4-n-octylphenyl)ethyl)cyclohexyl)ethyl)phenyl)ethyl) chlorobenzene
344. 2,6-difluoro-4-(2-(4-(2-(trans-4-(2-(4-methylphenyl) ethyl)cyclohexyl)ethyl)phenyl)ethyl)chlorobenzene
345. 2,6-difluoro-4-(2-(4-(2-(trans-4-(2-(4-ethylphenyl) ethyl)cyclohexyl)ethyl)phenyl)ethyl)chlorobenzene
346. 2,6-difluoro-4-(2-(4-(2-(trans-4-(2-(4-n-propylphenyl) ethyl)cyclohexyl)ethyl)phenyl)ethyl)chlorobenzene
347. 2,6-difluoro-4-(2-(4-(2-(trans-4-(2-(4-n-butylphenyl) ethyl)cyclohexyl)ethyl)phenyl)ethyl)chlorobenzene
348. 2,6-difluoro-4-(2-(4-(2-(trans-4-(2-(4-n-pentylphenyl) ethyl)cyclohexyl)ethyl)phenyl)ethyl)chlorobenzene
349. 2,6-difluoro-4-(2-(4-(2-(trans-4-(2-(4-n-hexylphenyl) ethyl)cyclohexyl)ethyl)phenyl)ethyl)chlorobenzene
350. 2,6-difluoro-4-(2-(4-(2-(trans-4-(2-(4-n-decylphenyl) ethyl)cyclohexyl)ethyl)phenyl)ethyl)chlorobenzene
351. 4-(2-(2,6-difluoro-4-(2-(trans-4-(2-(4-methylphenyl) ethyl)cyclohexyl)ethyl)phenyl)ethyl)chlorobenzene
352. 4-(2-(2,6-difluoro-4-(2-(trans-4-(2-(4-ethylphenyl) ethyl)cyclohexyl)ethyl)phenyl)ethyl)chlorobenzene
353. 4-(2-(2,6-difluoro-4-(2-(trans-4-(2-(4-n-propylphenyl) ethyl)cyclohexyl)ethyl)phenyl)ethyl)chlorobenzene
354. 4-(2-(2,6-difluoro-4-(2-(trans-4-(2-(4-n-butylphenyl) ethyl)cyclohexyl)ethyl)phenyl)ethyl)chlorobenzene
355. 4-(2-(2,6-difluoro-4-(2-(trans-4-(2-(4-n-pentylphenyl) ethyl)cyclohexyl)ethyl)phenyl)ethyl)chlorobenzene
356. 4-(2-(2,6-difluoro-4-(2-(trans-4-(2-(4-n-hexylphenyl) ethyl)cyclohexyl)ethyl)phenyl)ethyl)chlorobenzene
357. 4-(2-(2,6-difluoro-4-(2-(trans-4-(2-(4-n-heptylphenyl) ethyl)cyclohexyl)ethyl)phenyl)ethyl)chlorobenzene
358. 2,6-difluoro-4-(2-(2-fluoro-4-(2-(trans-4-(2-(4-methylphenyl)ethyl)cyclohexyl)ethyl)phenyl)ethyl) chlorobenzene
359. 2,6-difluoro-4-(2-(2-fluoro-4-(2-(trans-4-(2-(4-ethylphenyl)ethyl)cyclohexyl)ethyl)phenyl)ethyl) chlorobenzene
360. 2,6-difluoro-4-(2-(2-fluoro-4-(2-(trans-4-(2-(4-n-propylphenyl)ethyl)cyclohexyl)ethyl)phenyl)ethyl) chlorobenzene 361. 2,6-difluoro-4-(2-(2-fluoro-4-(2-(trans-4-(2-(4-n-butylphenyl)ethyl)cyclohexyl)ethyl)phenyl)ethyl) chlorobenzene
362. 2,6-difluoro-4-(2-(2-fluoro-4-(2-(trans-4-(2-(4-n-pentylphenyl)ethyl)cyclohexyl)ethyl)phenyl)ethyl) chlorobenzene
363. 2,6-difluoro-4-(2-(2-fluoro-4-(2-(trans-4-(2-(4-n-hexylphenyl)ethyl)cyclohexyl)ethyl)phenyl)ethyl) chlorobenzene
364. 2,6-difluoro-4-(2-(2-fluoro-4-(2-(trans-4-(2-(4-n-heptylphenyl)ethyl)cyclohexyl)ethyl)phenyl)ethyl) chlorobenzene
365. 2-fluoro-4-(2-(2,6-difluoro-4-(2-(trans-4-(2-(4-methylphenyl)ethyl)cyclohexyl)ethyl)phenyl)ethyl) chlorobenzene
366. 2-fluoro-4-(2-(2,6-difluoro-4-(2-(trans-4-(2-(4-ethylphenyl)ethyl)cyclohexyl)ethyl)phenyl)ethyl) chlorobenzene
367. 2-fluoro-4-(2-(2,6-difluoro-4-(2-(trans-4-(2-(4-n-propylphenyl)ethyl)cyclohexyl)ethyl)phenyl)ethyl) chlorobenzene
368. 2-fluoro-4-(2-(2,6-difluoro-4-(2-(trans-4-(2-(4-n-butylphenyl)ethyl)cyclohexyl)ethyl)phenyl)ethyl) chlorobenzene
369. 2-fluoro-4-(2-(2,6-difluoro-4-(2-(trans-4-(2-(4-n-pentylphenyl)ethyl)cyclohexyl)ethyl)phenyl)ethyl) chlorobenzene
370. 2-fluoro-4-(2-(2,6-difluoro-4-(2-(trans-4-(2-(4-n-hexylphenyl)ethyl)cyclohexyl)ethyl)phenyl)ethyl) chlorobenzene
371. 2-fluoro-4-(2-(2,6-difluoro-4-(2-(trans-4-(2-(4-n-heptylphenyl)ethyl)cyclohexyl)ethyl)phenyl)ethyl) chlorobenzene
372. 2,6-difluoro-4-(2-(2,6-difluoro-4-(2-(trans-4-(2-(4-methylphenyl)ethyl)cyclohexyl)ethyl)phenyl)ethyl) chlorobenzene
373. 2,6-difluoro-4-(2-(2,6-difluoro-4-(2-(trans-4-(2-(4-ethylphenyl)ethyl)cyclohexyl)ethyl)phenyl)ethyl) chlorobenzene
374. 2,6-difluoro-4-(2-(2,6-difluoro-4-(2-(trans-4-(2-(4-n-propylphenyl)ethyl)cyclohexyl)ethyl)phenyl)ethyl) chlorobenzene
375. 2,6-difluoro-4-(2-(2,6-difluoro-4-(2-(trans-4-(2-(4-n-butylphenyl)ethyl)cyclohexyl)ethyl)phenyl)ethyl) chlorobenzene
376. 2,6-difluoro-4-(2-(2,6-difluoro-4-(2-(trans-4-(2-(4-n-pentylphenyl)ethyl)cyclohexyl)ethyl)phenyl)ethyl) chlorobenzene
377. 2,6-difluoro-4-(2-(2,6-difluoro-4-(2-(trans-4-(2-(4-n-hexylphenyl)ethyl)cyclohexyl)ethyl)phenyl)ethyl) chlorobenzene
378. 2,6-difluoro-4-(2-(2,6-difluoro-4-(2-(trans-4-(2-(4-n-heptylphenyl)ethyl)cyclohexyl)ethyl)phenyl)ethyl) chlorobenzene

EXAMPLE 7

(Use Example 1)

Liquid crystal composition (hereinafter referred to as Composition A) comprising the following compounds had a NI point of 52.3° C., viscosity at 20° C. of 21.7 mPa·s, value of optical anisotropy (Δn) of 0.119, and value of dielectric anisotropy (Δε) of 10.7.

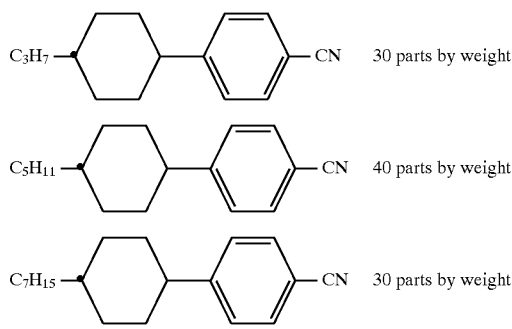

This Composition A was filled in a TN cell having a cell thickness of 9.0 μm and subjected to a determination for threshold voltage to find to be 1.60 V. Next, Compound No. 1 of the present invention prepared in Example 1 in an amount of 15 parts by weight was mixed with 85 parts by weight of the Composition A to prepare a liquid crystal composition, and the NI point which can be extrapolated from the composition was calculated to find to be 200.3° C. Viscosity at 20° C. was 53.7 mPa·s, value of optical anisotropy (Δn) was 0.199, and value of dielectric anisotropy (Δε) was 12.7, and the threshold voltage when the liquid crystal composition was filled in a TN cell having a cell thickness of 8.9 μm was 1.59 V. While this liquid crystal composition was left at −30° C. to confirm the miscibility at low temperatures, separation of crystals was not observed for more than 1 month.

Comparative Example 1

Liquid crystal composition was prepared in the same manner as in Example 7 with the exception that the following compound (hereinafter referred to as Comparative Compound 1) disclosed in Japanese Patent Publication No. Hei 2-44818 was used in place of Compound No. 1 of the present invention.

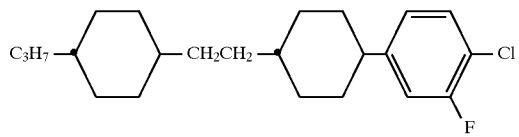

NI point which can be extrapolated from the composition was 106.3° C. Viscosity at 20° C. was 24.4 mPa·s, Δn was 0.109, and Δε was 8.7, and the threshold voltage when the liquid crystal composition was filled in a TN cell having a cell thickness of 8.9 μm was 1.69 V.

This composition was found to have a remarkably low value of Δn in particular.

Comparative Example 2

Liquid crystal compositions was prepared in the same manner as in Example 7 with the exception that either of the following two compounds (hereinafter referred to as Comparative Compound 2 or 3) both of which are disclosed in DE-4027315 was used, respectively, in place of Compound No. 1 of the present invention used in Example 7, and they were left at −30° C. to confirm the miscibility at low temperatures. Only 1 hour after they were left at −30° C., separation of crystals was confirmed for both compositions, and it was found that Comparative Compounds 2 and 3 are remarkably inferior in the miscibility at low temperatures.

Comparative Compound 2

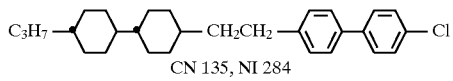

CN 135, NI 284

Comparative Compound 3

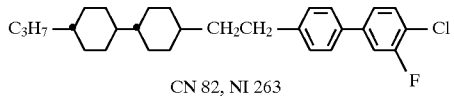

CN 82, NI 263

EXAMPLE 8
(Use Example 2)

Liquid crystal composition was prepared in the same manner as in Example 7 with the exception that Compound No. 17 was used in place of Compound No. 1 of the present invention. NI point which can be extrapolated from the composition was 214.3° C. Δn was 0.186, and Δε was 7.4, and the threshold voltage when the liquid crystal composition was filled in a TN cell having a cell thickness of 8.7 μm was 1.82 V. While this liquid crystal composition was left at −30° C., separation of crystals was not observed for more than 1 month.

EXAMPLE 9
(Use Example 3)

Liquid crystal composition was prepared in the same manner as in Example 7 with the exception that Compound No. 24 was used in place of Compound No. 1 of the present invention. NI point which can be extrapolated from the composition was 187.6° C. Viscosity at 20° C. was 59.0 mPa·s, Δn was 0.182, and Δε was 10.0, and the threshold voltage when the liquid crystal composition was filled in a TN cell having a cell thickness of 8.7 μm was 1.67 V. While this liquid crystal composition was left at −30° C., separation of crystals was not observed for more than 1 month.

EXAMPLE 10
(Use Example 4)

Liquid crystal composition was prepared in the same manner as in Example 7 with the exception that Compound No. 38 was used in place of Compound No. 1 of the present invention. NI point which can be extrapolated from the composition was 181.6° C. Viscosity at 20° C. was 67.7 mPa·s, Δn was 0.179, and Δε was 12.0, and the threshold voltage when the liquid crystal composition was filled in a TN cell having a cell thickness of 8.7 μm was 1.70 V. While this liquid crystal composition was left at −30° C., separation of crystals was not observed for more than 1 month.

EXAMPLE 11
(Use Example 5)

Liquid crystal composition was prepared in the same manner as in Example 7 with the exception that Compound No. 52 was used in place of Compound No. 1 of the present invention. NI point which can be extrapolated from the composition was 160.3° C. Viscosity at 20° C. was 71.7 mPa·s, Δn was 0.172, and Δε was 10.0, and the threshold voltage when the liquid crystal composition was filled in a TN cell having a cell thickness of 8.7 μm was 1.62 V. While this liquid crystal composition was left at −30° C., separation of crystals was not observed for more than 1 month.

EXAMPLE 12
(Use Example 6)

Ni point of the liquid crystal composition (hereinafter referred to as Composition B) comprising the following compounds was 72.4° C.

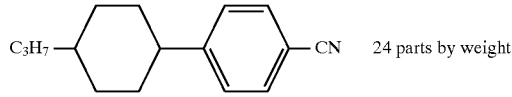 24 parts by weight

 36 parts by weight

 25 parts by weight

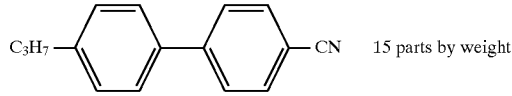 15 parts by weight

Viscosity at 20° C. was 27.0 mPa·s, Δn was 0.137, and Δε was 11.0. The threshold voltage when the liquid crystal composition was filled in a TN cell having a cell thickness of 9.0 μm was determined to find to be 1.78 V. Next, 15 parts by weight of Compound 75 obtained in Example 2 was added to 85 parts by weight of this composition to prepare a liquid crystal composition. NI point which can be extrapolated from this composition was 159.1° C. Viscosity at 20° C. was 60.7 mPa·s, Δn was 0.198, and Δε was 7.0, and the threshold voltage when the liquid crystal composition was filled in a TN cell having a cell thickness of 8.7 μm was 1.81 V. While this liquid crystal composition was left at −30° C., separation of crystals was not observed for more than 1 month.

Industrial Applicability

According to the present invention, novel liquid crystalline compounds having both a large optical anisotropy and a large dielectric anisotropy, exhibit a liquid crystal phase at a wide temperature range, and have a good miscibility with known liquid crystalline compounds at low temperatures, and liquid crystal compositions which contain the liquid crystalline compound and are particularly preferable for TFT mode can be provided.

We claim:

1. A liquid crystalline compound expressed by formula (I)

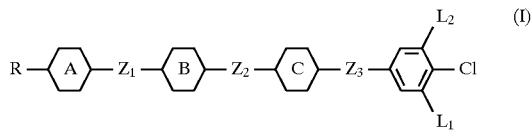

wherein ring B represents trans-1,4-cyclohexylene group, and ring A and ring C independently represent trans-1,4-cyclohexylene group or 1,4-phenylene group, one or more hydrogen atoms on the six-membered ring of which may be replaced by halogen atoms, $Z_1$ represents —$CH_2CH_2$—, $Z_2$, and $Z_3$ represent single bond, $L_1$ and $L_2$ represent H or a halogen atom, and R represents an alkyl group or alkoxy group having 1 to 10 carbon atoms.

2. The liquid crystalline compound according to claim 1 wherein ring A represents trans-1,4-cyclohexylene group.

3. A The liquid crystalline compound according to claim 2 wherein ring C represents monofluoro-1,4-phenylene group.

4. The liquid crystalline compound according to claim 3 wherein $L_1$ represents fluorine atom.

5. The liquid crystalline compound according to claim 2 wherein ring C represents difluoro-1,4-phenylene group.

6. The liquid crystalline compound according to claim 5 wherein $L_1$ represent fluorine atom.

7. A liquid crystal composition comprising at least two compounds, at least one of which is a liquid crystalline compound defined in any one of claims 1 or 2 through 6.

8. A liquid crystal composition comprising, as a first component, at least one liquid crystalline compound defined in any one of claims 1 or 2 through 6, and, as a second component, at least one compound selected from the group of compounds expressed by formula (II), (III), or (IV)

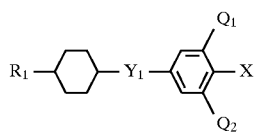  (II)

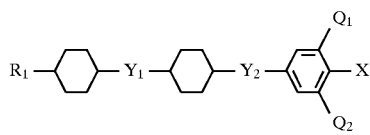  (III)

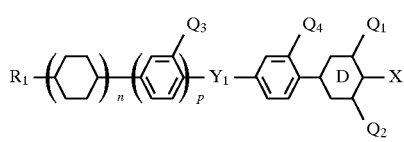  (IV)

wherein $R_1$ represents an alkyl group having 1 to 10 carbon atoms, X represents F, Cl, $CF_3$, $OCF_3$, $OCF_2H$, or an alkyl group having 1 to 10 carbon atoms, $Q_1$, $Q_2$, $Q_3$, and $Q_4$ independently represent H or F, n is 1 or 2, p is 0 or 1, $Y_1$ and $Y_2$ independently represent —$CH_2CH_2$—, —CH=CH—, or single bond, and ring D represents trans-1,4-cyclohexylene group or 1,4-phenylene group.

9. A liquid crystal composition comprising, as a first component, at least one liquid crystalline compound defined in any one of claims 1 or 2 through 6, and, as a second component, at least one compound selected from the group of compounds expressed by formula (V), (VI), (VII), (VIII), or (IX)

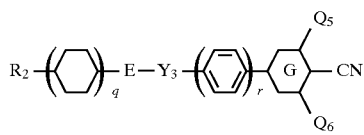  (V)

wherein $R_2$ represents F, an alkyl group having 1 to 10 carbon atoms, or an alkenyl group having 2 to 10 carbon atoms, any methylene group (—$CH_2$—) in which alkyl group or alkenyl group may be replaced by oxygen atom (—O—) provided that in no case are two or more adjacent methylene groups replaced by oxygen atom, $Y_3$ represents —$CH_2CH_2$—, —COO—, or single bond, $Q_5$ and $Q_6$ independently represent H or F, E represents trans-1,4-cyclohexylene group, 1,4-phenylene group, or trans-1,3-dioxane-2,5-diyl group, ring G represents trans-1,4-cyclohexylene group or 1,4-phenylene group, and q and r are independently 0 or 1,

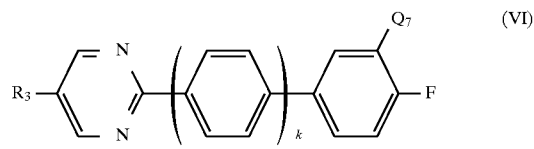  (VI)

wherein $R_3$ represents an alkyl group having 1 to 10 carbon atoms, $Q_7$ represents H or F, and k is 0 or 1,

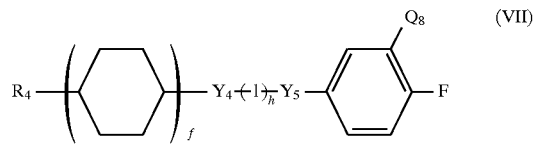  (VII)

wherein $R_4$ represents an alkyl group having 1 to 10 carbon atoms, I represents trans-1,4-cyclohexylene group or 1,4-phenylene group, $Q_8$ represents H or F, $Y_4$ represents —COO— or single bond, $Y_5$ represents —COO— or —C≡C—, and f and h are independently 0 or 1,

  (VIII)

wherein $R_5$ and $R_6$ independently represent an alkyl group, alkoxy group, or alkoxymethyl group having 1 to 10 carbon atoms, J represents trans-1,4-cyclohexylene group, 1,3-pyrimidine-2,5-diyl group, or 1,4-phenylene group, K represents trans-1,4-cyclohexylene group or 1,4-phenylene group, and $Y_6$ represents —C≡C—, —COO—, —$CH_2CH_2$—, or single bond,

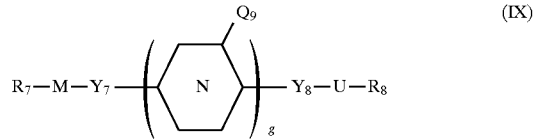  (IX)

wherein $R_7$ represents an alkyl group or alkoxy group having 1 to 10 carbon atoms, $R_8$ represents an alkyl group having 1 to 10 carbon atoms, any methylene group (—$CH_2$—) in $R_8$ may be replaced by oxygen atom (—O—) provided that in no case are two or more adjacent methylene groups replaced by oxygen atom, M represents trans-1,4-cyclohexylene group or 1,3-pyrimidine-2,5-diyl group, each of ring N and U independently represents trans-1,4-cyclohexylene group or 1,4-phenylene group, $Y_7$ represents —$CH_2CH_2$—, —COO—, or single bond, $Y_8$ represents —C≡C—, —COO—, or single bond, g is 0 or 1, and $Q_9$ represents H or F.

10. A liquid crystal display device comprising the liquid crystal composition defined in claim 7.

11. A liquid crystal display device comprising the liquid crystal composition defined in claim 8.

12. A liquid crystal display device comprising the liquid crystal composition defined in claim 9.

13. A liquid crystal composition comprising, as a first component, at least one liquid crystalline compound defined in any one of claims 1 or 2 through 6, as a part of a second component, at least one liquid crystalline compound selected from the group of compounds expressed by formula (II), (III), or (IV), and, as the other part of the second component, at least one liquid crystalline compound selected from the group of compounds expressed by formula (V), (VI), (VII), (VIII), or (IX),

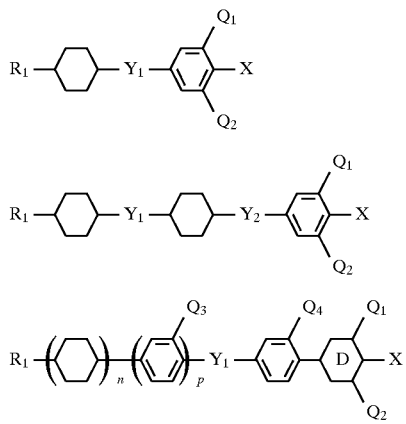 (II)

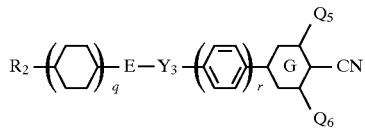 (III)

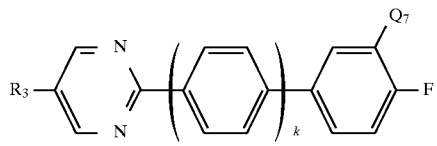 (IV)

wherein $R_1$ represents an alkyl group having 1 to 10 carbon atoms, X represents F, Cl, $CF_3$, $OCF_3$, $OCF_2H$, or an alkyl group having 1 to 10 carbon atoms, $Q_1$, $Q_2$, $Q_3$, and $Q_4$ independently represent H or F, n is 1 or 2, p is 0 or 1, $Y_1$ and $Y_2$ independently represent $—CH_2CH_2—$, $—CH=CH—$, or single bond, and ring D represents trans-1,4-cyclohexylene group or 1,4-phenylene group,

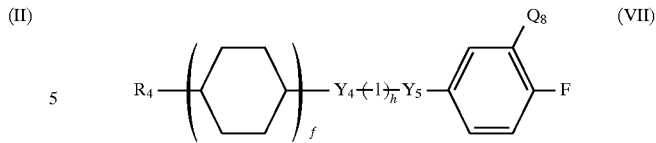 (V)

wherein $R_2$ represents F, an alkyl group having 1 to 10 carbon atoms, or an alkenyl group having 2 to 10 carbon atoms, any methylene group ($—CH_2—$) in which alkyl group or alkenyl group may be replaced by oxygen atom ($—O—$) provided that in no case are two or more adjacent methylene groups replaced by oxygen atom, $Y_3$ represents $—CH_2CH_2—$, $—COO—$, or single bond, $Q_5$ and $Q_6$ independently represent H or F, E represents trans-1,4-cyclohexylene group, 1,4-phenylene group, or trans-1,3-dioxane-2,5-diyl group, ring G represents trans-1,4-cyclohexylene group or 1,4-phenylene group, and q and r are independently 0 or 1,

 (VI)

wherein $R_3$ represents an alkyl group having 1 to 10 carbon atoms, $Q_7$ represents H or F, and k is 0 or 1,

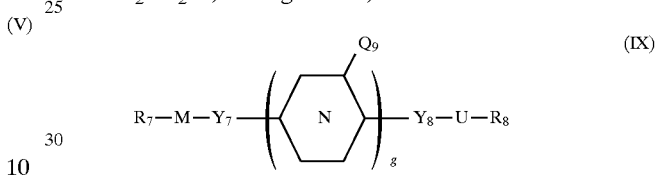 (VII)

wherein $R_4$ represents an alkyl group heaving 1 to 10 carbon atoms, I represents trans-1,4-cyclohexylene group or 1,4-phenylene group, $Q_8$ represents H or F, $Y_4$ represents $—COO—$ or single bond, $Y_5$ represents $—COO—$ or $—C \equiv C—$, and f and h are independently 0 or 1, $$R_5—J—Y_6—K—R_6 \quad \text{(VIII)}$$

wherein $R_5$ and $R_6$ independently represent an alkyl group, alkoxy group, or alkoxymethyl group having 1 to 10 carbon atoms, J represents trans-1,4-cyclohexylene group, 1,3-pyrimidine-2,5-diyl group, or 1,4-phenylene group, K represents trans-1,4-cyclohexylene group or 1,4-phenylene group, and $Y_6$ represents $—C \equiv C—$, $—COO—$, $—CH_2CH_2—$, or single bond, $$R_7—M—Y_7—\text{(ring N)}_g—Y_8—U—R_8 \quad \text{(IX)}$$

wherein $R_7$ represents an alkyl group or alkoxy group having 1 to 10 carbon atoms, $R_8$ represents an alkyl group having 1 to 10 carbon atoms, any methylene group ($—CH_2—$) in $R_8$ may be replaced by oxygen atom ($—O—$) provided that in no case are two or more adjacent methylene groups replaced by oxygen atom, M represents trans-1,4-cyclohexylene group or 1,3-pyrimidine-2,5-diyl group, each of ring N and U independently represents trans-1,4-cyclohexylene group or 1,4-phenylene group, $Y_7$ represents $—CH_2CH_2—$, $—COO—$, or single bond, $Y_8$ represents $—C \equiv C—$, $—COO—$, or single bond, g is 0 or 1, and $Q_9$ represents H or F.

14. A liquid crystal display device comprising the liquid crystal composition defined in claim 13.

* * * * *